(12) United States Patent
Hu et al.

(10) Patent No.: US 8,969,312 B2
(45) Date of Patent: Mar. 3, 2015

(54) LOW SIDE EFFECT PHARMACEUTICAL COMPOSITION CONTAINING ANTITUBERCULOSIS DRUGS

(75) Inventors: Oliver Yaopu Hu, Taipei (TW); Tonho Young, Taipei County (TW); Chenghuei Hsiong, Taipei (TW); Wenliang Chang, Taipei (TW); Tungyuan Shih, Kaohsiung (TW); Hsintien Ho, Taipei (TW)

(73) Assignee: National Defense Education and Research Foundation, Taipei County (TW)

( * ) Notice: Subject to any disclaimer, the term of this patent is extended or adjusted under 35 U.S.C. 154(b) by 0 days.

(21) Appl. No.: 14/003,629

(22) PCT Filed: Apr. 20, 2011

(86) PCT No.: PCT/CN2011/000688
§ 371 (c)(1),
(2), (4) Date: Oct. 17, 2013

(87) PCT Pub. No.: WO2012/142724
PCT Pub. Date: Oct. 26, 2012

(65) Prior Publication Data
US 2014/0038921 A1    Feb. 6, 2014

(51) Int. Cl.
*A61K 31/70* (2006.01)

(52) U.S. Cl.
USPC .............. 514/23; 514/27; 514/133; 514/354

(58) Field of Classification Search
USPC ...................... 514/23, 27, 354, 133
See application file for complete search history.

(56) References Cited

U.S. PATENT DOCUMENTS 8,304,394 B2 * 11/2012 Hu et al. ................ 514/23

FOREIGN PATENT DOCUMENTS

| CN | 1408354 A | | 4/2003 |
| CN | 1857280 A | | 11/2006 |
| WO | WO2010009572 | * | 1/2010 |

OTHER PUBLICATIONS

Dickson et al. et al., American Review of Respiratory Disease, 1977, 116(4):627-635.*
International Search report from PCT application PCT/CN2011/000688 which cites CN1408354A and CN1857280, 2011.
Written Opinion of the ISA from PCT application PCT/CN2011/000688, 2011.
The publication of PCT application PCT/CN2011/000688 published as WO 2012/142724, 2011.

* cited by examiner

*Primary Examiner* — Rei-tsang Shiao
(74) *Attorney, Agent, or Firm* — WPAT, P.C.; Anthony King

(57) ABSTRACT

A pharmaceutical composition for treating tuberculotic diseases with no side effect/low side effect is provided by the present invention, which pharmaceutically effective amount of one or more compounds chosen from isoniazid, rifampin, pyrazinamide and ethambutol, and pharmaceutically effective amount of substances which can reduce the side effect of the antituberculosis agents.

12 Claims, 21 Drawing Sheets

LOW SIDE EFFECT PHARMACEUTICAL COMPOSITION CONTAINING ANTITUBERCULOSIS DRUGS

BRIEF SUMMARY OF THE INVENTION

The present invention features a novel, no/low side-effect pharmaceutical composition, comprising the pharmaceutically effective dose of isoniazid (INH) and/or the pharmaceutically effective dose of rifampin (RIF) and/or the pharmaceutically effective dose of pyrazinamide (PZA) and/or the pharmaceutically effective dose of ethambutol (EMB) and pharmaceutically effective dose of at least one of the following compounds which were cytochrome P450 2E1 (CYP2E1) or amidase inhibitors. Said compound was selected from the following groups of compounds: Nordihydroguaiaretic acid, (−)-Epigallocatechin-3-gallate, Capillarisin, Kaempferol, Phloretin, Hesperetin, 6-Gingerol, gallic acid, Isoliquritigenin, Naringenin, (+)-Taxifolin, Wongonin, Protocatechuic acid, (+)-Catechin, β-naphthoflavone, Embelin, Trans-Cinnamic acid, (−)-Epicatechin, Phloridzin, Brij 58, Brij 76, Brij 35, Tween 20, Tween 80, Tween 40, PEG 2000, PEG 400, Trans-Cinnamaldehyde, Daidzein, Isovitexin, β-Myrcene, Quercetin, (+)-Limonene, Myricetin, Quercitrin, Luteolin-7-Glucoside, Morin, Neohesperidin, Hesperidin, (−)-Epigallocatechin, Luteolin, Hyperoside, Ethyl Myristate, Tamarixetin, Baicalein, Rutin, Baicalin, Apigenin, (+)-Epicatechin, (−)-Epicatechin-3-gallate, Silybin, Vitexin, Genistein, Isorhamnetin, Diosmin, Puerarin, Umbelliferone, Galangin, fisetin, Cremophor EL, Sodium Lauryl Sulfate, Microcrystalline cellulose, Dicalcium phosphate dihydrate, Mannitol, Cremophor RH40, Sucralose, Crospovidone, Sodium starch glycolate, Crospovidone, Eudragit S100, Croscarmellose sodium, Menthol, Saccharin, hydroxypropylcellulose, Pregelatinized starch, Dextrates NF hydrated, Citric acid, Aerosil 200, PEG 8000, Sorbic acid, Lemon oil, Hydroxy propylcellulose, Sodium benzoate, Acesulfame K, Hydroxypropyl methylcellulose, Hydroxy ethyl methylcellulose, Methyl cellulose, Sodium cyclamate, Lactose monohydrate, Maltodextrin, Glyceryl behenate, Oxide red, Glycerrin monostearate, Copovidone K28, Starch acetate, Magnesium stearate, Sodium lauryl sulfate, Povidone K-30, Benzyl alcohol, Methylparaben, Propylparaben, Solutol H15, Butylated hydroxyl anisol. Furthermore, the present invention features a novel, no/low side-effect pharmaceutical composition, comprising the pharmaceutically effective dose of pyrazinamide (PZA) and/or the pharmaceutically effective dose of isoniazid (INH) and/or the pharmaceutically effective dose of rifampin (RIF) and/or the pharmaceutically effective dose of ethambutol (EMB) and/or the pharmaceutically effective dose of other pharmaceutical compositions and pharmaceutically effective dose of at least one of the following compounds which were amidase inhibitors. Said compound was selected from the following groups of compounds: Quercetin, Galangin, Morin, fisetin, Isoliquritigenin, Myricetin, Luteolin, Kaempferol, Capillarisin, Cremophor EL, Sodium Lauryl Sulfate, Tween 20, Brij58.

FIELD OF THE INVENTION

The present invention relates to a novel, low side-effect compound complex which contains isoniazid (INH) and/or rifampin (RIF) and/or pyrazinamide (PZA) and/or ethambutol (EMB) and at least one of CYP2E1 or amidase inhibitors to reduce isoniazid or pyrazinamide induced hepatotoxicity.

BACKGROUND OF THE INVENTION

According to the estimate made by World Health Organization (WHO), nearly one-third of the world populations are infected with tuberculosis (TB) and around eight million new cases were reported every year. In Taiwan, registered new tuberculosis cases have increased dramatically in the past few years, and approximately sixty out of a hundred thousand people were infected at present. However, only three-forth of the patients were receiving the treatments. As indicated by the Department of Health (DOH), 4.2 people died of tuberculosis everyday in Taiwan, and hepatotoxicity and neurological damage, e.g. auditory and optic neuroninjury, etc. are common clinical side effects observed in patients treated with TB drugs. Among which, hepatotoxicity is the most commonside effect reported. Furthermore, due to the fact that chronic hepatitis B and C are prevailing diseases in Taiwan, if 14,000 people were infected with tuberculosis each year, it is estimated that approximately 2,000 to 3,000 people among those active tuberculosis patients also have chronic liver disorders and require the treatment of tuberculosis. Therefore, the most universal side effect of the tuberculosis treatment, hepatotoxicity, is an iatrogenicdisorder that should not be neglected.

Most primary anti-tuberculosis drugs, e.g. isoniazid, pyrazinamide, and rifampin, have potential side effects such as hepatotoxicity. Among those drugs, isoniazid is the most effective, but also the one that can easily induce hepatotoxicity. Isoniazid induced hepatotoxicity has been reported since the late 60's, and roughly 0.1 to 1% of the treated patients showed clinical symptoms of hepatotoxicity (Kopanoff D E et al., Isoniazid-related hepatitis: a U.S. Public Health Service cooperative surveillance study, 1978. Am. Rev Respir Dis 117:991-1001; Nolan C M et al., Hepatotoxicity associated with isoniazid preventive therapy: a 7-year survey from a public health tuberculosis clinic. 1999. JAMA 281: 1014). Moreover, 10 to 20% of those patients exhibited abnormal liver functions in the absence of clinical symptoms, and the first sign of liver malfunction usually took place two months after the initial treatment of isoniazid (Steele M A et al., Toxic hepatitis with isoniazid and rifampin: A meta-analysis. 1991. Chest. 99: 465).

As shown in FIG. 1, the major pathway of isoniazid metabolism is acetylation to acetylisoniazidby N-acetyltransferase (NAT) followed by rapidly hydrolysis to isonicotinic acid and acetylhydrazine. Acetylhydrazine can be further acetylated into either non-toxic diacetylhydrazine or toxic molecules which include acetyldiazene, acetylonium ion, acetylradical, and ketene etc. by N-acetyltransferase and Cytochrome P450 2E1 (CYP 450 2E1), respectively. Additionally, in the presence of oxygen and NADPH, acetylhydrazine can react with Cytochrome P450 2E1 and produce free radicals, and such oxidation stress can induce cell death. Moreover, both isoniazid and acetylhydrazine can be hydrolyzed to toxic hydrazine by amidase.

Recent studies have indicated that hydrazine (not isoniazid or acetylhydrazine) is most likely to be responsible for INH-induced hepatotoxicity observed in rabbits and rats, and the severity of hepatotoxicity is positively correlate with the concentration of hydrazine (Sarich T C, Youssefi M, Zhou T, Adams S P, Wall R A, Wright J M. Role of hydrazine in the mechanism of isoniazid hepatotoxicity in rabbits. 1996. Arch Toxicol 70: 835-840; Yue J, Peng R X, Yang J, Kong R, Liu J. CYP2E1 mediated isoniazid-induced hepatotoxicity in rats. 2004. Acta Pharmacol Sin. 25: 699-704.). Sarich et al. in 1999 reported that bis-p-nitrophenyl phosphate (BNPP), an inhibitor of amidase, can prevent isoniazid-induced hepatotoxicity by inhibition of hydrazine production (Sarich T C, Adams S P, Petricca G, Wright J M Inhibition of isoniazid-induced hepatotoxicity in rabbits by pretreatment with an amidase inhibitor. 1999. J Pharmacol Exp Ther. 289: 695-702).

Cytochrome P450 2E1 (CYP2E1) is constitutively expressed in liver and is involved in metabolic pathways of many compounds, e.g. $CCl_4$ and acetaminophen (Lee S S, Buters J T, Pineau T, Fernandez-Salguero P, Gonzalez F J. Role of CYP2E1 in the hepatotoxicity of acetaminophen. 1996. J Biol Chem 271: 12063-12067; Wong F W, Chan W Y, Lee S S. Resistance to carbon tetrachloride-induced hepatotoxicity in mice which lack CYP2E1 expression. 1998. Toxicol Appl Pharmacol. 153: 109-118). Nevertheless, the role of CYP22E1 in isoniazid-induced hepatotoxicity remains unclear. Isoniazid is an inducer of CYP22E1 (Ramaiah S K, Apte U, Mehendale H M. Cytochrome P4502E1 induction increases thioacetamide liver injury in diet-restricted rats. 2001. Drug Metab Dispos. 29: 1088-1095.). Some studies have suggested that CYP22E1 in liver is involved in the mechanism of isoniazid-induced hepatotoxicity (Yue J, Peng R X, Yang J, Kong R, Liu J. CYP2E1 mediated isoniazid-induced hepatotoxicity in rats. 2004. Acta Pharmacol Sin. 25: 699-704; Huang Y S, Chem H D, Su W J, Wu J C, Chang S C, Chiang C H, Chang F Y, et al. Cytochrome P450 2E1 genotype and the susceptibility to antituberculosis drug-induced hepatitis. 2003. Hepatology 37: 924-930.). In vitro studies have also suggested that disulfuram (DSF) and its metabolite, diethyldithiocarbamate, are the selective mechanism-based inhibitors for CYP2E1 in human liver microsomes (Guengerich F P, Kim D H, Iwasaki M. Role of human cytochrome P-450 IIE1 in the oxidation of many low molecular weight cancer suspects. 1991. Chem Res Toxicol. 4: 168-179; Hunter A L, Neal R A Inhibition of hepatic mixed-function oxidase activity in vitro and in vivo by various thiono-sulfur-containing compounds. 1975. Biochem Pharmacol. 24: 2199-2205.). Brady et al. have demonstrated that oral administration of a single dose of disulfuram (DSF) in rats can result in immunoreactive hepatic content and rapidly reduce the activity of CYP2E1 (Brady J F, Xiao F, Wang M H, Li Y, Ning S M, Gapac J M, Yang C S. Effects of disulfuram on hepatic P45011E1, other microsomal enzymes, and hepatotoxicity in rats. 1991. Toxicol Appl Pharmacol. 108: 366-373.).

Sodhi et al. reported in 1997 that oxidative-stress is one of the factors that contribute to the hepatotoxicity induced by isoniazid and rifampicin in young rats (Sodhi C P, Rana S V, Mehta S K, Vaiphei K, Attari S, Mehta S. Study of oxidative-stress in isoniazid-rifampicin induced hepatic injury in young rats. 1997. Drug Chem Toxicol 20: 255-269). Numerous research focused on identification of appropriate biomarkers so as to evaluate the in vivo rate of oxidation has discovered three types of biomarkers: biomarkers for damage caused by lipid, protein and nucleic acid oxidation. 8-iso-prostaglandin $F_{2\alpha}$ (8-iso-$PGF_{2\alpha}$) is the product of lipid oxidation of arachidonic acid and is chemically stable. The amount of 8-iso-$PGF_{2\alpha}$ can be used as an indicator for in vivo lipid oxidation and the oxidation is likely related to the production of free radicals, oxidative damage, and antioxidant deficiency (Morrow J D, Hill K E, Burk R F, Nammour T M, Badr K F, Roberts L I, 2nd. A series of prostaglandin F2-like compounds are produced in vivo in humans by a non-cyclooxygenase, free radical-catalyzed mechanism. 1990. Proc. Natl. Acad. Sci. USA 87: 9383-9387; Morrow J D. The isoprostanes: their quantification as an index of oxidant stress status in vivo. 2000. Drug Metab Rev. 32: 377-385.). Presently, many methods are available for measuring the concentration of 8-iso-$PGF_{2\alpha}$ which include enzyme immunoassay (Devaraj S, Hirany S V, Burk R F, Jialal I. Divergence between LDL oxidative susceptibility and urinary F(2)-isoprostanes as measures of oxidative stress in type 2 diabetes. 2001. Clin. Chem. 47: 1974-1979.); radioimmunoassay (Helmersson J, Basu S. F2-isoprostane excretion rate and diurnal variation in human urine. 1999. Prostaglandins Leukot. Essent. Fatty Acids 61: 203-205.); gas-chromatography mass spectrometry (Morrow J D, Roberts L J, 2nd. Mass spectrometric quantification of F2-isoprostanes in biological fluids and tissues as measure of oxidant stress. 1999. Methods Enzymol. 300: 3-12.) and liquid chromatography mass spectrometry (Li H, Lawson J A, Reilly M, Adiyaman M, Hwang S W, Rokach J, FitzGerald G A. Quantitative high performance liquid chromatography/tandem mass spectrometric analysis of the four classes of F(2)-isoprostanes in human urine. 1999. Proc. Natl. Acad. Sci. USA 96: 13381-13386.) etc. In addition, 8-iso-$PGF_{2\alpha}$ in human urine and its metabolite, 2,3-dinor-8-iso-$PGF_{2\alpha}$, can be extracted by C18 solid phase extraction (SPE) and then apply to LC/MS/MS analysis (Liang Y, Wei P, Duke R W, Reaven P D, Harman S M, Cutler R G, Heward C B. Quantification of 8-iso-prostaglandin-$F_{2\alpha}$ and 2,3-dinor-8-iso-prostaglandin-$F_{2\alpha}$ in human urine using liquid chromatography-tandem mass spectrometry. 2003. Free Radic. Biol. Med 34: 409-418.).

Currently, the available tests for assessing liver function so as to monitor the progress of liver damage and screen for chronic liver diseases include both conventional and quantitative tests. The most common tests used are examining the concentrations of plasma aspartate aminotransferase (AST), plasma alanine aminotransferase (ALT), plasma alkaline phosphatase, and liver metabolites, e.g. bilirubin and albumin etc.; or studying the coagulation factors by measuring the prothrombin time etc. (Carlisle R, Galambos J T, Warren W D. The relationship between conventional liver tests, quantitative function tests, and histopathology in cirrhosis. 1979. Dig. Dis. Sci. 24: 358-362.).

The tests of liver function mostly are based on the turn-over or time-dependent serum concentrations of a test substrate that is metabolized almost exclusively via the liver (hepatic elimination). The clearance of such substrates is determined by the hepatic portal vein and hepatic artery blood flow, as well as by the extraction of these substances by the liver. The hepatic blood flow correlates with the amount of the substances supplied to the liver. On the other hand, its elimination is determined by the hepatic metabolic capacity (Herold C, Heinz R, Niedobitek G, Schneider T, Hahn E G, Schuppan D. Quantitative testing of liver function in relation to fibrosis in patients with chronic hepatitis B and C. 2001. Liver 21: 260-265.).

Galactose is one type of carbohydrates that has high extraction ratio and 90% of its metabolism was processed in liver. In Liver, galactose was epimerized to glucose-1-phosphate by galactokinase and the reaction of galactokinase is the rate-limiting step in galactose metabolism. Due to the high extraction ratio of galatose and related hepatic blood flow, galactose elimination capacity became the most widespread test for examining liver function. At present, no specific test was available for evaluating residual liver function in rats, hence, measuring the metabolism capacity of a definite compound (e.g. galactose) can provide information on both rate-limiting step(s) in liver metabolism and representative value of residual liver function (Keiding S, Johansen S, Tonnesen K. Kinetics of ethanol inhibition of galactose elimination in perfused pig liver. 1977. Scand J. Clin. Lab Invest. 37: 487-494; Keiding S, Johansen S, Winkler K. Hepatic galactose elimination kinetics in the intact pig. 1982. Scand J. Clin. Lab Invest. 42: 253-259).

Galactose elimination capacity (GEC) is a well-established quantitative test for assessing human liver function (Lindskov J. The quantitative liver functions as measured by the galactose elimination capacity. I. Diagnostic value and relations to clinical, biochemical, and histological findings in patients with steatosis and patients with cirrhosis. 1982. Acta Med. Scand. 212: 295-302). Nonetheless, the requirement of obtaining multiple blood samples so as to establish a standard curve impedes its clinical applications. Consequently, galactose single point (GSP) test was used instead in numerous studies to assess human liver function. The inventor(s) of the present invention used GSP method to test liver function of patients with chronic hepatitis; liver cirrhosis; and hepatoma, and demonstrated that GSP test can precisely identify these liver disorders (Tang H S, Hu O Y. Assessment of liver function using a novel galactose single point method. 1992. Digestion 52: 222-231). Moreover, previous study has shown that GSP test can be successfully applied to measuring the residual liver function among patients with chronic liver diseases after treatment of promazine and cefoperazone (Hu O Y, Tang H S, Chang C L. The influence of chronic lobular hepatitis on pharmacokinetics of cefoperazone—a novel galactose single-point method as a measure of residual liver function. 1994. Biopharm Drug Dispos 15: 563-576; Hu O Y, Hu T M, Tang H S. Determination of galactose in human blood by high-performance liquid chromatography: comparison with an enzymatic method and application to the pharmacokinetic study of galactose in patients with liver dysfunction. 1995. J. Pharm. Sci. 84: 231-235; Hu O Y, Tang H S, Sheeng T Y, Chen T C, Curry S H. Pharmacokinetics of promazine in patients with hepatic cirrhosis—correlation with a novel galactose single point method. 1995. J. Pharm. Sci. 84: 111-114). In addition, GSP test was recommended by FDA, U.S.A. in the published "Guidance for Industry" to be used as one of the tests for assessing liver function (FDA Center for Drug Evaluation and Research (CDER) Pharmacokinetics in patients with impaired hepatic function: Study design, data analysis, and impact on dosing and labeling. Guidance for Industry, U.S. Department of Health and Human Service. 2003. pp 5). In conclusion, the primary anti-tuberculosis drug, isoniazid, has many side effects and is not well-designed, hence, improvement is much needed.

SUMMARY OF THE INVENTION

The present invention provides a novel, low side-effect compound complex comprising isoniazid (INH) and/or rifampin (RIF) and/or pyrazinamide (PZA) and/or ethambutol (EMB) and a cytochrome P450 2E1 (CYP2E1) inhibitor or a amidase inhibitor and such complex can considerably reduce INH-induced side-effects, particularly hepatotoxicity.

The novel compound complex mentioned above contains pharmaceutically effective doses of isoniazid (INH) and/or the pharmaceutically effective dose of rifampin (RIF) and/or the pharmaceutically effective dose of pyrazinamide (PZA) and/or the pharmaceutically effective dose of ethambutol (EMB) and pharmaceutically effective dose of at least one of the following compounds which were cytochrome P450 2E1 (CYP2E1) or amidase inhibitors. Said compound was selected from the following groups of compounds: Nordihydroguaiaretic acid, (−)-Epigallocatechin-3-gallate, Capillarisin, Kaempferol, Phloretin, Hesperetin, 6-Gingerol, gallic acid, Isoliquritigenin, Naringenin, (+)-Taxifolin, Wongonin, Protocatechuic acid, (+)-Catechin, β-naphthoflavone, Embelin, Trans-Cinnamic acid, (−)-Epicatechin, Phloridzin, Brij 58, Brij 76, Brij 35, Tween 20, Tween 80, Tween 40, PEG 2000, PEG 400, Trans-Cinnamaldehyde, Daidzein, Isovitexin, β-Myrcene, Quercetin, (+)-Limonene, Myricetin, Quercitrin, Luteolin-7-Glucoside, Morin, Neohesperidin, Hesperidin, (−)-Epigallocatechin, Luteolin, Hyperoside, Ethyl Myristate, Tamarixetin, Baicalein, Rutin, Baicalin, Apigenin, (+)-Epicatechin, (−)-Epicatechin-3-gallate, Silybin, Vitexin, Genistein, Isorhamnetin, Diosmin, Puerarin, Umbelliferone, Galangin, fisetin, Cremophor EL, Sodium Lauryl Sulfate, Microcrystalline cellulose, Dicalcium phosphate dihydrate, Mannitol, Cremophor RH40, Sucralose, Crospovidone, Sodium starch glycolate, Crospovidone, Eudragit S100, Croscarmellose sodium, Menthol, Saccharin, hydroxypropylcellulose, Pregelatinized starch, Dextrates NF hydrated, Citric acid, Aerosil 200, PEG 8000, Sorbic acid, Lemon oil, Hydroxy propylcellulose, Sodium benzoate, Acesulfame K, Hydroxypropyl methylcellulose, Hydroxy ethyl methylcellulose, Methyl cellulose, Sodium cyclamate, Lactose monohydrate, Maltodextrin, Glyceryl behenate, Oxide red, Glycerrin monostearate, Copovidone K28, Starch acetate, Magnesium stearate, Sodium lauryl sulfate, Povidone K-30, Benzyl alcohol, Methylparaben, Propylparaben, Solutol H15, Butylated hydroxyl anisol.

Furthermore, the present invention features a novel, no/low side-effect pharmaceutical composition, comprising the pharmaceutically effective dose of pyrazinamide (PZA) and/or the pharmaceutically effective dose of isoniazid (INH) and/or the pharmaceutically effective dose of rifampin (RIF) and/or the pharmaceutically effective dose of ethambutol (EMB) and/or the pharmaceutically effective dose of other pharmaceutical compositions and pharmaceutically effective dose of at least one of the following compounds which were amidase inhibitors. Said compound was selected from the following groups of compounds: Quercetin, Galangin, Morin, fisetin, Isoliquritigenin, Myricetin, Luteolin, Kaempferol, Capillarisin, Cremophor EL, Sodium Lauryl Sulfate, Tween 20, Brij58.

Moreover, the novel compound complex with no/low side effects addressed in the present invention also includes, but is not limited to pharmaceutically acceptable excipients and such excipients can be diluents, fillers, binders, disintegrating agents or lubricants, such as Tween 20, Tween 40, Tween 60, Tween 80, Brij 35, Brij 58 Brij 76, Pluronic F68, Pluronic F127, (Poloxamer 407), PEG 400, PEG 2000, PEG 4000, Span 60, Span 80, Myri 52, PEG 8000, Acesulfame potassium, Aerosil 200, (Colloidal silicon dioxide), Butylated hydroxyl anisol, Corn starch, Crospovidone, Croscarmellose sodium, Dicalcium phosphate dihydrate, EDTA 2 Na, Lactose, Lactose monohydrate, Lactose S.G, Low-substituted hydroxypropylcellulose, Maltodextrin, Mannitol, Menthol, Propyl paraben, Methyl paraben, Microcrystalline cellulose, Guar gum, Xanthan gum, Pregelatinized starch, Povidone K-30, Sodium starch glycolate, Sodium lauryl sulfate, Sucralose, Solutol H15, Cremophor EL, Cremophor RH40, Sodium cyclamate, PVP K90F, Oxide red, Hydroxypropyl methylcellulose, Chemy, Lemon oil, Sorbic acid, Benzyl alcohol, Glycerrin, Sodium benzolate, Starch acetate, Citric acid, Sorbitol solution, Opady white, Dextrates, NF hydrate, Magnesium stearate, Alginic acid, Eudragit E90, Eeudragit E, Glyceryl behenate, Gelucire, kollidon VA64 (copovidone K28), Hydrochoric acid, Hydroxy ethyl methyl cellulose, Hydroxy propyl cellulose, Methyl cellulose, Methacrylic acid copolymer type B (Eudragit 100), Maltose, Methacrylic Eudragit S100 acid copolymer, PEG 1450, Povidone K-90, phosphoric acid 85%, polyoxyl 40 hydrogenated castor oil (RH 40), Polyoxyl 35 castor oil (EL 35), sodium dihydrogen phosphate, saccarin, triethyl citrate, Tri-Sodium Citrate or other compound which was include in the list of USFDA Generally Recognized as Safe (GRAS).

The inventor(s) of the present invention expanded the previous application and further discloses the results showing reduction of the hepatoxicity and other side effects induced by the existing anti-TB drug, isoniazid (INH). In addition, the previous application, PCT application number PCT/CS2008/

001353 (A novel low side effect isoniazid composition), revealed that treatments that combined isoniazid with the pharmaceutical composition CYP2E1 inhibitors notably reduced hapatotoxicity and other side effects caused by isoniazid. However, the follow up studies conducted by the inventor(s) further demonstrated that random combinations of these compounds may not prevent hepatotoxicity caused by isoniazid. For example, in vivo animal study indicated that daily intraperitoneal injection of Kaempferol (3.78 mg/kg) and INH/RIF (50/100 mg/kg) for 3 weeks significantly inhibited the liver toxicity induced by isoniazid in mice. The results of relevant liver function tests including GOT, GPT and GSP in the control group (INH/RIF 50/100 mg/kg) were 571±295 U/L, 364±192 U/L, and 866±339 mg of/L, respectively. On the other hand, GOT, GPT and GSP measured from mice injected with 3.78 mg/kg Kaempferol were 89±19 U/L, 48±21 U/L and 245±98 mg/L, respectively, and were close to normal range. Nonetheless, administration of reduced Kaempferol (1.89 mg/kg) showed no obvious reduction in various liver function tests and less effectiveness in mice injected with 3.78 mg/kg Kaempferol when compared to the control group. Hence, combination of the CYP2E1 inhibitors and isoniazid indeed prevents liver toxicity caused by isoniazid, but the dose must be carefully determined. Based on the obtained results, the present invention focuses on determination of the inhibitor dosage.

The present invention provides following beneficial effects compared with prior arts:

1 The new no/low side effect isoniazid composition provided in the present invention significantly reduced liver toxicity caused by INH when compared with administration of INH alone, combined INH and/or Rifampin (RIF), or INH and/or pyrazinamide (PZA) as showed in various tests including biochemical analysis (ALT and AST values), pathological analysis, residual liver function test (GSP and GEC values) and oxidative stress indicators (the concentration of plasma 8-iso-PGF2α), and be used to vary the nicotine amide (INH), different nicotine amide (INH) and/or standing complex amphotericin (rifampin, RIF), the different nicotine amide (INH) and/or propylthiouracil isonicotinic amide (pyrazinamide, PZA) test results compared with each other in, has significantly reduced the use of different nicotine amide (INH) of the liver caused by the toxic side effects.

2 The new no/low side effect isoniazid composition disclosed in the present invention may also be used as a prodrug that acts as the cytochrome P450 2E1 (CYP2E1) inhibitor or amide hydrolase (amidase) inhibitor in traditional Chinese Medicine. The composition provided in the present invention was extracted from natural traditional Chinese herbs/drugs and exhibits no physiological or chemical toxicity. Most importantly, the present composition shows significant inhibitory activity against human liver cytochrome P450 2E1 activity.

DETAILED DESCRIPTION OF THE SEVERAL VIEWS OF THE DRAWINGS

The foregoing summary, as well as the following detailed description of the invention, will be better understood when read in conjunction with the appended drawings. It should be understood, however, that the invention is not limited to the preferred embodiments shown.

Figure 3:
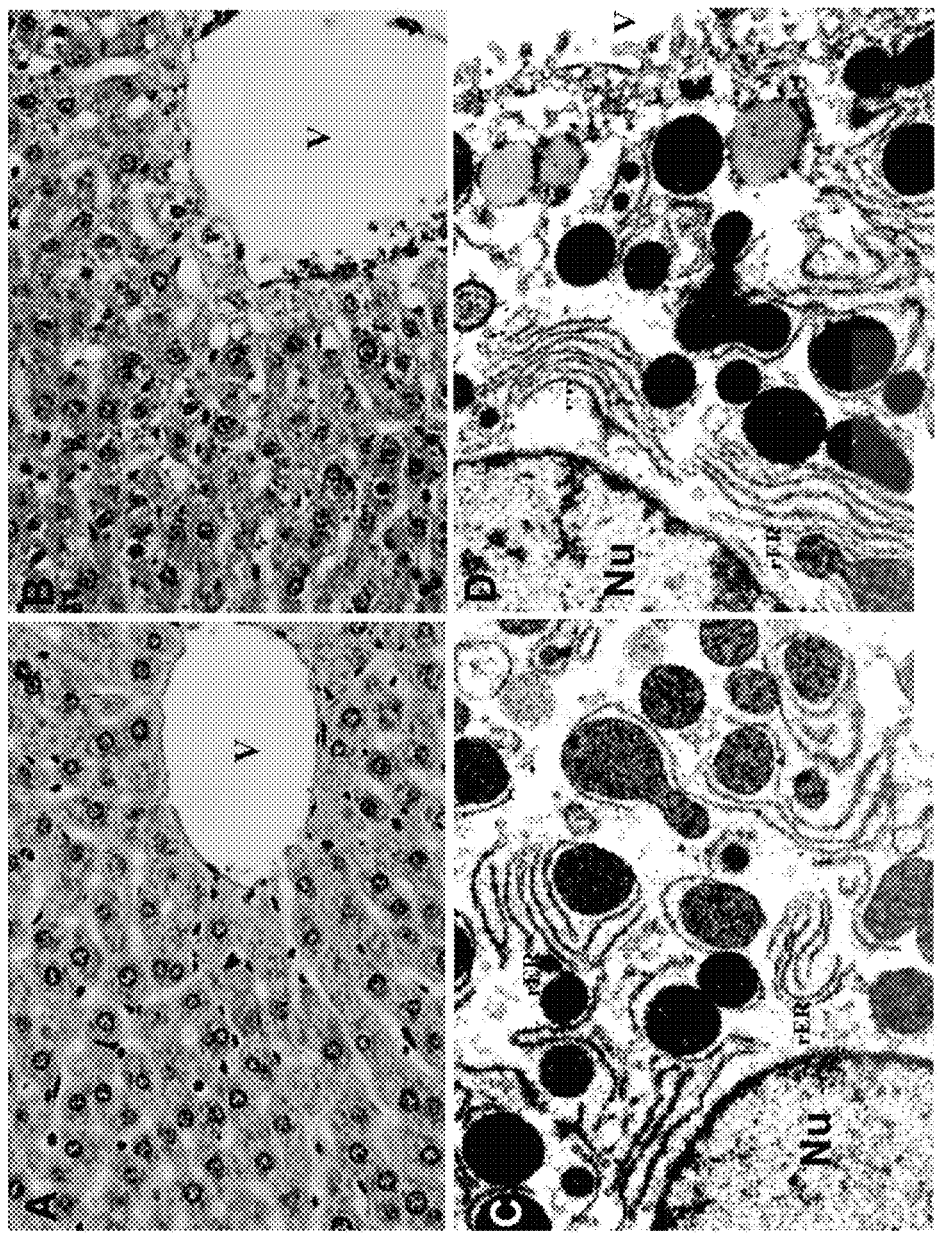

FIG. 3 shows the H&E staining of liver sections of rats treated with control and INH. FIG. 3A shows the normal hepatic tissue from control group (H&E staining, 400×), FIG. 3B shows central portal vein (V) hepatocyte damage and vacuolization (H&E staining, 400×), FIG. 3C is the electron microscope scan of rat liver sections from control group, Nu: nucleus (9,000×), FIG. 3D shows electron microscope scan of rat liver sections from INH group. In compare with control group, the rough endoplasmic reticulum (rER) in rats treated with INH increased significantly, Nu: nucleus (9,000×).

Figure 4A:
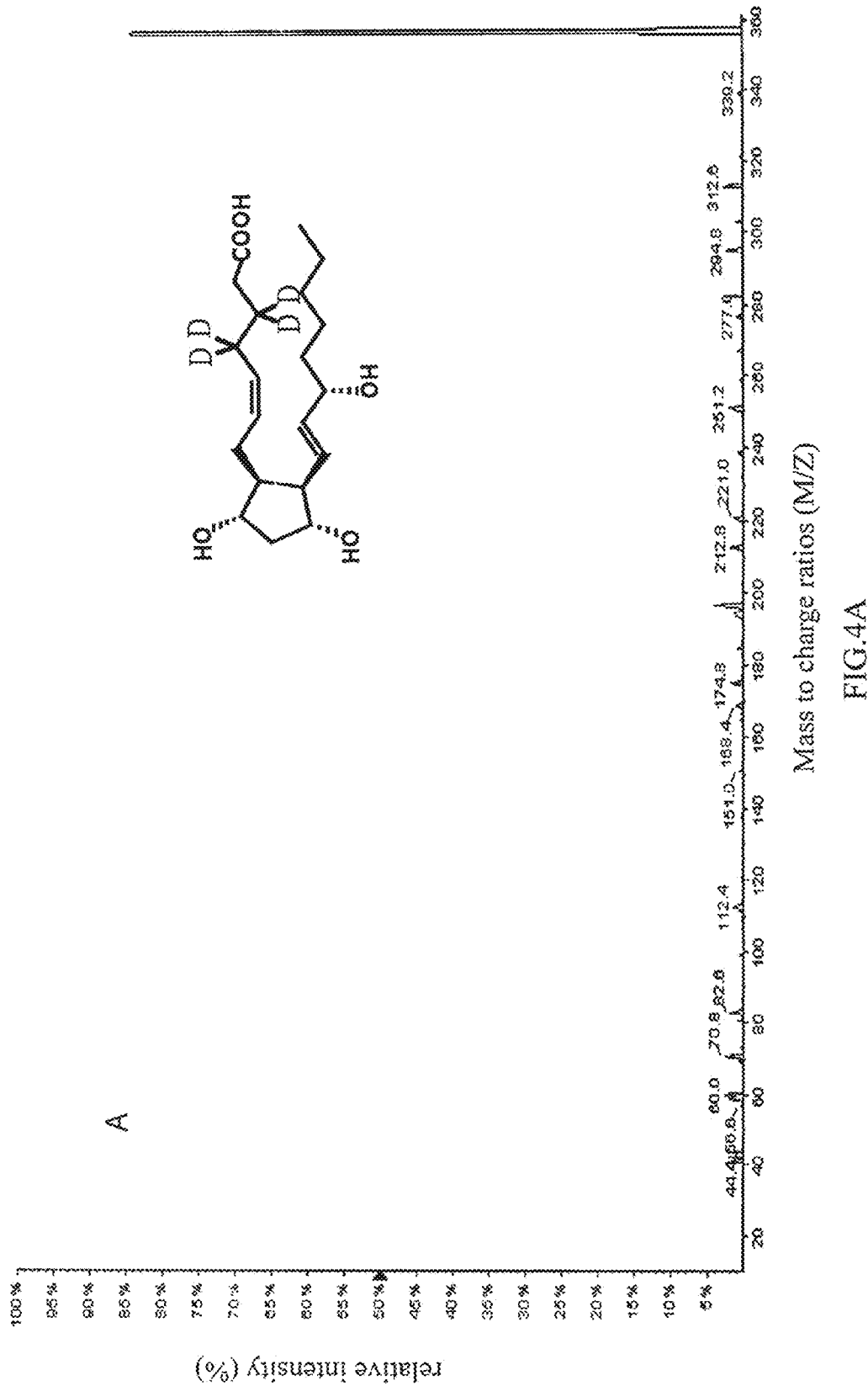
Figure 4B:
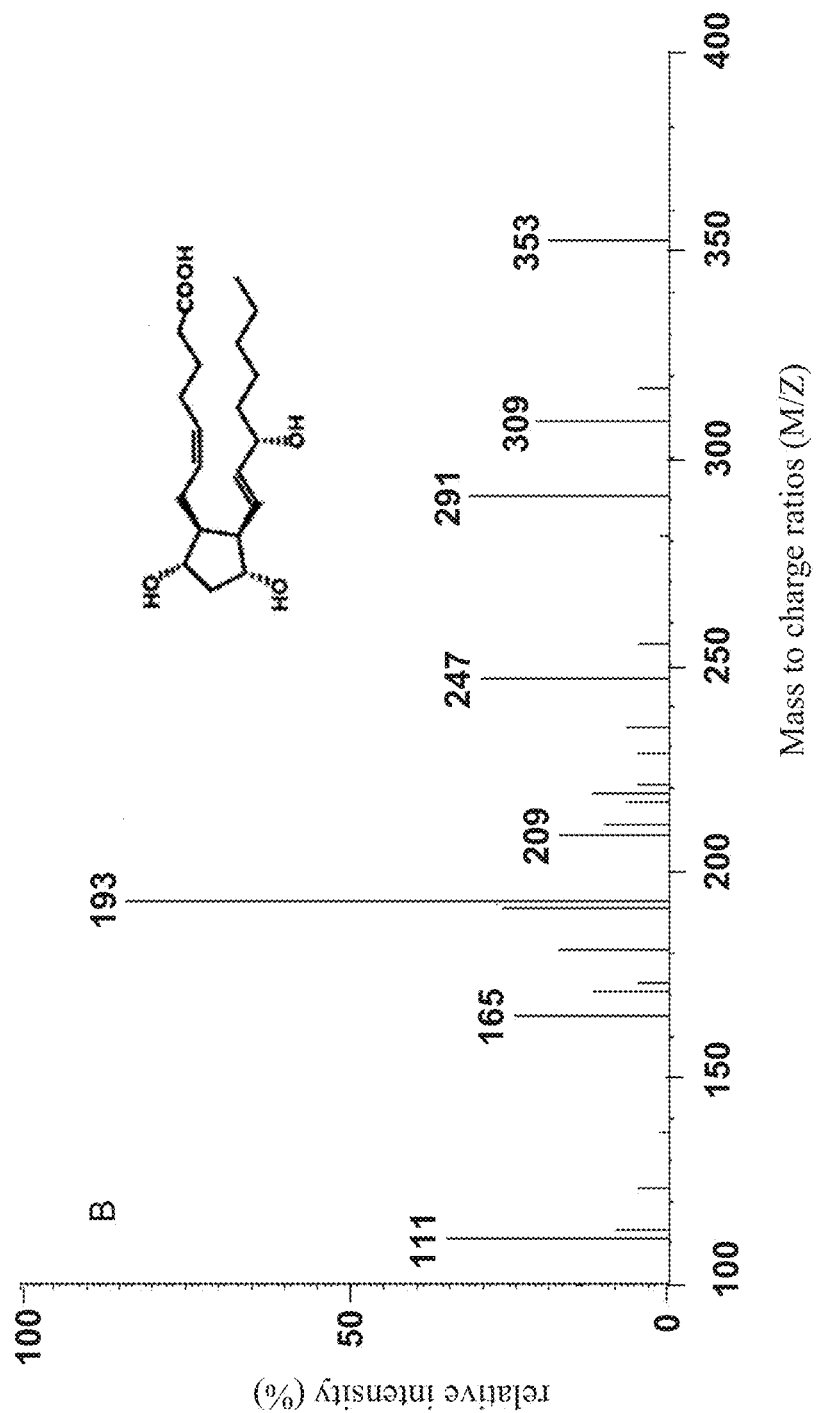

FIG. 4 shows the molecular structures and chronographs of 8-iso-PGF$_{2\alpha}$-d$_4$ (A) and 8-iso-PGF$_{2\alpha}$ (B).

Figure 5:
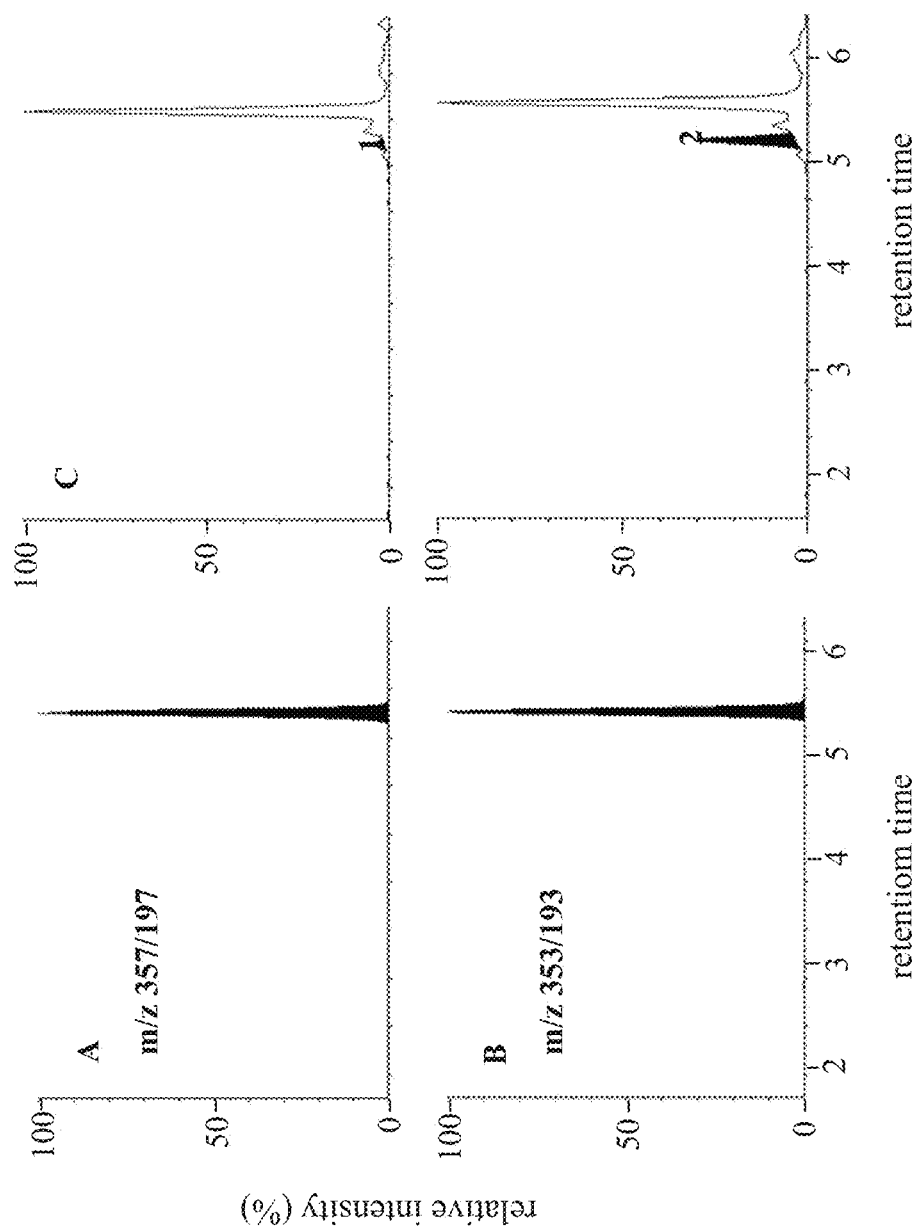

FIG. 5 shows LC/MS/MS chromatograph of reference compounds using MRM (multiple reaction monitor) mode. (A) Spiked with internal standard solution of 250 pg 8-iso-PGF$_{2\alpha}$-d$_4$, (B) spiked with internal standard solution of 100 pg 8-iso-PGF$_{2\alpha}$, and (C) blank sample solution. Ion pairs are m/z 357/197 and m/z 353/193 for 8-iso-PGF$_{2\alpha}$-d$_4$ (A) (as internal standard) and 8-iso-PGF$_{2\alpha}$ (B) (as internal standard), respectively. Peak1: blank plasma; Peak2: internal standard plasma.

Figure 6:
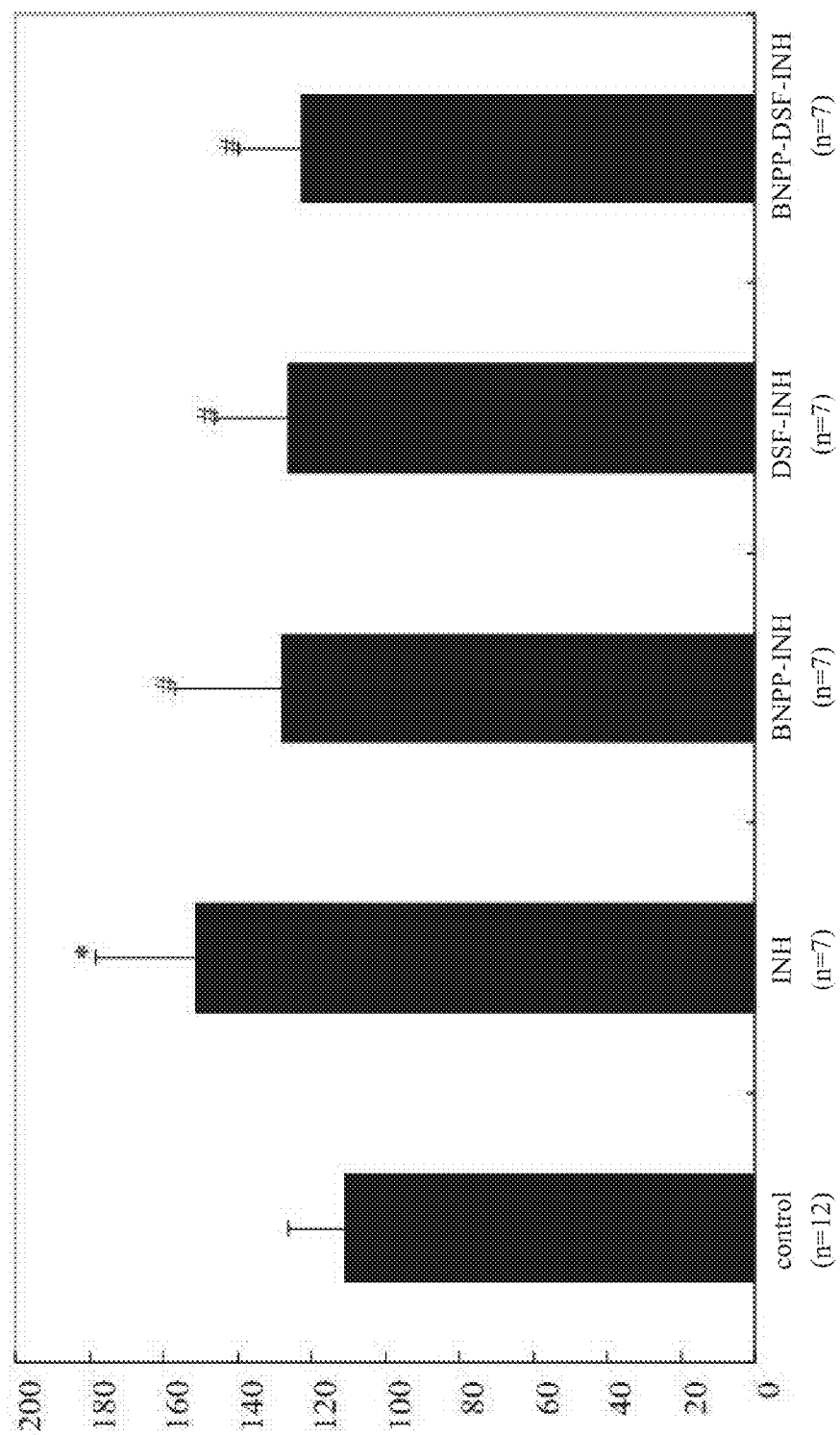

FIG. 6 shows the plasma 8-iso-PGF$_{2\alpha}$ concentrations of rats treated with control, INH, BNPP-INH, DSF-INH and BNPP-DSF-INH. Values represent the mean±SD, * indicates significant differences between experimental and control groups, P<0.001 and # indicates significant differences between experimental and control groups, P<0.05.

Figure 7:
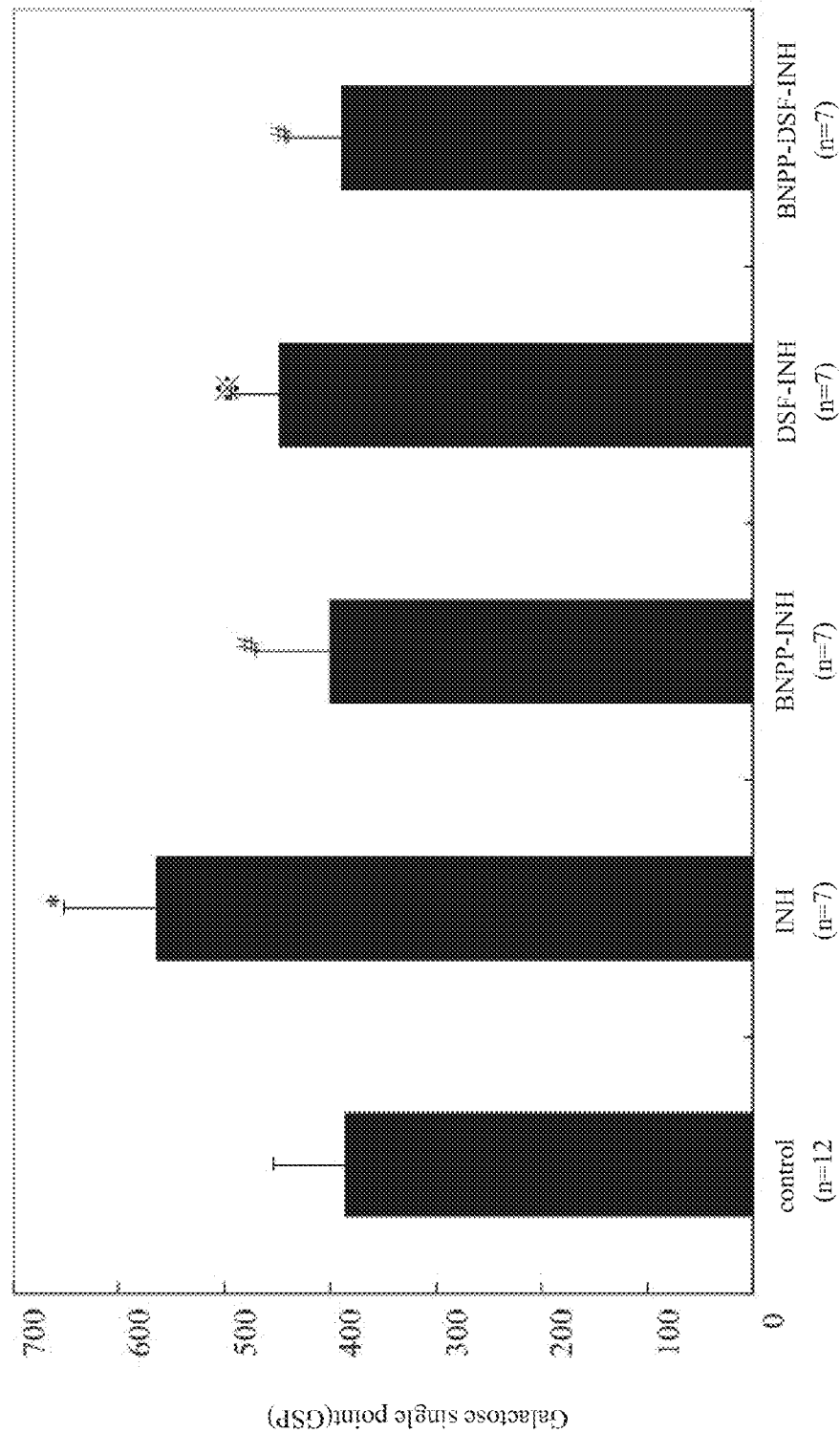

FIG. 7 shows the GSP values of rats treated with control, INH, BNPP-INH, DSF-INH and BNPP-DSF-INH. Values represent the mean±SD, * indicates significant differences between experimental and control groups, P<0.001; # indicates significant differences between experimental and control groups, P<0.001; and indicates significant differences between experimental and control groups, P<0.005.

Figure 8:
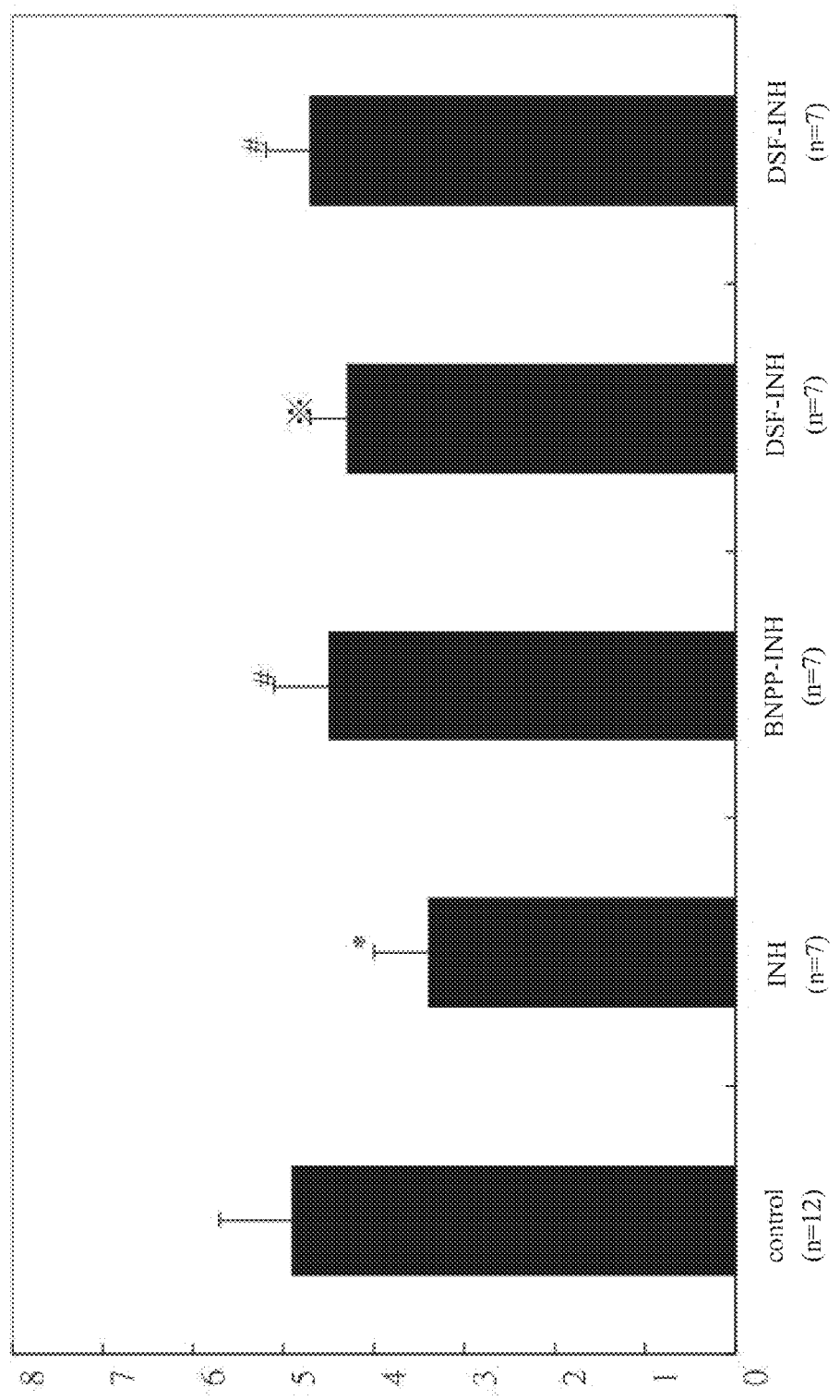

FIG. 8 shows the GEC values of rats treated with control, INH, BNPP-INH, DSF-INH and BNPP-DSF-INH. Values represent the mean±SD, * indicates significant differences between experimental and control groups, P<0.001; # indicates significant differences between experimental and control groups, P<0.005; and indicates significant differences between experimental and control groups, P<0.005.

Figure 9:
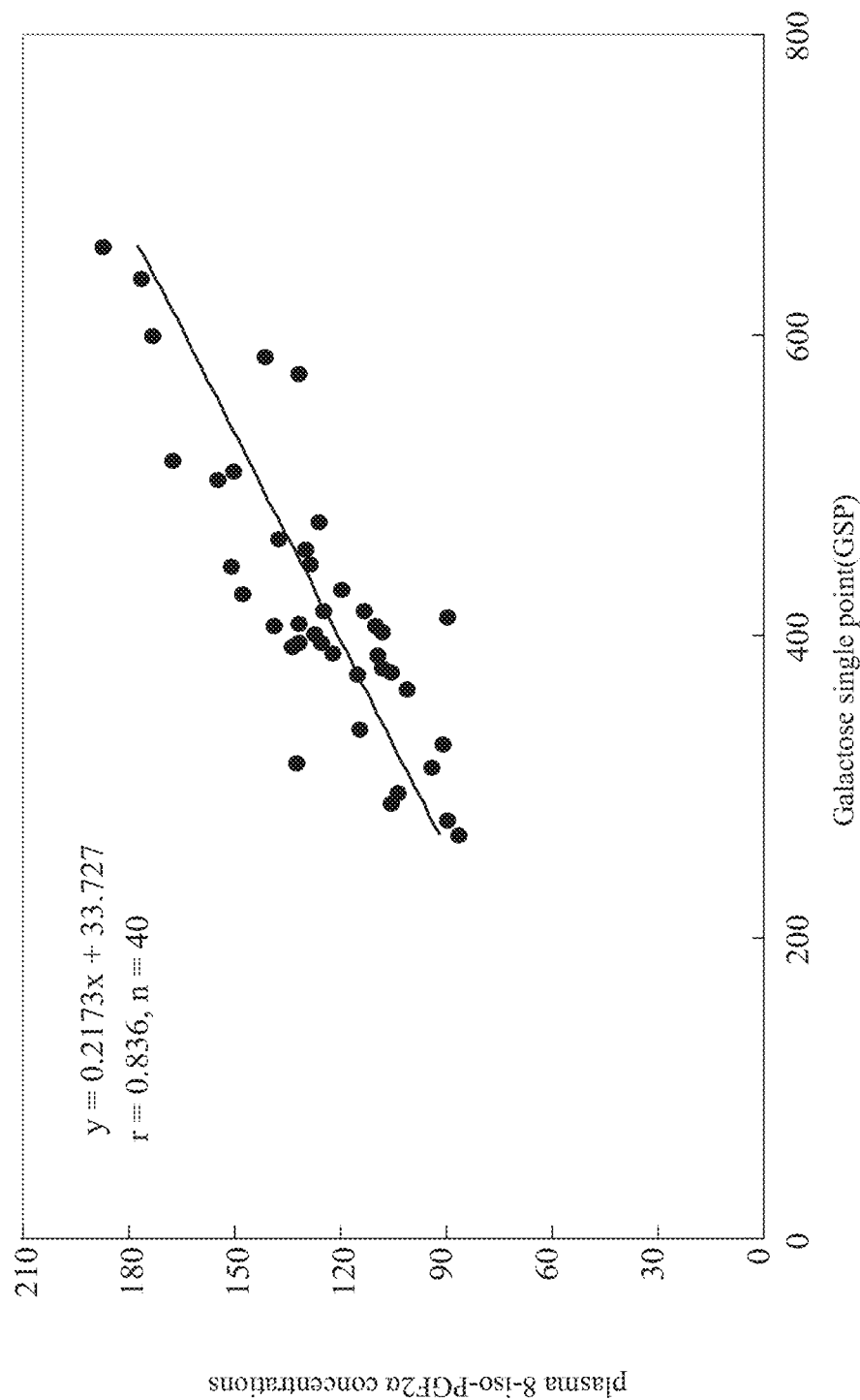

FIG. 9 is the statistical analysis results and demonstrated that GSP test values highly correlate with the concentration of 8-iso-PGF$_{2\alpha}$ in rats treated with control, INH, BNPP-INH, DSF-INH and BNPP-DSF-INH.

Figure 10:
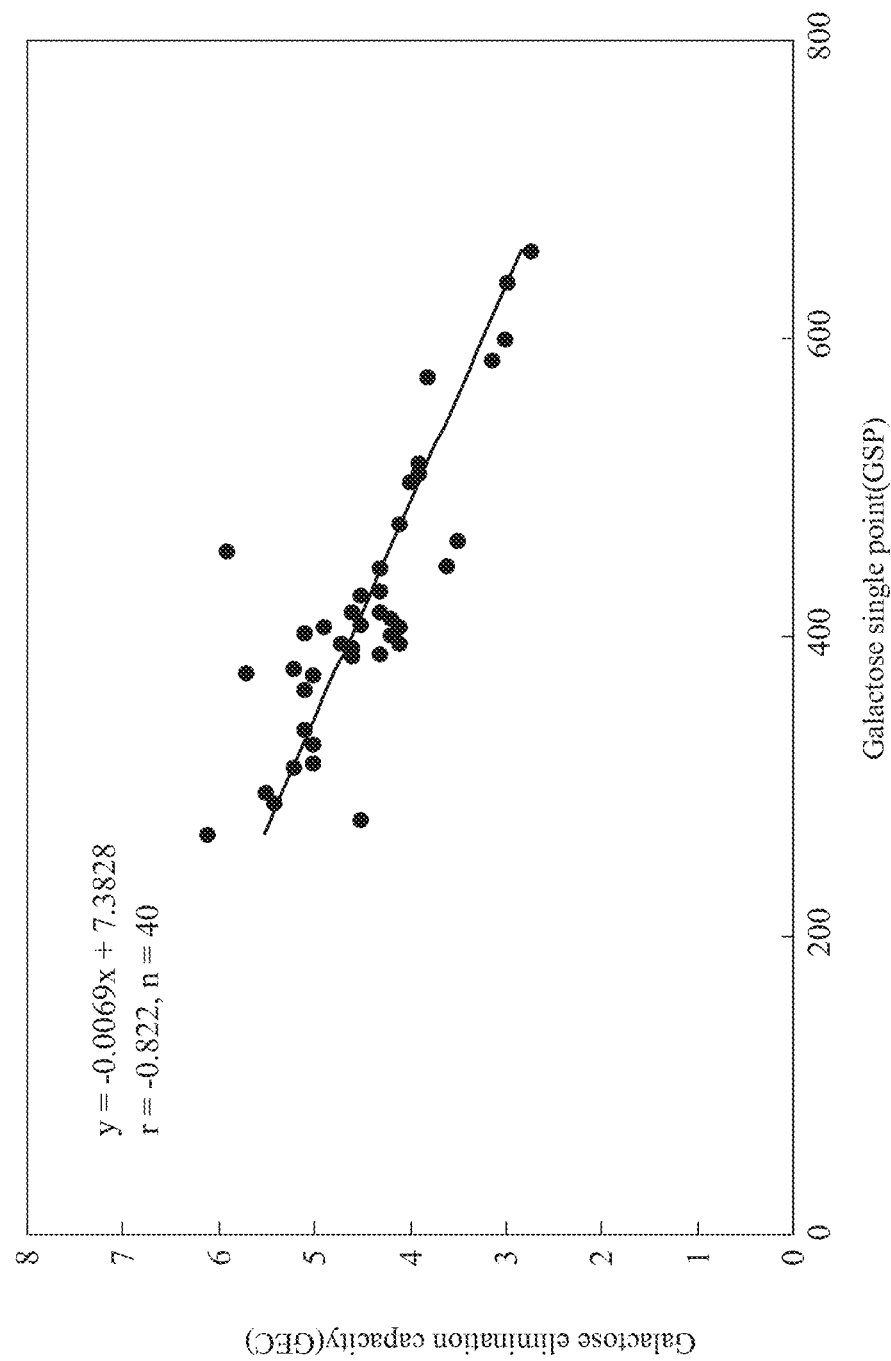

FIG. 10 is the statistical analysis results and demonstrated that GSP test values highly correlate with GEC test values in rats treated with control, INH, BNPP-INH, DSF-INH and BNPP-DSF-INH.

Figure 11:
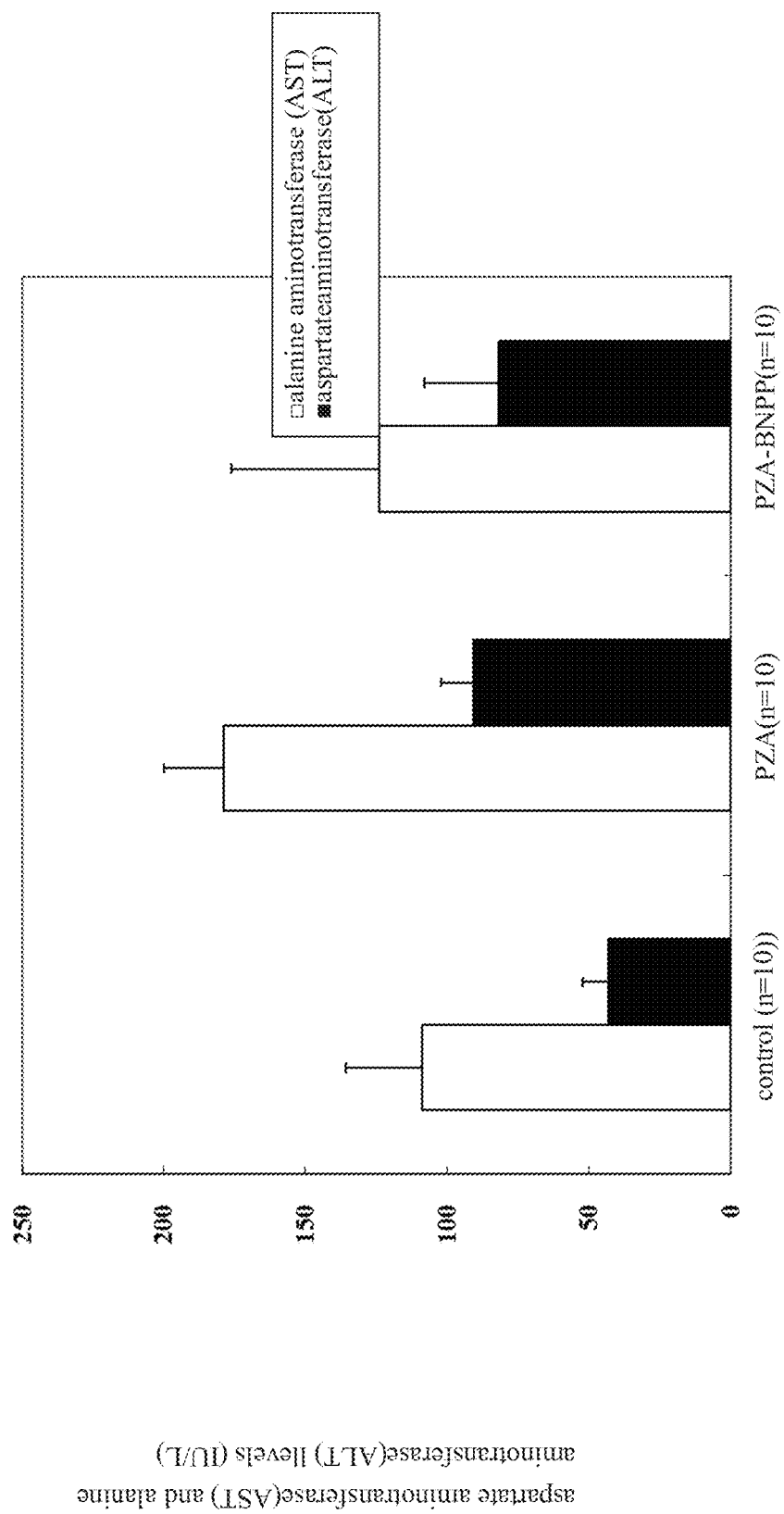

FIG. 11 shows the activities of AST and ALT in rats treated with control, PZA, BNPP-PZA or BNPP. Values represent the mean±SD, * indicates significant difference was observed between experimental and control groups, P<0.05.

Figure 12:
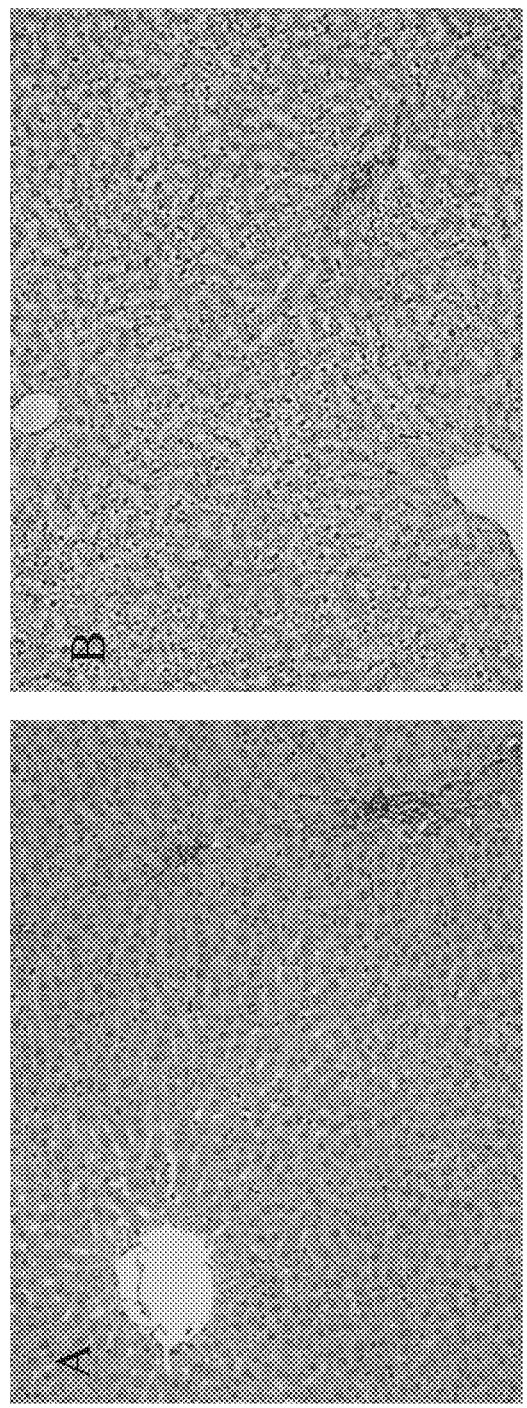

FIG. 12 shows the H&E staining of liver sections of rats treated with control, PZA, BNPP-PZA, or BNPP. FIG. 12A shows the normal hepatic tissue from control group (H&E staining, 400×), FIG. 12B shows central portal vein (V) hepatocyte damage and vacuolization (H&E staining, 400×).

Figure 13:
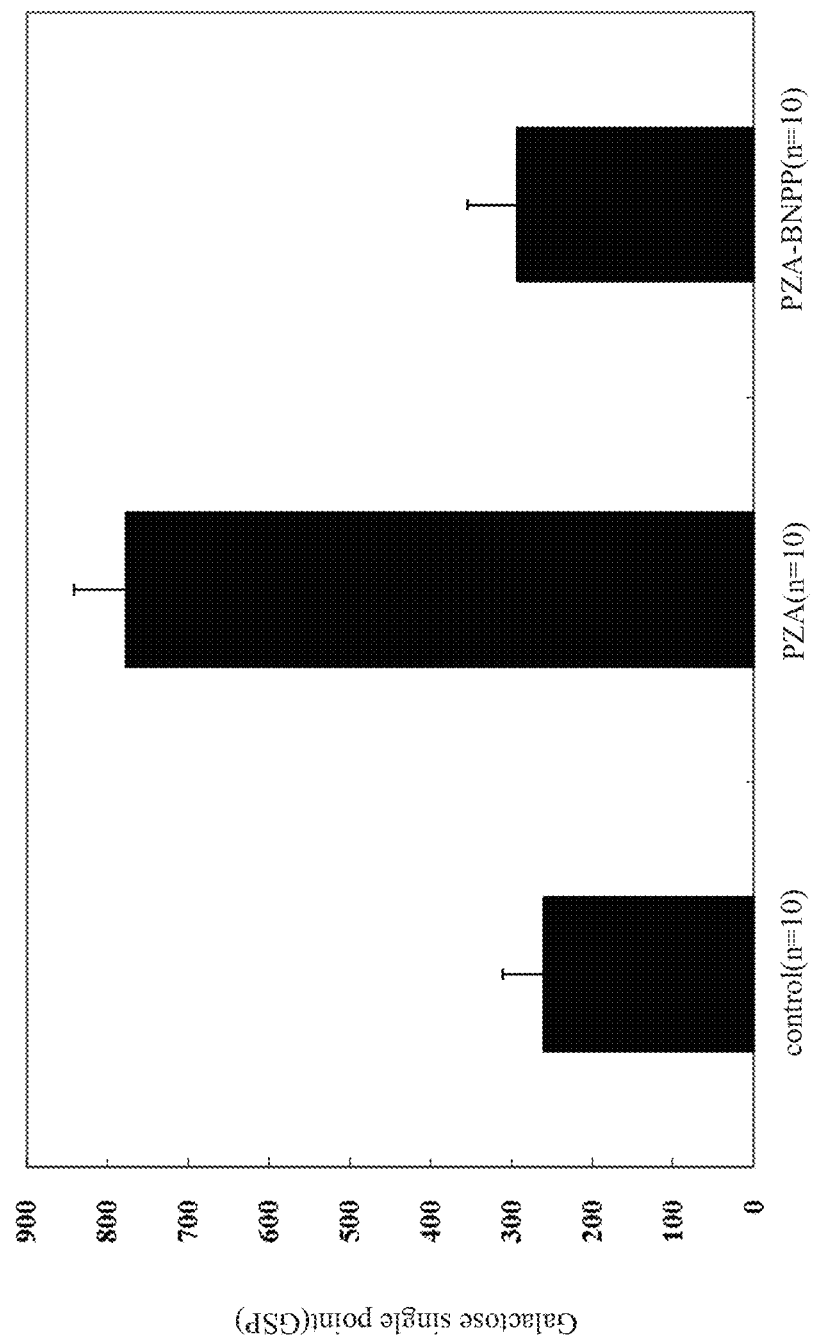

FIG. 13 shows the GSP values of rats treated with control, PZA, BNPP-PZA and BNPP. Values represent the mean±SD.

Figure 14:
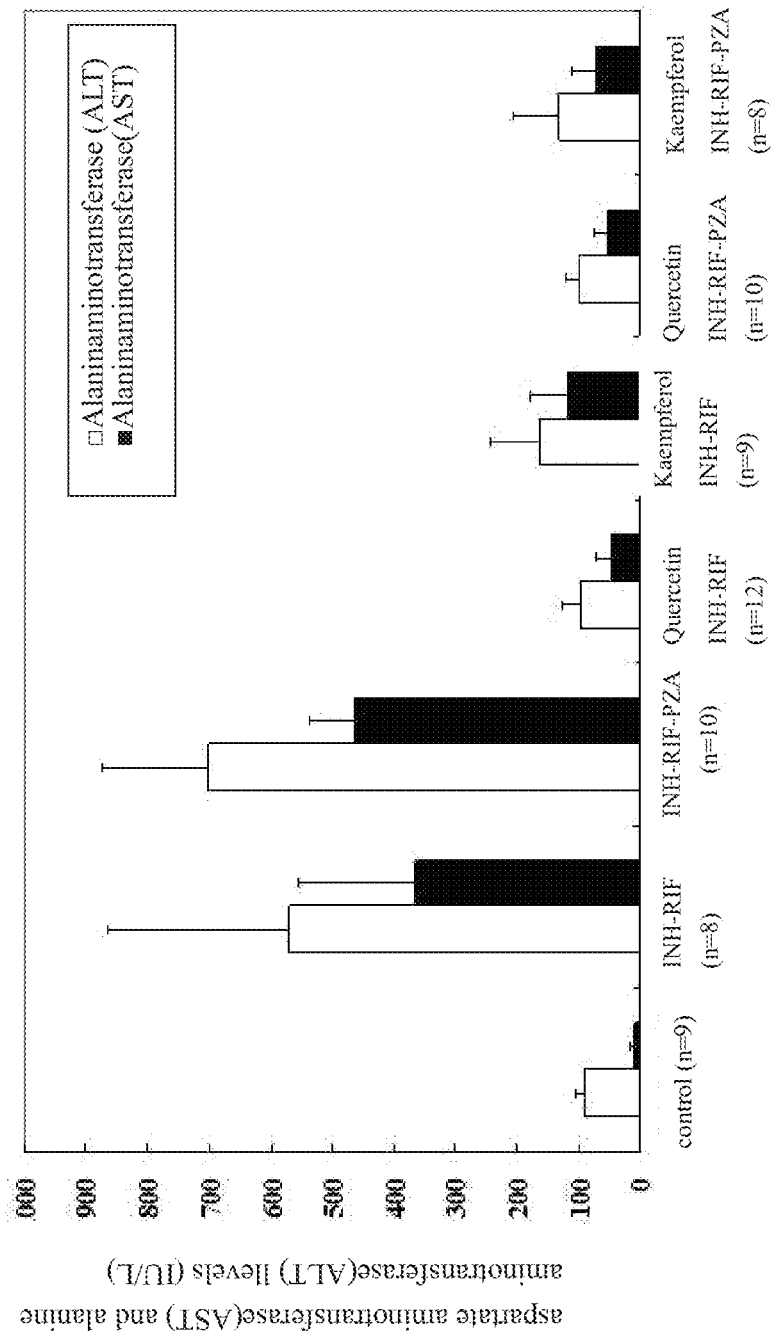

FIG. 14 shows the activities of AST and ALT in rats treated with control, INH-RIF, INH-RIF-PZA, Kaempferol-INH-RIF, Quercetin-INH-RIF, Kaempferol-INH-RIF-PZA or Quercetin-INH-RIF-PZA. Values represent the mean±SD, * indicates significant difference was observed between experimental and control groups, P<0.05.

Figure 15:
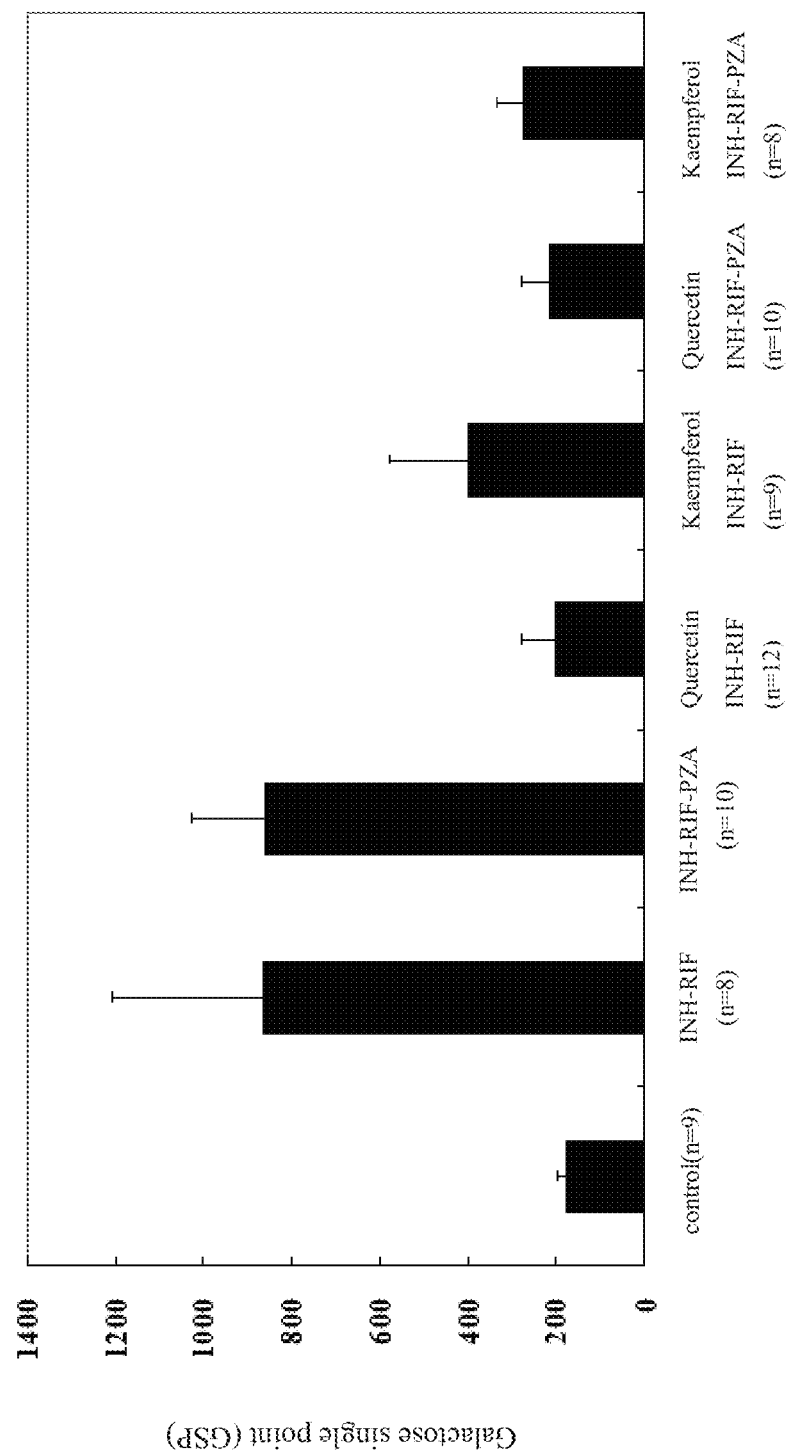

FIG. 15 shows the GSP values of rats treated with control, INH-RIF, INH-RIF-PZA, Kaempferol-INH-RIF, Quercetin-INH-RIF, Kaempferol-INH-RIF-PZA or Quercetin-INH-RIF-PZA. Values represent the mean±SD.

Figure 16:
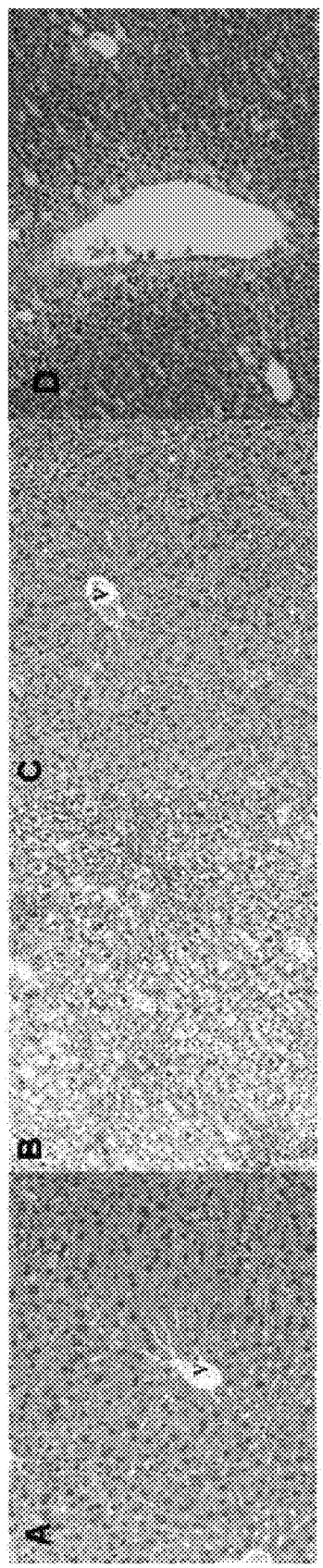

FIG. 16 shows the H&E staining results of liver sections of rats treated with control (A), INH-RIF-PZA (B), Quercetin-INH-RIF-PZA (C) or Kaempferol-INH-RIF-PZA (D).

Figure 17:
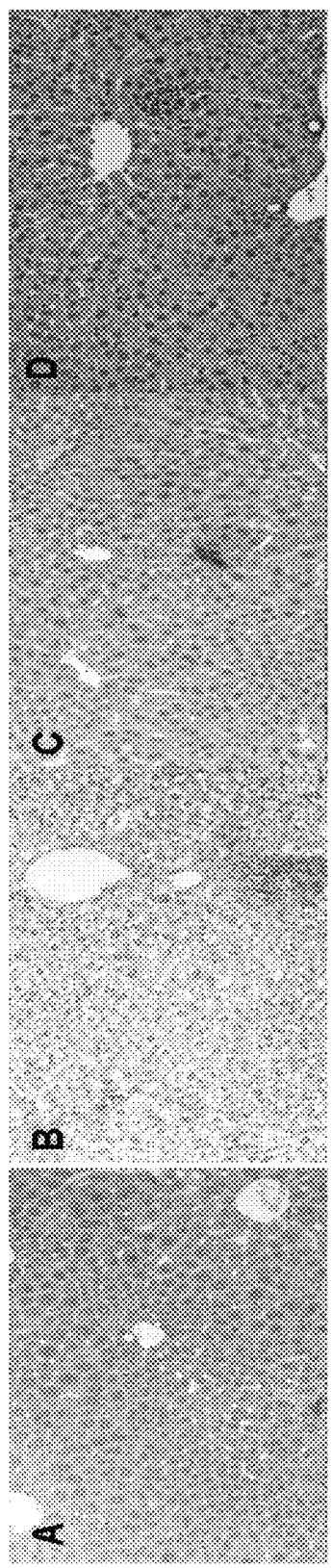

FIG. 17 shows the H&E staining results of liver sections of rats treated with control (A), INH-RIF (B), Quercetin-INH-RIF (C) or Kaempferol-INH-RIF (D).

Figure 18:
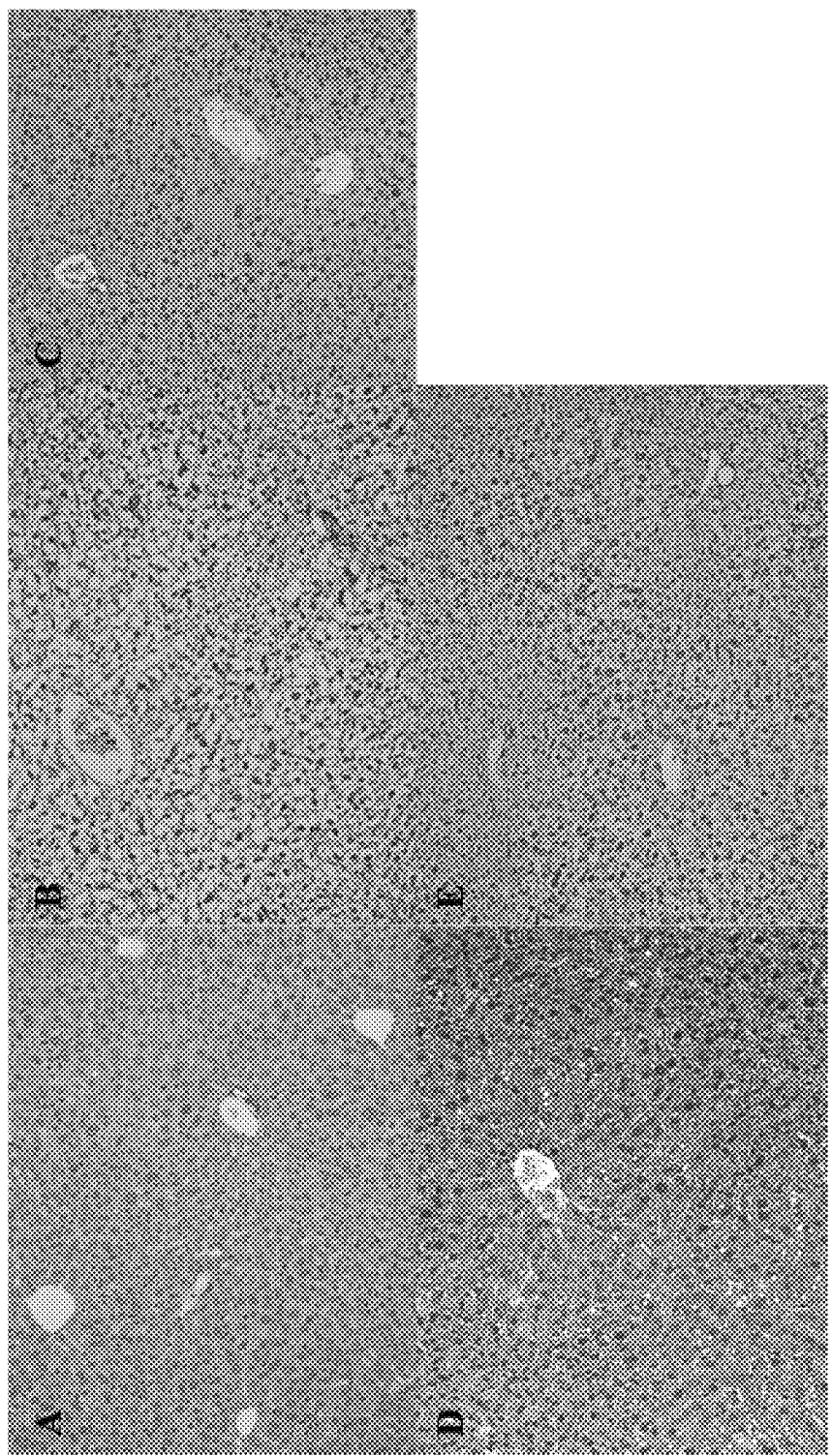

FIG. 18 shows the H&E staining results of liver sections of rats treated with control (A), INH-RIF (B), MH-INH-RIF (C) or MM-INH-RIF (D) or ML-INH-RIF (E).

Figure 19:
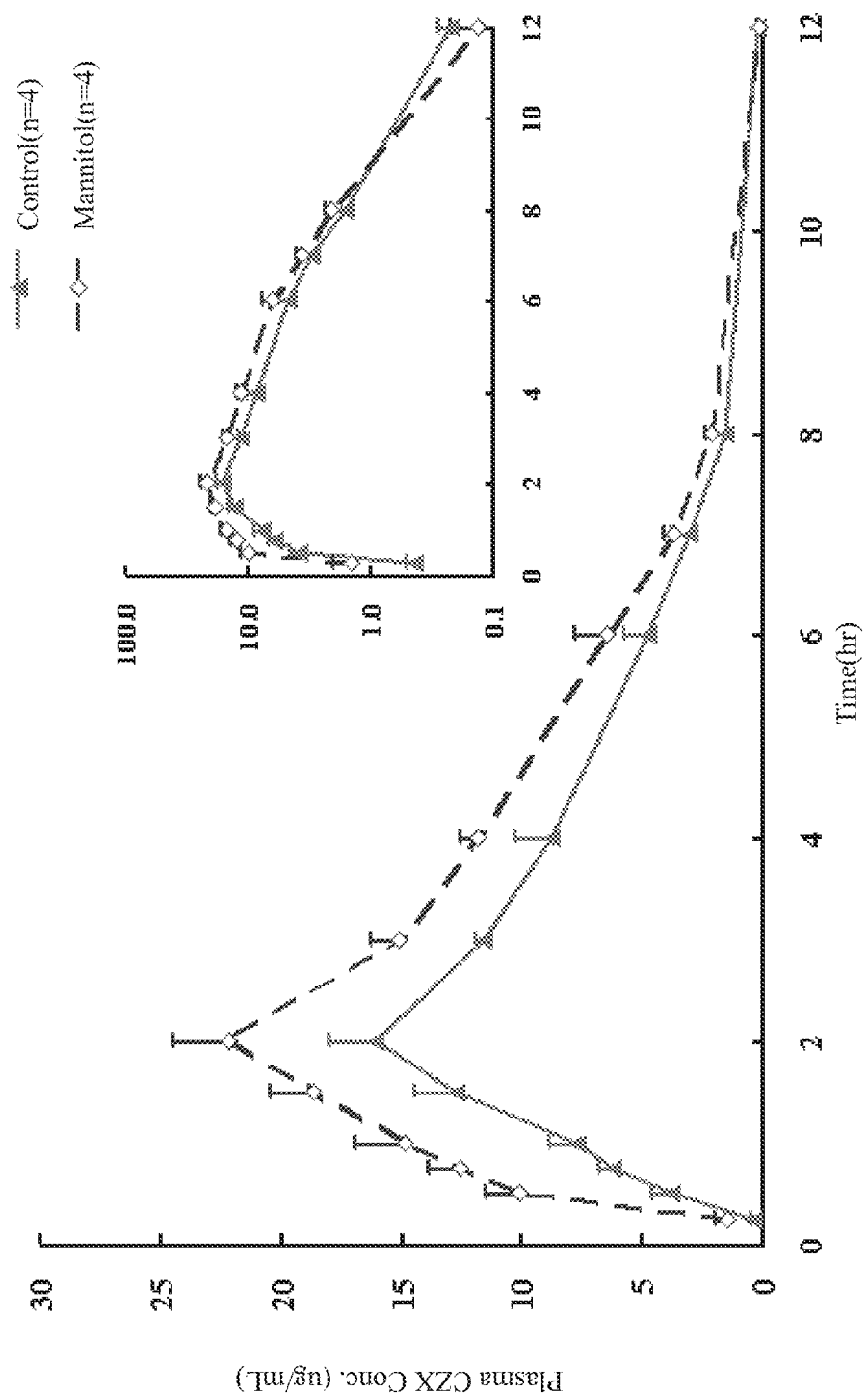

FIG. 19 shows the serum concentrations of Chlorzoxazone in healthy subjects treated with Chlorzoxazone+Rifamate and in the presence or absence of Mannitol; solid box indicates Rifamate control group that received Chlorzoxazone (500 mg)+Rifamate (INH/RIF 150/300 mg); hollow circle indicates HUCHE033 group that received Chlorzoxazone (500 mg)+Rifamate (INH/RIF 150/300 mg)+Mannitol (100 mg).

Figure 20:
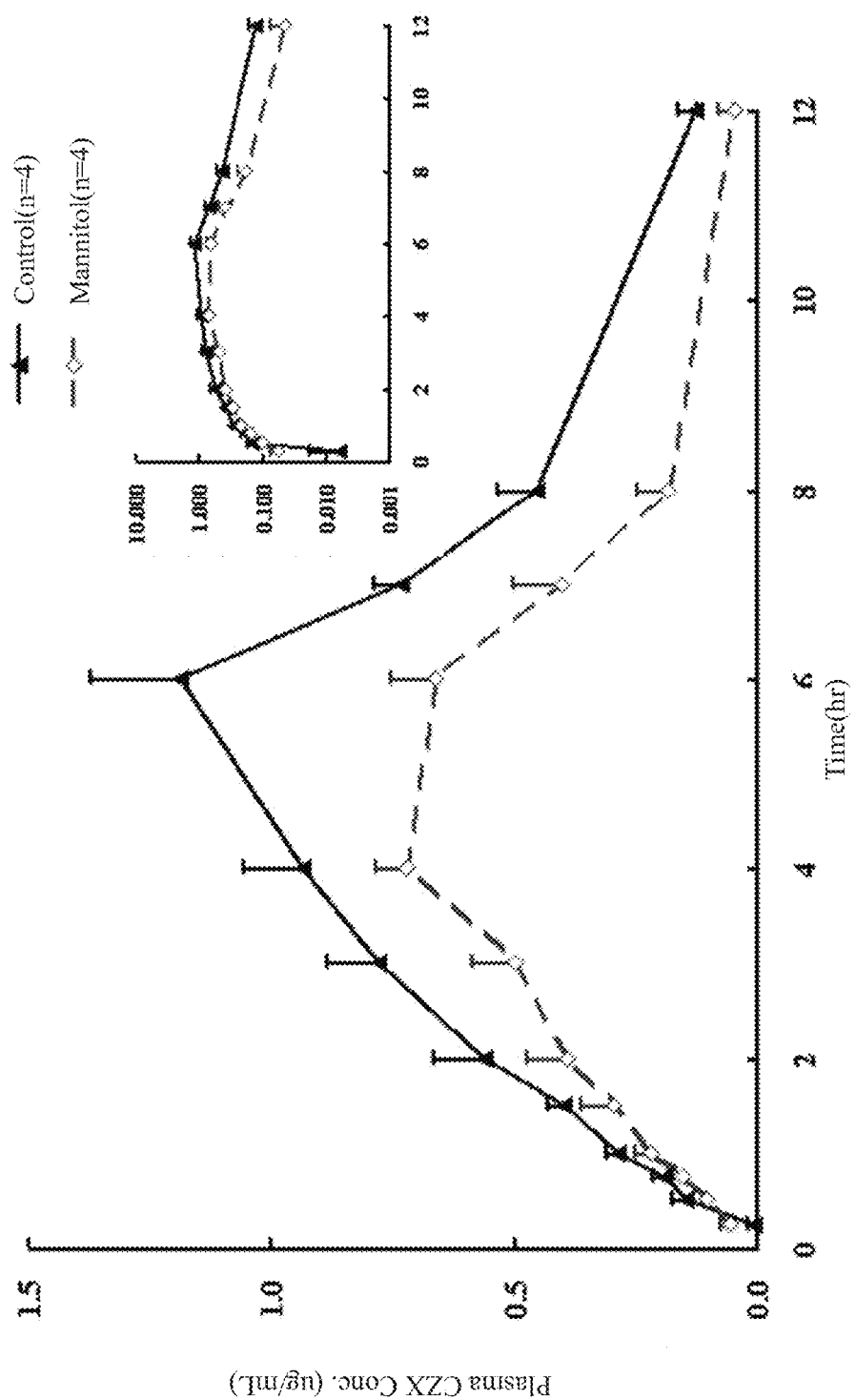

FIG. 20 shows the serum concentrations of 6-OH-Chlorzoxazone in healthy subjects treated with Chlorzoxazone+Rifamate and in the presence or absence of Mannitol; solid box indicates Rifamate control group that received Chlorzoxazone (500 mg)+Rifamate (INH/RIF 150/300 mg); hollow circle indicates HUCHE033 group that received Chlorzoxazone (500 mg)+Rifamate (INH/RIF 150/300 mg)+Mannitol (100 mg).

EXAMPLES

The present invention will now be described more specifically with reference to the following embodiments, which are provided for the purpose of demonstration rather than limitation.

Example 1

Animal Study of INH Treatment Combined with the CYP2E1 Inhibitor, Disulfuram (DSF) and/or Bis-p-Nitrophenyl Phosphate (BNPP)

1. Materials and Methods

All organic solvents are HPLC grade and purchased from Tedia (Fairfield, Ohio, USA) and corn oils were purchased from Sigma (St. Louis, Mo., USA). 8-iso-$PGF_{2\alpha}$ and radioactive 8-iso-$PGF_{2\alpha}$ were obtained from Cayman (Ann Arbor, Mich., USA). Galactose injection solution was prepared by South Photochemical Pharmaceutical Co., Ltd by dissolving 400 g of Galactose in 1 L isotonic buffering distilled water.

2. Animals

Male SD (Sprague-Dawley) rats weighing 320 to 350 g were purchased from National Laboratory Animal Center (Taiwan) and study was performed according to the animal study guidance published by Nation Health Research Institute (NHRI). Throughout the experiment, the rats were housed in air-conditioned and temperature-adjusted cages with a 12-h light/dark cycle and free access to water and food. The body weight of the rats was monitored throughout the experiment. Rats were anesthetized with sodium pentobarbital intraperitoneally (i.p.) at the dose of 50 mg/kg and Galactose was injected intravenously through a polyethylene catheter positioned in internal jugular vein. The catheter was positioned by cut-down technique and its end was embedded under the skin behind the neck. After the surgery, the rats were fasted overnight during the recovery period (about 16 hours) with unrestricted water access.

3. Experimental Procedures

Animals were randomized into one of five groups, each involving three treatments. The first treatment involved either a BNPP injection of 25 mg/kg or a BNPP vehicle (VEH1) injection (saline). BNPP was dissolved in saline (0.9% NaCl) after heating to approximately to 60° C., and after cooling, intraperitoneally (i.p.) injected at a volume of 1 mg/kg. The second treatment involved injections of either 100 mg/kg DSF or DSF vehicle (VEH2, corn oil). DSF was dissolved in corn oil and i.p. injected at a volume of 1 mg/kg. The third treatment involved injections of INH (25 mg/kg) or INH vehicle (VEH3, saline). INH was dissolved in saline (0.9% NaCl), and i.p. injected at a volume of 1 mg/kg. The first treatment (BNPP or VEH1) was administered 30 minutes before the third treatment (INH or VEH3), and the second treatment (DSF or VEH2) was administered 15 minutes before the third treatment (INH or VEH3).

The five treatment groups are:

Normal control group (NC, n=12): continuously injections of VEH1, VEH2 and VEH3 intraperitoneally once every day for 21 days;

INH group (INH, n=7): continuously injections of INH, VEH1 and VEH2 intraperitoneally once every day for 21 days;

BNPP-INH group (BNPP-INH, n=7): continuously injections of BNPP, INH and VEH2 intraperitoneally once every day for 21 days;

DSF-INH group (DSF-INH, n=7): continuously injections of DSF, INH and VEH1 intraperitoneally once every day for 21 days;

BNPP-DSF-INH group (BNPP-DSF-INH, n=7): continuously injections of BNPP DSH and INH intraperitoneally once every day for 21 days;

Galactose elimination capacity (GEC) test was performed 16 hours after the rats were sacrificed at the end of 21 days-treatment to measure the liver function.

4. Blood Sampling

After 21 days treatment, the rats were sacrificed with ether and blood samples collected in test tubes containing EDTA by dorsal aorta extract. The blood samples were centrifuged at 13,000 g for 15 min at 4° C. and plasma was aliquot into eppendorf tubes and stored at −80° C.

5. Biochemical Analysis

Hepatocellular damage was quantified by measuring both peak plasma Aspartate aminotransferase (AST) and Alanine aminotransferase (ALT) activities. AST and ALT activities are the most common biomarkers for hepatotoxicity and were measured by Synchron LXi 725 system (Beckman Instruments, USA).

6. Light Microscopy and Electron Microscopy

After the rats were sacrificed, the livers were subjected to histology analysis. Liver samples were fixed with 10% phosphate-buffered formalin and then, dehydrated and embedded in paraffin. Tissue was sectioned at 5 mm thick and stained with hematoxylin and eosin and Periodic acid Schiff stain (PAS) simultaneously, and results were observed under a light microscope. In addition, liver sections were washed with 0.1M cacodylate buffer (pH 7.4) and then fixed with 20% aqueous osmium tetroxide for 1 hour. Dehydrated and embedded in Spurr resin, and ultra-thin sections were obtained by using a diamond blade and double-stained with uranyl acetate and lead citrate, and sections were further examined under a Transmission Electron Microscope, Hitachi 600 (Hitachi Co., Japan).

7. Extraction and Quantification of 8-Iso-PGF2α

All isomers of $PGF_{2\alpha}$ were dissolved or diluted in adequate amount of ethanol and after aliquot, stored at −70° C. As an internal standard, 10 ng of 8-iso-$PGF_{2\alpha}$-$d_4$ was mixed with 0.5 ml of plasma in a glass tube and was then purified by a C18 Solid-Phase Extraction column (J. T. Baker, MA, USA). Sample eluants were evaporated under a stream of nitrogen and re-dissolved in 50 µl acetonitrile:water (15:85 v/v) solution followed by vortex for 30 seconds and 10 µl extract was further analyzed with a LC/MS/MS system.

8. Liquid Chromatography Mass Spectrometry (LC/MS/MS) Analysis

The HPLC system used includes two Shimadzu LC-10ADvP pumps, one

Shimadzu system control and one Shimadzu autosampler (Shimadzu, Japan). HPLC purification of the extract by C18 column (mesh size 5-µm, diameter 50×2.1 mm) using 2 mM ammonium acetate/acetonitrile, ACN gradient as mobile phase (t=0 mM, 15% ACN; t=6 mM, 70% ACN; t=7 mM, 90% ACN; t=8 mM, 90% ACN; t=8.5 min, 15% ACN). The flow rate of LC/MS/MS was maintained at 200 µl/min and the total time of purification was 13.5 minutes. Such HPLC system was connected to a triple stage quadrupole mass spectrometer (API3000, Applied Biosystem, Foster City, Calif., USA) and is equipped with a Turbo Ion Spray ionization source, and uses negative electrospray for ionization. Such spectrophotometer uses diffusion of standard solution of 200 ng/ml 8-iso-PGF2α or 8-iso-PGF2α-d4 to optimize the mode for multiple reaction monitoring (MRM). Ion pairs, m/z 353/193 and m/z 357/197, were used to monitor 8-iso-PGF2α and 8-iso-PGF2α-d4, respectively.

After quantification, linear calibration curve was constructed by plotting 6 8-iso-PGF2α concentrations (C) and area (Y) of 8-iso-PGF2α to 8-iso-PGF2α-d4 ratio, and the obtained correlation coefficient (r) is 0.999. Plasma 8-iso-PGF2α linearity range from 0.1 to 2.5 ng/ml and its regression equation is Y=−0.0517C+0.823 ng/ml. The measured results were calculated using deuterated 8-iso-PGF2α as internal control, and inter-batch precision and accuracy of the standard curve were evaluated by Back-Calculation on 6 individual measurements of internal control samples and the relative errors range from 5.06% to 3.13%.

9. Quantitative Tests of Liver Function

All rats were subjected to GSP and GEC tests. Galactose was injected intravenously within 30 seconds (0.4 g/ml, 0.5 g/kg BW) and blood samples were collected once at 5, 10, 15, 30, 45 and 60 minutes post injection by tail vein puncture. The amount of galactose was measured by the concentration of colorimetric galactose dehydrogenase and the tested concentrations ranged from 50 to 1,000p g/ml. The within-day variation of each concentration was calculated by percentage of standard deviation and coefficient of variation (CV). Day to day variation was determined by examining the slopes and the intercepts of the calibration curves and GEC was calculated by the following equation, and said equation was modified from Tygstrup's equation (Tygstrup N. The Galactose Elimination Capacity in Control Subjects and in Patients with Cirrhosis of the Liver. 1964. Acta Med. Scand 175: 281-289).

$$GEC = \frac{D}{T_{C=0} + 7} \text{ (mg/kg·min)}$$

D is the injection volume of galactose; $T_{c=0}$ is the time required for galactose to reach concentration of 0 and was obtained from blood concentrations-time curve linear regression 20 to 60 min post injection (usually at 2.22 mmol/L); 7 is the correction value of in vivo uneven distribution amended in accordance with rules of thumb; and GSP value was the blood concentration of galactose 60 min after the 30-second injection.

10. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is $P<0.05$.

Results

1. Biochemical Analysis

Figure 1:
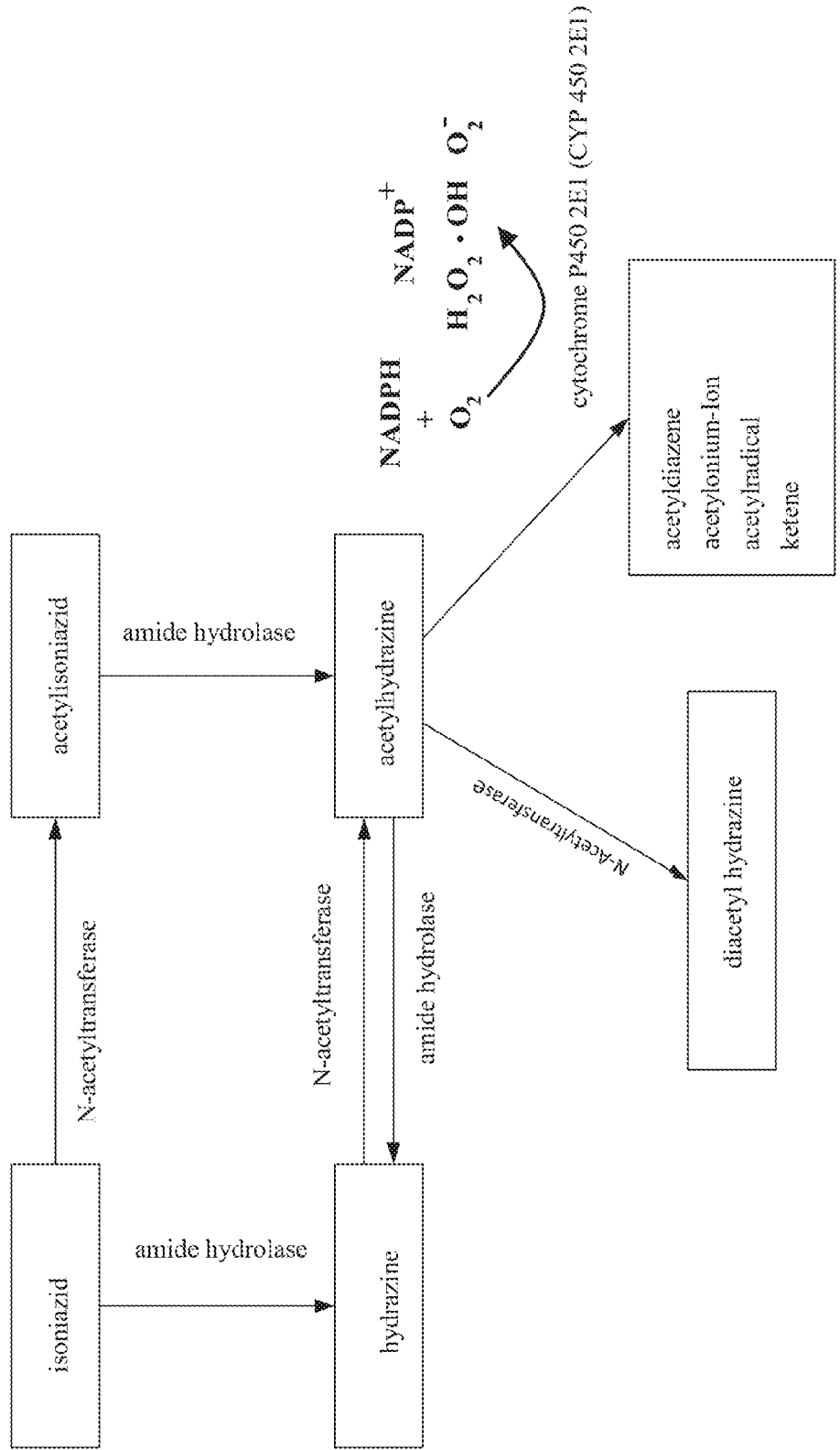
FIG. 1 shows the major pathways of isoniazid (INH) metabolism in liver.
Figure 2:
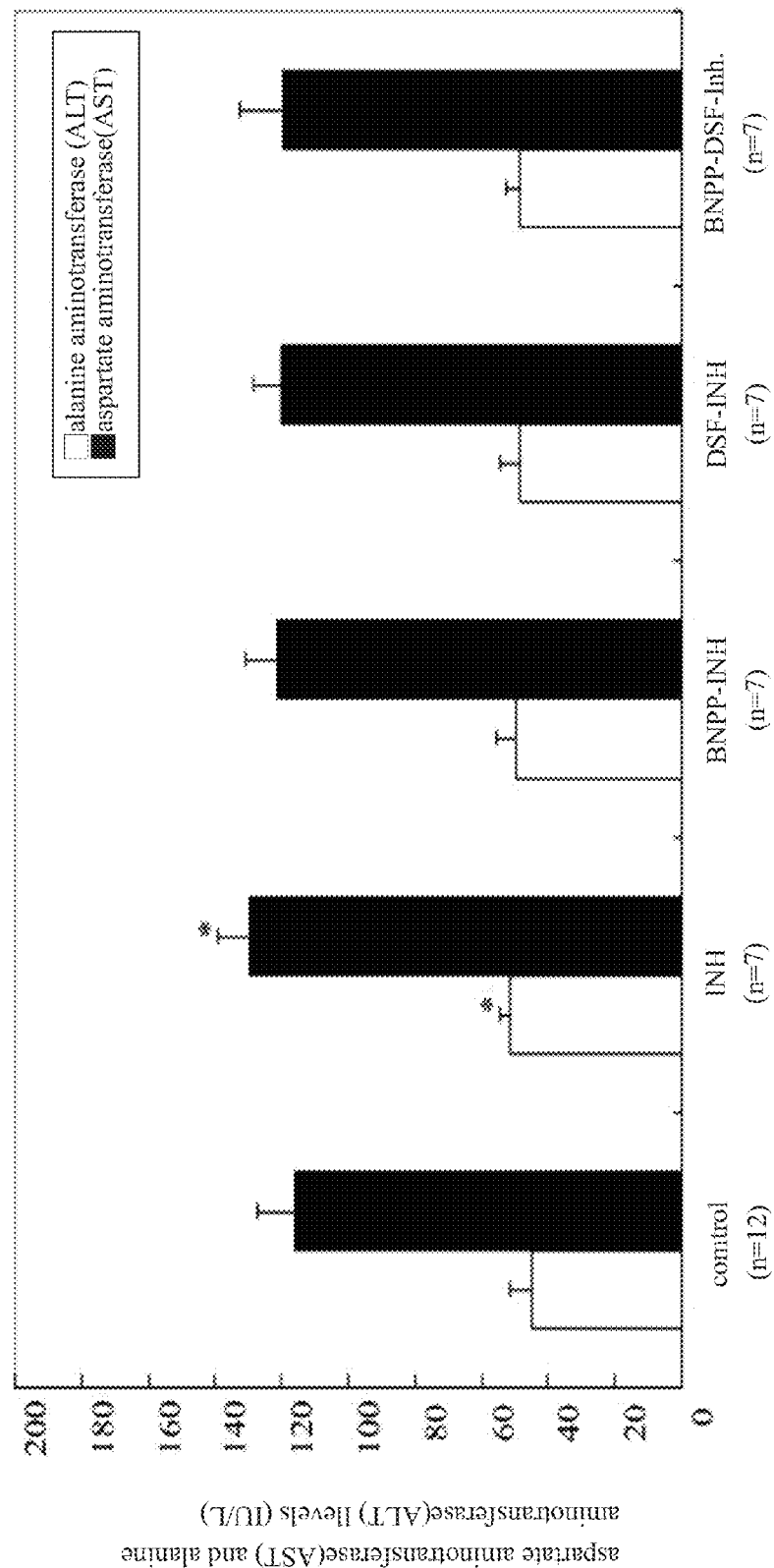
FIG. 2 shows the activities of AST and ALT in rats treated with control, INH, BNPP-INH, DSF-INH or BDPP-DSF-INH. Values represent the mean±SD, * indicates significant difference was observed between experimental and control groups, P<0.05.

At the end of the study, no significant differences was found between experimental and control animal groups in their body weight and relative liver weight. Biochemical analysis as shown in FIG. 2, peak plasma AST and ALT activities were significantly increased above control levels only in the INH group (the plasma AST activities were 116±11 IU/L and 129±10 IU/L in the control and the INH groups, respectively, ($p<0.05$); and the plasma ALT activities were 44±6 IU/L and 52±3 IU/L in the control and the INH groups, respectively, ($p<0.05$)) which demonstrated that biochemical hepatocellular injury was induced in the INH group whereas the concentrations of plasma aminotransferases in the control, BNPP-INH and BNPP-DSF-INH groups remained normal.

2. Histopathology

After daily i.p. injections of 150 mg/kg for three weeks, rats in the INH group showed hepatocellular damage. In contrary, liver structure remained normal in the control group. As shown in FIG. 3, hepatocytes in liver parenchyma from the control group were arranged inside of mesh plate in the radiation from the centrilobular portal vein, and hepatic sinusoids were found between two anastomosing plates. Liver sections from the INH group were shown in FIG. 3B, and hepatocytes surrounding the portal vein were fragmented and shown vacuolization. However, no hepatic necrosis was observed from the EM results. Comparison of the control group and the INH group (as shown in FIG. 3) indicated that hepatocytes rough endoplasmic reticulum (rER) from the INH group increased significantly. Previous studies have indicated that INH is a potent cytochrome P450 2E1 (CYP2E1) inducer (Ryan D E, Ramanathan L, Iida S, Thomas P E, Haniu M, Shively J E, Lieber C S, et al. Characterization of a major form of rat hepatic microsomal cytochrome P-450 induced by isoniazid. 1985. J. Biol. Chem. 260: 6385-6393), and CYP2E1 can cause the production of superoxide and hydroxyl radicals (Ekstrom G, Ingelman-Sundberg M. Rat liver microsomal NADPH-supported oxidase activity and lipid peroxidation dependent on ethanol-inducible cytochrome P-450 (P-450IIE1). 1989. Biochem. Pharmacol. 38: 1313-1319) and can increase ER function (Sodhi C P, Rana S V, Mehta S K, Vaiphei K, Attri S, Thakur S, Mehta S. Study of oxidative stress in isoniazid-induced hepatic injury in young rats with and without protein-energy malnutrition. 1996. J Biochem Toxicol. 11: 139-146.). Therefore, current results is consistent with prior research and liver injury in other tested groups including BNPP-INH, DSF-INH, and BNPP-DSF-INH showed no significant differences in compared with the control group (data not shown).

3. Quantification of 8-Iso-PGF2α from the Blood Samples

Under the mode of electrospray ionization, the maximum mass-to charge ratios of 8-iso-PGF$_{2\alpha}$ and 8-iso-PGF$_{2\alpha}$-d$_4$ are (m/z) 353 and (m/z) 357 ions, respectively. These negative charged ions were produced after numerous collisions and the molecular structures and mass spectrum of these two target compounds were shown in FIG. 4. In addition to the fact that the daughter ions of 8-iso-PGF$_{2\alpha}$-d$_4$ is four times higher than 8-iso-PGF$_{2\alpha}$'s, fragmentation patterns are very similar between 8-iso-PGF$_{2\alpha}$ and 8-iso-PGF$_{2\alpha}$-d$_4$ which indicated that most stable daughter ions were produced from A chain, and four deuterium atoms were labeled on such A chain. The most intensive daughter ions of 8-iso-PGF$_{2\alpha}$ and 8-iso-PGF$_{2\alpha}$-d$_4$ are (m/z) 193 and (m/z) 197 ions. FIG. 5 shows the LC/MS/MS chromatograph of 100 pg 8-iso-PGF$_{2\alpha}$ and 250 pg/ml 8-iso-PGF$_{2\alpha}$-d$_4$ (standard internal control) and a typical blood sample using MRM (multiple reaction monitor) mode. After injection of 1 ng 8-iso-PGF$_{2\alpha}$-d$_4$ as internal control, such control and blood samples were both purified by SEP and further analyzed by LC/MS/MS as mentioned earlier.

4. Concentrations of Plasma 8-Iso-PGF2α

Plasma 8-iso-PGF$_{2\alpha}$ is an indicator for oxidative stress. As shown in FIG. 6, in compare with the control group, plasma 8-iso-PGF$_{2\alpha}$ increased significantly in the INH group (the plasma concentrations of 8-iso-PGF$_{2\alpha}$ in the INH and the control groups are 151±26 pg/ml and 110±15 pg/ml, respectively, p<0.001) and BNPP-INH, DSF-INH, and BNPP-DSF-INH groups all showed considerably reduction of INH-induced 8-iso-PGF$_{2\alpha}$ (the plasma concentrations of 8-iso-PGF$_{2\alpha}$ in the BNPP-INH, DSF-INH, and BNPP-DSF-INH groups are 128±29 pg/ml, 126±20 pg/ml and 123±17 pg/ml) and plasma 8-iso-PGF$_{2\alpha}$ concentration in the INH group is 151±26 pg/ml, p<0.005. Interestingly, no significant differences were observed among the control, BNPP-INH, DSF-INH, and BNPP-DSF-INH groups. Moreover, INH combined with either BNPP or DSF did not further reduce the plasma concentration of 8-iso-PGF$_{2\alpha}$.

5. Residual Liver Function Test

As shown in FIG. 7, the GSP test values between the control group and the INH group are significantly different (GSP values of the control and INH groups are 384±69 μg/ml and 565±87 μg/ml, respectively). In addition, GSP values of the BNPP-INH, DSF-INH, and BNPP-DSF-INH groups are 401±70 μg/ml, 449±45 pg/ml, and 388±53 pg/ml. The BNPP-INH, DSF-INH, and BNPP-DSF-INH groups are an significantly different from the INH group (p<0.001, p<0.005, and p<0.001). Furthermore, GSP value was elevated considerably in the INH group, whereas groups treated with combination drugs of INH and BNPP, INH and DSF, or INH and BNPP-DSF can resist such increase. On the other hand, compare to the DSF-INH group, INH combined with BNPP and DSF can significantly reduce INH-induced hepatotoxicity, though no statistical difference was observed (p=0.1). Also, no statistical differences were found among the GSP values of the control, the BNPP and the BNPP-DSF groups.

Similar results were also observed in GEC tests. As shown in FIG. 8, GEC values are significantly reduced in the INH group compare to the control group (the GEC values of the INH and the control groups are 3.4±0.6 mg/min·kg and 4.9±0.8 mg/min·kg, p<0.001, respectively). Additionally, GEC values of the BNPP-INH, DSF-INH, and BNPP-DSF-INH groups are 4.5±0.6 mg/min·kg, 4.3±0.4 mg/min kg and 4.7±0.5 mg/min kg. An three groups exhibited significant differences from the INH group (p<0.005, p<0.05, and p<0.005). GEC values reduced noticeably in the INH group, whereas the combination of BNPP and INH; DSF and INH; and BNPP-DSF and INH can restore such reduction. Moreover, compare to DSF-INH group, INH combined with both BNPP and DSF tend to increase the GEC value (the GEC values of the DSF-INH and BNPP-DSF-INH groups are 4.3±0.4 mg/min kg and 4.7±0.5 mg/min·kg, respectively, p=0.29). In addition, no statistical differences were found among the GSP values of the control, the BNPP, the DSF, and the BNPP-DSF groups.

In order to confirm the concentrations of plasma AST, plasma ALT and plasma 8-iso-PGF$_{2\alpha}$ and to verify the correlation between quantitative tests for liver function (e.g. GSP and GEC tests), several analyses were performed and the results have suggested that the GSP values are highly correlate with plasma 8-iso-PGF$_{2\alpha}$ concentration (as shown in FIG. 9), the co-efficient is 0.836; the GSP values are highly correlate with the GEC values, (p<0.001), the co-efficient is—0.822; and finally, the GEC values are also highly correlate with plasma 8-iso-PGF$_{2\alpha}$ concentration, the co-efficient is −0.743 (p<0.001). On the other hand, GSP values, GEC values and plasma 8-iso-PGF$_{2\alpha}$ concentration are not correlated with either AST or ALT concentrations (as shown in table 1).

TABLE 1

Correlations between biochemical analysis and GSP, GEC and 8-iso-PGF$_{2\alpha}$

| | GSP | GEC | 8-iso-PGF2α |
|---|---|---|---|
| AST | r = 0.114 | r = −0.111 | r = 0.217 |
| ALT | r = 0.016 | r = 0.039 | r = 0.035 |
| 8-iso-PGF2α | r = 0.836* | r = −0.743* | r = 1* |

Statistically analyzed by Pearson's correlation coefficient
*p < 0.00

Example 2

Screening of Cytochrome P450 2E1 (CYP2E1) Inhibitors-cDNA Synthesized Microsomal Cytochrome P450 2E1 (CYP2E1)

1. Materials and methods

CYP2E1 High Throughput Inhibitor Screening Kit (BD Bioscience, USA) was used to screen the cytochrome P450 (CYP2E1) inhibitors from 22 Chinese medicine guiding drugs and 10 excipients and microsomal cytochrome P450 (CYP2E1) was synthesized from cDNA (BD Bioscience, USA). The principle of the screening kit is to measure the percentage of CYP2E inhibition, after adding the test sample to substrate MFC (7-Methoxy-4-trifluoromethyl coumarin) and cytochrome P450 (CYP2E1), by measuring the synthesis of standard CYP2E1 metabolite (HFC, 7-Hydroxy-4-trifluoromethyl coumarin) and use control HFC as baseline.

All test samples were dissolved in acentoitrile and tested for their effects on inhibition of CYP2E1 at different concentrations: Chinese medicine guiding drugs (66 μM, 33 μM, 16.5 μM) and excipients (0.167%, 0.08%, 0.042%, w/v). The tested results of Chinese herbs and excipients were listed in FIG. 3 and FIG. 4, respectively.

The materials used for CYP2E1 High Throughput Inhibitor Screening Kit included:
(1) CYP2E1+P450 Reductase+Cytochrome b5: 100 mM potassium phosphate (pH 7.4) with 1.3 nmol P450 and p-Nitrophenol dehydrogenase.
(2) Control proteins: 15 mg/mL control protein was dissolved in 100 mM potassium (pH7.4).

(3) Buffer solution: 0.5M potassium phosphate (pH 7.4).
(4) Stop solution: 0.5 M Tris Base.
(5) Cofactors: contains 1.3 mM NADP$^+$, 66 mM MgCl$_2$ and 66 mM Glucose 6-Phosphate.
(6) Glucose 6-Phosphate dehydrogenase: 40 units/ml in 5 mM Sodium Citrate Buffer (pH 7.5).
(7) MCF (7-Methoxy-4-trifluoromethyl coumarin), a fluorescence substrate, was dissolved in 50 mM acetonitrile.
(8) DDTC (Diethyldithiocarbamic acid): a CYP2E1 selective inhibitor (experimental group), 20 mM DDTC was dissolved in acentoitrile.
(9) HFC (7-Hydroxy-4-trifluoromethyl coumarin): a CYP2E1 metabolite standard, 0.25 mM HFC was dissolved in 0.1M Tris (pH 9.0).
(10) NADPH-Cofactor Mix: 187.5 µl cofactors, 150 µl G6PDH (glucose 6-Phosphate dehydrogenase solution) and 100 µl control protein in 14.56 µl sterilized water.
(11) Cofactor/acentonitrile mix: 66 µl acentonitrile was added into 9.93 ml NADPH-cofactor mix.
(12) Enzyme/Substrate Mix: 5.94 ml sterilized water, 50 µl HTS-706 (CYP2E1, 2 nM P450 content), and 28 µl 50 mM MFC (7-Methoxy-4-trifluoromethyl coumarin (fluorescence substrate) were added to 5.94 ml sterilized water.

Selection of Cytochrome P450 2E1 (CYP2E1) Inhibitors

The procedures of selection of cytochrome P450 2E1 (CYP2E1) inhibitors from Chinese medicine guiding drugs and excipients using the CYP2E1 High Throughput Inhibitor Screening Kit (BD Bioscience, USA) are:

Preparation of Controls:
a. 149 µl NADPH-Cofactor Mix and 1 µl 20 mM DDTC were added to the #1 well in a 96-well plate and mixed thoroughly,
b. Add 100 µl Cofactor/acetonitrile mix to #2 to #12 wells, and well #1 to #8 are positive control. Well #9 and 10 are control and well #11 and #12 are blank,
c. Perform serial dilution from well #1 to #8 by transferring 50 µl from well #1 and transfer to well #2; after mixed thoroughly, transferring 50 µl from well #2 and transfer to well #3 and so on to well #8 and remove 50 µl from well #8 and the diluted concentrations are: 66.6, 22.2, 7.4, 2.47, 0.82, 0.27, 0.091 and 0.03 µM, 2. Preparation of Experimental Groups:
a. 149 µl NADPH-Cofactor Mix and 1 µl 20 mM Chinese medicine guiding drugs or 1 µl 25% (w/v) excipients were added to the well #1 and #2, respectively, in a 96-well plate and mixed thoroughly,
b. Transfer 50 µl from well #1 and #2 and added to well #3 and mixed thoroughly (triplicate for each sample), 3. Initiation and Termination of the Reaction:
a. The 96-well plate was incubated at 37° C. for 10 mM,
b. 100 µl of Enzyme/Substrate Mix was added to every well and mixed thoroughly except the blank wells,
c. The 96-well plate was incubated at 37° C. for 40 min,
d. 75 µl Stop Solution was added to every well and mixed thoroughly,
e. Immediately add 100 µl Enzyme/Substrate Mix to blank wells and mixed thoroughly,
f. Measure with a Fluoroskan Ascent FL (Thermo Electron Corporation, Finland) with excitation at 405 nm and emission at 538 nm, 4. The fluorescence was transverse into CYP 2E1 metabolite standard (HFC) concentration (pmol) and the percentage (%) of CYP 2E1 inhibition was calculated using control as baseline by following equation:

$$CYP\ 2E1\ inhibition(\%) = 1 - \frac{Sample\ HFC}{Control\ HFC}$$

Results

1. Positive Controls

CYP 2E1 inhibition of positive controls (DDTC) was shown in table 2 Inhibition of CYP 2E1 reached 97.555% when DDTC was at 66.6 µM concentration (that is 0.167%, w/v). This is the highest tested concentration for Chinese medicine guiding drugs, and 0.167% (w/v) is the highest tested concentration for excipients.

TABLE 2

Inhibition of CYP 2E1 (%) by positive controls

| DDTC concentration (µM) | HFC synthesis (pmol) | Inhibition of CYP 2E1 (%) |
|---|---|---|
| 0 (control) | 222.00 | 0 |
| 0.03 | 256.00 | — |
| 0.091 | 202.00 | 8.71 |
| 0.27 | 151.71 | 31.52 |
| 0.82 | 126.14 | 43.06 |
| 2.47 | 55.18 | 75.09 |
| 7.4 | 21.08 | 90.49 |
| 22.2 | 15.10 | 93.19 |
| 66.6 | 5.42 | 97.55 |

2. Inhibition of CYP 2E1 in Test Groups

The CYP 2E1 inhibition activity of various Chinese medicine guiding drugs was shown in FIG. 3 and different guiding drug shave different inhibition effects at various concentrations (66 µM, 33 µM, 16.5 µM). Among those tested guiding drugs, Nordihydroguaiaretic acid at 66 µM exhibited the best inhibition activity (97.99±0.66%).

TABLE 3

Inhibition of CYP 2E1 (%) by Chinese medicine guiding drugs

| Guiding drugs | Inhibition of CYP 2E1 (%) | | Minimum Effective Dose* (mg) |
|---|---|---|---|
| Tested concentration | 66 µM | 16.5 µM | |
| Control | 0 | 0 | — |
| Positive control (DDTC) | 97.55 ± 1.862 | — | — |
| Nordihydro-guaiaretic acid | 97.99 ± 0.66 | 76.52 ± 3.86 | 17 |
| (−)-Epigallo-cetechin-3-gallate | 97.56 ± 0.18 | 92.56 ± 0.46 | 25 |
| Capillarisin | 76.12 ± 1.89 | 49.05 ± 5.18 | 17 |
| Kaempferol | 70.63 ± 2.53 | 71.87 ± 1.14 | 16 |
| Phloretin | 66.84 ± 4.79 | 42.04 ± 3.63 | 15 |
| disulfiram | 66.54 ± 2.55 | 57.89 ± 3.91 | 17 |
| Hesperetin | 54.75 ± 1.37 | 32.10 ± 5.80 | 33 |
| 6-Gingerol | 51.89 ± 3.33 | 30.13 ± 2.67 | 16 |
| gallic acid | 48.24 ± 4.20 | 35.59 ± 10.03 | 9 |
| Isoliquritigenin | 47.83 ± 5.36 | 39.08 ± 2.75 | 18 |
| Narigenin | 41.84 ± 3.51 | 25.11 ± 7.60 | 9 |
| (+)-Taxifolin | 34.54 ± 3.47 | 22.58 ± 11.69 | 17 |
| Wongonin | 23.48 ± 2.59 | 15.64 ± 7.82 | 16 |
| Protocatechuic acid | 22.75 ± 4.07 | 25.66 ± 12.74 | 8 |
| (+)-Catechin | 16.45 ± 9.67 | 41.53 ± 7.62 | 16 |
| β-naphthoflavone | 15.40 ± 12.94 | 6.52 ± 6.64 | 15 |
| Embelin | 13.54 ± 11.64 | 5.95 ± 7.48 | 16 |
| trans-Cinnamic acid | 7.10 ± 6.95 | 5.71 ± 10.53 | 8 |
| (−)-Epicatechin | 2.57 ± 11.60 | 18.27 ± 9.34 | 16 |

Note: The "16.5 µM" column also shows an intermediate concentration column with values: 17, 25, 17, 16, 15, 17, 33, 16, 9, 18, 9, 17, 16, 8, 16, 15, 16, 8, 16 respectively.

TABLE 3-continued

Inhibition of CYP 2E1 (%) by Chinese medicine guiding drugs

| Guiding drugs | Inhibition of CYP 2E1 (%) | | | Minimum Effective Dose* (mg) |
|---|---|---|---|---|
| Tested concentration | 66 μM | | 16.5 μM | |
| Phloridzin | 1.42 ± 9.28 | 24 | 1.25 ± 7.90 | 24 |
| Puerarin | −12.86 ± 2.75 | 23 | 0.43 ± 2.31 | 23 |
| Umbelliferone | −1081.56 ± 168.00 | 9 | −280.41 ± 19.48 | 9 |

*Minimum Effective Dose: minimum tested concentration (mg/L) × the volume of human liver and intestine (3L)

The CYP 2E1 inhibition activity of various excipients was shown in FIG. 4. Different excipients have different inhibitory effects on cytochrome P450 under different conditions (0.167%, 0.08%, 0.042%, w/v) and among which 0.167% Brij 58 showed the best inhibition activity (97.75±0.66%).

TABLE 4

Inhibition of CYP 2E1(%) by excipients

| Chinese medicine guiding drugs | Inhibition of CYP2E1 (%) Tested concentration (w/v) | | | Minimum Effective Dose* (mg) |
|---|---|---|---|---|
| | 0.167% | 0.08% | 0.042% | |
| Control | 0 | | | — |
| Positive control (DDTC) | 97.55 ± 1.862 | | | — |
| Brij 58 | 97.75 ± 0.66 | 96.58 ± 0.40 | 96.02 ± 0.17 | 1260 |
| Brij 76 | 97.56 ± 1.02 | 96.87 ± 1.00 | 94.76 ± 0.47 | 1260 |
| Brij 35 | 93.33 ± 0.82 (Tested concentration 0.025%) | 89.45 ± 0.68 (Tested concentration 0.013%) | 76.21 ± 7.37 (Tested concentration 0.006%) | 180 |
| Tween 20 | 87.20 ± 1.29 | 82.80 ± 1.71 | 71.77 ± 4.48 | 1260 |
| Tween 80 | 73.92 ± 4.71 | 65.45 ± 2.50 | 64.02 ± 12.54 | 1260 |
| Tween 40 | 58.97 ± 3.29 | 47.05 ± 6.48 | 44.79 ± 2.49 | 1260 |
| PEG 2000 | 44.33 ± 2.75 | 40.13 ± 3.06 | 35.81 ± 3.26 | 1260 |
| PEG 400 | 42.33 ± 5.25 | 39.10 ± 0.73 | 31.98 ± 5.97 | 1260 |
| Pluornic F68 | 41.72 ± 5.34 | 42.98 ± 3.24 | 37.11 ± 10.35 | 1260 |
| PEG 4000 | 37.21 ± 1.91 | 41.22 ± 0.97 | 37.18 ± 10.52 | 1260 |

*Minimum Effective Dose: minimum tested concentration (mg/L) × the volume of human liver and intestine (3 L)

Example 3

Selection of Cytochrome P450 2E1 Inhibitors-Human Liver Microsomal Cytochrome P450 2E1

1. Materials and Methods

Materials

Microsomes prepared from human liver were used to extract cytochrome P450 2E1 (CYP2E1) and CYP2E1 inhibitors were screened from 39 Chinese medicine guiding drugs and 10 excipients. Chlorzoxazone hydroxylation is a reaction catalyzed primarily by CYP2E1 in liver. The extracted human liver microsomal cytochrome P450 2E1 (CYP2E1) was mixed with its substrate, Chlorzoxazone, and test sample was then added Inhibition of CYP2E1 activity was calculated by measuring CYP2E1 standard metabolite, 6-OH-CZX (6-Hydroxy-Chlorzoxazone), and compared with control 6-OH-CZX.

All test samples were dissolved in 10% methanol or distilled water and guiding drugs and excipients at various concentrations were tested for their effects on inhibition of CYP2E1 activity. Tested Chinese medicine guiding drugs and excipients are shown in FIG. 3 and FIG. 4, respectively.

The materials required for screening human hepatocyte cytochrome P450 (CYP2E1) inhibitors are:

1. CYP2E1: 100 mM potassium phosphate (pH 7.4) which contains 10 mg/ml P450 protein concentrate 2. Control protein: 10 mg/ml P450 protein in 100 mM potassium phosphate (pH 7.4)

3. Buffer solution: 0.5 M potassium phosphate (pH 7.4); stop solution: ice-acetonitrile 4. Cofactors: include 100 mM NADP and 10 mM Glucose 6-Phosphate 5. Glucose 6-Phosphate Dehydrogenase: 2000 units/ml in sterilized water 6. Chlorzoxazone: substrate, 16 mM Chlorzoxazone in 10% methanol 7. DDTC (Diethyldithiocarbamic acid): CYP2E1 selective inhibitor (positive control), 20 mM DDTC in 10% methanol 8. NADPH-regenerating System: add 530 μl Cofactor, 40 μl G6PDH (Glucose 6-Phosphate Dehydrogenase Solution) and 100 μl Control Protein to 3.42 ml 2. Screening of cytochrome P450 2E1 (CYP2E1) inhibitors Experimental procedures for screening cytochrome P450 2E1 (CYP2E1) inhibitors:

1.0. 1M potassium phosphate (pH 7.4) which contains 10 mg/ml P450 protein concentrate was mixed with 5 mM $MgCl_2$ and incubated at 4° C. water bath for 15 min, 2. After incubation, 16 mM Chlorzoxazone and test samples were added to experimental groups; methanol:sterilized water at 1:1 ratio was added to control groups and DDTC was added to positive control groups, 3. Finally, cofactor 1 mM $NADP^+$, 10 mM G6P and 2 IU G6PD were added and reaction mixtures were transferred to pre-incubation 37° C. water bath for 1 mM and activity was measured after 30 min of reaction 4. At the end of reaction, 500 μl acetonitrile was added to stop the reaction followed by 5 g/mL 4-hydroxy-tobutamide after 1 mM incubation. The mixture was then centrifuged and 20 L of supernatant was diluted ten times with methanol/sterilized water and 5 L was used for LC/MS/MS analysis.

5. Results: the measured signal values obtained from LC/MS/MS analysis were logarithmically-transformed to give the amounts of CYP2E1 standard metabolite, 6-Hydroxy-Chlorzoxazone (pmol), using the control group as baseline with inhibition set at 0%. The inhibition of CYP2E1 was then calculated by the following equation:

The amount of 6-OH-CZX in experimental $$\text{Inhibition of } CYP\ 2E1(\%) = 1 - \frac{\text{The amount of 6-OH-CZX in experimental group}}{\text{Control 6-OH-CZX}}$$

Results
1. Positive Control
The inhibition of CYP 2E1 of positive control, DDTC, is shown in table 2 and according to table 5, DDTC can inhibit up to 87.56% of CYP 2E1 activity at concentration 100 μM.

CYP 2E1 inhibition by excipients was shown in table 4 and indicated that different excipients have different effects on cytochrome P450 CYP 2E1 activity at various concentrations (0.167%, 0.08%, 0.042%, w/v) and 0.167% Brij 58 has the best inhibition of 91.24±1.33%.

TABLE 5

Inhibition of CYP 2E1(%) by positive control

| DDTC concentration (μM) | 6-OH-CZX concentration (pmol) | CYP 2E1 inhibition (%) |
|---|---|---|
| 0 (control) | 3207.5 | 0 |
| 50 | 1644.5 | 48.66 |
| 100 | 431.2 | 87.56 |

2. Inhibition of CYP 2E1 by Chinese medicine guiding drugs was shown in table 6 and suggested that different guiding drugs have different effects on cytochrome P450 CYP 2E1 activity at various concentrations (66 μM, 33 μM, 16.5 μM) and Nordihydroguaiaretic acid at 66 μM showed the best inhibition activity (96.98±0.19%).

TABLE 7

Inhibition of CYP 2E1 (%) by excipients

| | Inhibition of CYP 2E1 (%) Tested concentration (w/v) | | | Minimum Effective Dose* |
|---|---|---|---|---|
| Excipients | 0.167% | 0.08% | 0.042% | (mg) |
| Control | 0 | 0 | 0 | |
| Brij 58 | 91.24 ± 1.33 | 80.50 ± 1.14 | 62.57 ± 2.10 | 1260 |
| Brij 76 | 86.15 ± 1.02 | 75.71 ± 1.61 | 68.99 ± 3.77 | 1260 |
| Saccharin | 78.5 ± 2.1 (test concentration 66 uM) | 51.2 ± 0.9 (test concentration 33 uM) | 29.4 ± 2.7 (test concentration 16.5 uM) | 10 |

TABLE 6

Inhibition of CYP 2E1(%) by Chinese medicine guiding drugs

| | Inhibition of CYP 2E1 (%) Tested Concentration | | | Minimum Effective |
|---|---|---|---|---|
| Guiding Drugs | 66 μM | 33 μM | 16.5 μM | Dose* (mg) |
| Control | 0 | 0 | 0 | — |
| Nordihydroguaiaretic acid | 96.98 ± 0.19 | 67.68. ± 2.24 | 49.81 ± 2.42 | 17 |
| Trans-Cinnamaldehyde | 92.81 ± 0.53 | 89.56 ± 1.52 | 60.79 ± 3.00 | 7 |
| Daidzein | 86.77 ± 1.04 | 76.33 ± 2.28 | 73.55 ± 1.74 | 14 |
| Isovitexin | 81.82 ± 1.34 | 67.60 ± 3.24 | 59.82 ± 1.41 | 24 |
| Kaempferol | 79.25 ± 0.27 | 74.74 ± 0.60 | 66.53 ± 1.71 | 16 |
| Disulfiram | 78.23 ± 0.25 | 75.75 ± 1.38 | 74.09 ± 1.10 | 17 |
| β-Myrcene | 76.49 ± 2.18 | 75.50 ± 2.14 | 53.40 ± 4.93 | 8 |
| Quercetin | 73.32 ± 1.57 | 53.02 ± 2.17 | 46.40 ± 4.68 | 16 |
| (−)-Epigallocetechin-3-gallate | 72.16 ± 1.02 | 60.53 ± 2.06 | 50.19 ± 1.89 | 25 |
| (+)-Limonene | 63.64 ± 2.74 | 38.05 ± 1.95 | 13.77 ± 1.96 | 7 |
| Myricetin | 61.60 ± 0.88 | 59.21 ± 1.27 | 42.21 ± 2.55 | 17 |
| Quercitrin | 61.04 ± 5.88 | 53.77 ± 3.51 | 33.51 ± 4.29 | 24 |
| Luteolin-7-Glucoside | 60.26 ± 1.11 | 55.87 ± 0.67 | 42.96 ± 5.10 | 24 |
| Morin | 60.26 ± 1.56 | 52.08 ± 1.70 | 36.88 ± 1.56 | 16 |
| Neohesperidin | 58.70 ± 1.06 | 48.96 ± 2.37 | 42.81 ± 1.75 | 33 |
| Hesperidin | 58.57 ± 3.78 | 50.91 ± 2.81 | 45.32 ± 1.57 | 33 |
| Capillarisin | 57.31 ± 1.31 | 46.22 ± 2.65 | 32.89 ± 2.46 | 17 |
| (−)-Epigallocatechin | 57.08 ± 1.85 | 36.40 ± 2.18 | 38.95 ± 1.92 | 17 |
| Hyperoside | 53.51 ± 1.20 | 35.58 ± 3.68 | −24.16 ± 1.19 | 25 |
| Luteolin | 53.23 ± 1.78 | 43.40 ± 4.74 | 39.15 ± 3.42 | 16 |
| Ethyl Myristate | 51.95 ± 2.38 | 41.04 ± 4.76 | 22.08 ± 0.78 | 14 |
| Tamarixetin | 50.91 ± 3.12 | 47.79 ± 2.81 | 37.40 ± 1.96 | 17 |
| Phloretin | 50.90 ± 2.09 | 39.78 ± 3.28 | 29.60 ± 3.21 | 15 |
| Baicalein | 50.13 ± 5.11 | 47.79 ± 3.40 | 35.32 ± 1.51 | 15 |
| Baicalin | 49.30 ± 2.26 | 35.61 ± 3.09 | 22.51 ± 2.24 | 24 |
| Apigenin | 47.51 ± 3.66 | 36.80 ± 1.98 | 28.89 ± 1.54 | 15 |
| Naringenin | 45.16 ± 4.43 | 28.45 ± 2.21 | 19.50 ± 2.02 | 9 |
| Hesperetin | 44.56 ± 2.35 | 34.28 ± 2.03 | 25.74 ± 2.45 | 17 |
| (+)-Epicatechin | 44.32 ± 1.25 | 52.32 ± 1.59 | 66.71 ± 1.79 | 16 |
| Rutin | 43.51 ± 3.09 | 30.13 ± 1.62 | 30.00 ± 0.81 | 33 |
| (−)-Epicatechin-3-gallate | 42.92 ± 0.65 | 34.84 ± 1.72 | 30.31 ± 1.27 | 24 |
| Isoliquritigenin | 41.12 ± 0.92 | 31.48 ± 1.24 | 21.18 ± 1.96 | 18 |
| Silybin | 38.96 ± 1.19 | 37.14 ± 1.15 | 59.48 ± 2.34 | 26 |
| Vitexin | 38.70 ± 1.62 | 30.65 ± 0.78 | 23.12 ± 1.19 | 24 |
| Genistein | 36.88 ± 1.56 | 30.91 ± 1.62 | 43.90 ± 2.06 | 15 |
| Isorhamnetin | 36.31 ± 1.59 | 18.68 ± 1.22 | 12.06 ± 1.06 | 14 |
| gallic acid | 27.96 ± 1.56 | 18.79 ± 2.03 | 10.50 ± 1.12 | 9 |
| Diosmin | 21.56 ± 1.19 | 43.12 ± 3.57 | 60.00 ± 1.96 | 33 |
| 6-Gingerol | 19.08 ± 1.36 | 11.51 ± 1.02 | 7.84 ± 0.92 | 16 |

*Minimum Effective Dose: minimum tested concentration (mg/L) × the volume of human liver and intestine (3 L)

TABLE 7-continued

Inhibition of CYP 2E1 (%) by excipients

| Excipients | Inhibition of CYP 2E1 (%) Tested concentration (w/v) | | | Minimum Effective Dose* (mg) |
|---|---|---|---|---|
| | 0.167% | 0.08% | 0.042% | |
| Brij 35 | 77.28 ± 1.02 | 64.17 ± 1.71 | 42.37 ± 1.78 | 18 |
| | (test concentration 0.025%) | (test concentration 0.013%) | (test concentration 0.006%) | |
| Tween 20 | 75.38 ± 3.64 | 70.44 ± 0.93 | 55.38 ± 1.95 | 1260 |
| PEG 400 | 64.17 ± 1.53 | 54.78 ± 3.53 | 26.42 ± 1.81 | 1260 |
| Microcrystalline cellulose | 60.2 ± 4.1 | 54.4 ± 3.8 | 48.8 ± 0.2 | 180 |
| | (test concentration 0.025%) | (test concentration 0.013%) | (test concentration 0.006%) | |
| Dicalcium phosphate dihydrate | 60.1 ± 0.3 | 56.8 ± 2.2 | 31.2 ± 2.9 | 9 |
| | (test concentration 66 uM) | (test concentration 33 uM) | (test concentration 16.5 uM) | |
| Sucralose | 55.8 ± 2.0 | 45.8 ± 4.0 | 37.1 ± 2.8 | 22 |
| | (test concentration 66 uM) | (test concentration 33 uM) | (test concentration 16.5 uM) | |
| Mannitol | 54.5 ± 4.2 | 51.2 ± 2.1 | 44.8 ± 1.8 | 10 |
| | (test concentration 66 uM) | (test concentration 33 uM) | (test concentration 16.5 uM) | |
| Cremophor RH40 | 50.4 ± 1.1 | 43.2 ± 3.1 | 30.2 ± 2.8 | 1260 |
| Sodium starch glycolate | 50.3 ± 1.9 | 51.3 ± 2.2 | 34.7 ± 1.3 | 158 |
| | | | (test concentration 0.00525%) | |
| PEG 4000 | 47.11 ± 0.92 | 23.94 ± 0.92 | 8.70 ± 0.77 | 1260 |
| PEG 2000 | 47.06 ± 1.53 | 41.43 ± 1.60 | 22.25 ± 1.93 | 1260 |
| Crospovidone | 44.1 ± 0.9 | 40.3 ± 2.1 | 34.8 ± 1.1 | 158 |
| | | | (test concentration 0.00525%) | |
| Tween 40 | 46.34 ± 3.06 | 33.43 ± 2.10 | 16.88 ± 1.17 | 1260 |
| Tween 80 | 39.14 ± 2.40 | 40.56 ± 3.85 | 23.1 ± 3.0 | 158 |
| | | | (test concentration 0.00525%) | |
| Eudragit S100 | 38.1 ± 0.1 | 35.6 ± 2.4 | 10.2 ± 0.3 | 158 |
| | | | (test concentration 0.00525%) | |
| Croscarmellose sodium | 35.4 ± 0.8 | 30.3 ± 2.4 | 4.3 ± 0.3 | 158 |
| | | | (test concentration 0.00525%) | |
| Pluornic F68 | 31.46 ± 1.60 | 17.39 ± 1.07 | 7.93 ± 0.27 | 1260 |
| Menthol | 30.8 ± 0.3 | 20.8 ± 2.1 | 10.5 ± 0.4 | 8 |
| Hydroxypropyl-cellulose | 22.1 ± 0.4 | 20.3 ± 1.1 | 17.5 ± 0.9 | 158 |
| | (test concentration 0.025%) | (test concentration 0.013%) | (test concentration 0.006%) | |
| Pregelatinized starch | 18.3 ± 1.1 | 12.8 ± 0.2 | 10.2 ± 2.3 | 158 |
| | | | (test concentration 0.00525%) | |
| Dextrates NF hydrated | 19.2 ± 1.1 | 14.4 ± 3.2 | 10.6 ± 1.5 | 158 |
| | | | (test concentration 0.00525%) | |
| Citric acid | 20.5 ± 1.8 | 15.5 ± 0.0 | 9.9 ± 3.1 | 10 |
| | (test concentration 66 uM) | (test concentration 33 uM) | (test concentration 16.5 uM) | |
| Cremophor EL | 19.2 ± 0.5 | 15.2 ± 2.2 | 2.4 ± 0.3 | 158 |
| | | | (test concentration 0.00525%) | |
| Aerosil 200 | 15.4 ± 1.1 | 17.8 ± 2.1 | 4.3 ± 0.1 | 158 |
| | | | (test concentration 0.00525%) | |
| Myrj 52 | 18.1 ± 2.6 | 15.7 ± 2.7 | 14.6 ± 1.8 | 1260 |
| PEG 8000 | 21.1 ± 3.4 | 14.2 ± 3.3 | 9.4 ± 0.2 | 1260 |
| Sorbic acid | 14.8 ± 0.1 | 10.9 ± 2.1 | 8.4 ± 1.6 | 6 |
| | (test concentration 66 uM) | (test concentration 33 uM) | (test concentration 16.5 uM) | |
| Lemon oil | 7.8 ± 0.3 | 9.8 ± 0.4 | 2.2 ± 0.4 | 158 |
| | | | (test concentration 0.00525%) | |
| Span 60 | 17.4 ± 0.9 | 13.9 ± 0.7 | 12.4 ± 2.3 | 1260 |
| Sorbitol | 16.1 ± 0.7 | 5.6 ± 0.5 | 4.4 ± 1.7 | 158 |
| | | | (test concentration 0.00525%) | |
| Sodium benzoate | 15.8 ± 0.9 | 7.8 ± 4.1 | 7.1 ± 2.0 | 9 |
| Acesulfame K | 14.5 ± 1.9 | 7.1 ± 2.3 | 3.9 ± 2.7 | 10 |
| Hydroxypropyl methylcellulose | 13.9 ± 2.2 | 13.6 ± 2.6 | 6.1 ± 0.3 | 158 |
| | | | (test concentration 0.00525%) | |
| Hydroxy ethyl methylcellulose | 11.6 ± 0.9 | 13.2 ± 0.6 | 1.7 ± 0.2 | 158 |
| | | | (test concentration 0.00525%) | |
| Methyl cellulose | 10.2 ± 1.7 | 5.5 ± 0.5 | 4.1 ± 1.9 | 158 |
| | | | (test concentration 0.00525%) | |
| Span 80 | 10.1 ± 2.1 | 6.2 ± 0.4 | 5.9 ± 0.3 | 1260 |
| Sodium cyclamate | 9.1 ± 2.6 | 1.7 ± 4.7 | 9.4 ± 2.7 | 10 |
| | (test concentration 66 uM) | (test concentration 33 uM) | (test concentration 16.5 uM) | |
| Lactose monohydrate | 8.7 ± 3.8 | 3.9 ± 2.3 | 7.8 ± 2.2 | 18 |
| | (test concentration 66 uM) | (test concentration 33 uM) | (test concentration 16.5 uM) | |
| Maltodextrin | 8.5 ± 2.8 | 5.9 ± 2.1 | 7.2 ± 1.2 | 158 |
| | | | (test concentration 0.00525%) | |
| Glyceryl behenate | 8.2 ± 2.0 | 3.1 ± 2.5 | 3.1 ± 0.3 | 52 |
| | (test concentration 66 uM) | (test concentration 33 uM) | (test concentration 16.5 uM) | |
| Oxide red | 8.0 ± 5.8 | 10.3 ± 5.3 | 10.7 ± 4.5 | 34 |
| | (test concentration 66 uM) | (test concentration 33 uM) | (test concentration 16.5 uM) | |
| Glycerrin monostearate | 6.9 ± 3.8 | 7.4 ± 2.9 | 5.8 ± 1.7 | 158 |
| | | | (test concentration 0.00525%) | |
| Copovidone K28 | 6.1 ± 0.7 | 4.5 ± 0.5 | 6.4 ± 0.5 | 158 |
| | | | (test concentration 0.00525%) | |
| Starch acetate | 5.3 ± 0.7 | 4.9 ± 1.2 | 4.9 ± 1.4 | 158 |
| | | | (test concentration 0.00525%) | |
| Magnesium stearate | 5.0 ± 1.6 | 3.0 ± 0.7 | 2.0 ± 1.0 | 29 |
| | (test concentration 66 uM) | (test concentration 33 uM) | (test concentration 16.5 uM) | |

TABLE 7-continued

Inhibition of CYP 2E1 (%) by excipients

| Excipients | Inhibition of CYP 2E1 (%) Tested concentration (w/v) | | | Minimum Effective Dose* (mg) |
|---|---|---|---|---|
| | 0.167% | 0.08% | 0.042% | |
| Sodium lauryl sulfate | 4.9 ± 1.6 (test concentration 66 uM) | 6.4 ± 0.9 (test concentration 33 uM) | 4.6 ± 1.1 (test concentration 16.5 uM) | 14 |
| Povidone K-30 | 3.2 ± 0.2 (test concentration 66 uM) | 2.2 ± 0.1 (test concentration 33 uM) | 4.7 ± 1.0 (test concentration 16.5 uM) | 6 |
| Benzyl alcohol | −10.3 ± 6.3 | 6.7 ± 1.0 | 7.7 ± 2.6 (test concentration 0.00525%) | 158 |
| Methylparaben | −21.5 ± 2.0 (test concentration 66 uM) | −14.0 ± 2.2 (test concentration 33 uM) | 4.6 ± 3.2 (test concentration 16.5 uM) | 8 |
| Propylparaben | −27.3 ± 3.7 (test concentration 66 uM) | −17.2 ± 2.4 (test concentration 33 uM) | −4.1 ± 1.2 (test concentration 16.5 uM) | 9 |
| Solutol H15 | −21.0 ± 4.8 (test concentration 0.084%) | −9.3 ± 0.8 (test concentration 0.042%) | 2.7 ± 0.3 (test concentration 0.00525%) | 158 |
| Butylated hydroxyl anisol | −85.5 ± 3.9 (test concentration 66 uM) | −47.1 ± 5.1 (test concentration 33 uM) | −16.8 ± 0.5 (test concentration 16.5 uM) | 9 |

Example 4

Screening of Amidase Inhibitors

Mouse Liver Microsomal Amidase
I. Materials and Methods
(1) Materials

Quantification of Isonicotinic acid by high-performance liquid chromatography (HPLC-UV). All organic solvents were HPLC grade, and were purchased from Tedia Co., Ltd. (Fairfield, Ohio, USA). Isoniazid, isonicotinic acid and nicotinic acid (internal standard) were purchased from Sigma Chemical Company (St. Louis, Mo., USA).

(2) Sample Processing

Mouse liver microsomes were used as the source of amidase, and isoniazid was used as the amidase metabolism drugs. quantitative isoniazid was catalyzed into metabolites isonicotinic acid (INA) by amidase, and was used as the index for measurement of the amidase activity for establishment of the platform for screening in vitro amidase activity inhibitors. The HPLC system includes a Shimadzu the LC-LOAD pump, 1 Shimadzu system control and a Shimadzu autosampler (Shimadzu Scientific Instrument, Japan). A C18 column (particle size 5 μm, inner diameter of 50×4.6 mm, 25 cm) containing 70% methanol and 30% ammonium formate (50 mM, pH=2.5) of the mobile phase for HPLC separation, and the experimental steps are outlined as follows:

(1) Preparation of the mouse liver microsomal enzyme solutions and determination of concentrations.
(2) An aliquot of 150 μL mouse liver microsomal solution was added to 100 μL isoniazid solution in 35 μL 67 mM potassium phosphate buffer solution (KH2PO3, pH=7) with a final concentration at 3 mM, and then mixed thoroughly with 15 μL amidase inhibitor (deionized water was added in the control group).
(3) Incubation at 37° C. water bath for 30 minutes.
(4) An aliquot of 300 μL acetonitrile (ACN) was added and mixed thoroughly, and incubated for 6 minutes.
(5) An aliquot of 30 μL perchloric acid was then mixed and incubated for 6 minutes.
(6) The mixture was centrifuged at 13000 g for 6 minutes.
(7) After centrifugation, 100 μL of the supernatant was injected into HPLC.
(8) Methanol ammonium formate (50 mM, pH=2.5)=70:30 (V/V) was selected as the mobile phase, and the flow rate was controlled at 1 mL/mM and detected at 270 nm UV.
(9) Result analysis: Conversion of the HPLC-UV signal measured values into the amount of isonicotinic acid (ng/mL), which is the amidase metabolite standard, and the control amidase inhibition was selected as baseline and defined as 0% inhibition. The amidase inhibition % was then calculated using the following formula:

$$\text{amidase inhibition}(\%) = 1 - \frac{\text{the amount of isonicotinic acid obtained in test group}}{\text{the amount of isonicotinic acid obtained in control group}}$$

(2) Results

The inhibition of the Amidase measured from the pure ingredients of traditional Chinese herbs/drugs and excipients are shown in Table 8 and 9, respectively. According to the results, various pure ingredients of traditional Chinese herbs/drugs and excipients exhibit different amidase inhibitory effects at different concentrations, and among which 100 μM HUCHE033 showed the best inhibition (75.5±2.2%).

TABLE 8

In vitro Amidase inhibition of the screened compounds of traditional Chinese herbs/drugs

| Screened compound | Amidase inhibition (%) Inhibitory concentration (%) | | | Minimun Effective Dose (mg) |
|---|---|---|---|---|
| | 100 uM | 10 uM | 1 uM | |
| Positive Control (BNPP) | 92.1 ± 8.7 | | | |
| Quercetin | 75.5 ± 2.2 | 62.3 ± 4.4 | 48.1 ± 15.0 | 0.8 |
| Galangin | 61.5 ± 2.7 | 32.8 ± 4.4 | 9.6 ± 9.9 | 0.5 |
| Morin | 59.8 ± 5.1 | 9.1 ± 1.7 | −16.6 ± 4.8 | 0.9 |
| Isoliquirtigenin | 57.2 ± 8.5 | 17.7 ± 8.3 | −18.7 ± 26.0 | 0.8 |
| Myricetin | 56.4 ± 1.5 | 37.8 ± 8.4 | 8.0 ± 4.9 | 0.9 |
| Fisetin | 56.4 ± 2.9 | 38.3 ± 2.0 | −9.2 ± 2.5 | 0.9 |
| Disulfiram | 50.2 ± 9.1 | 42.1 ± 4.1 | 44.1 ± 1.0 | 0.9 |
| Kaempferol | 49.1 ± 8.6 | 25.3 ± 7.8 | 7.3 ± 8.2 | 1.0 |
| Luteolin | 47.5 ± 6.2 | 23.0 ± 6.0 | 6.1 ± 9.1 | 0.6 |
| Capillarisin | 45.7 ± 4.2 | 18.2 ± 3.7 | −4.1 ± 8.1 | 0.4 |
| α-Naphthoflavone | 36.9 ± 2.7 | 19.3 ± 3.7 | 7.3 ± 7.9 | 1.8 |
| (+)-Taxifolin | 36.4 ± 3.4 | 32.2 ± 5.8 | 36.8 ± 11.5 | 1.3 |
| Baicalin | 34.8 ± 10.2 | 15.2 ± 6.3 | 2.1 ± 7.5 | 1.4 |
| Umbelliferone | 33.5 ± 8.2 | −1.0 ± 13.2 | 24.1 ± 11.6 | 0.9 |
| Eriocitrin | 32.8 ± 1.9 | 19.0 ± 3.0 | −16.1 ± 12.8 | 0.8 |
| Isorhamnetin | 31.3 ± 1.3 | 20.0 ± 4.6 | 13.8 ± 1.0 | 1.3 |
| Phloretin | 29.9 ± 8.1 | 9.8 ± 5.4 | 16.5 ± 14.3 | 0.8 |
| Embelin | 29.1 ± 1.2 | 6.6 ± 8.6 | 5.3 ± 5.2 | 1.4 |
| Tamarixetin | 28.9 ± 4.2 | 27.9 ± 6.3 | 3.5 ± 10.5 | 1.8 |
| Oleanolic Acid | 24.5 ± 4.0 | 14.8 ± 3.4 | 20.3 ± 5.2 | 0.8 |
| Glycyrrhizin | 24.4 ± 12.7 | 4.3 ± 11.3 | −1.3 ± 3.1 | 1.3 |
| Nariagenin | 24.2 ± 7.6 | 13.5 ± 9.4 | 11.2 ± 6.5 | 1.0 |
| Chrysoeriol | 23.2 ± 1.2 | 24.9 ± 11.2 | 7.7 ± 7.1 | 0.9 |
| Cineole | 22.9 ± 10.4 | −4.7 ± 4.9 | −16.5 ± 17.5 | 1.8 |
| 6-Gingerol | 22.6 ± 3.4 | 0.5 ± 0.7 | −8.2 ± 9.0 | 1.8 |
| Eriodictyol | 22.3 ± 4.7 | 6.5 ± 11.3 | 9.0 ± 4.7 | 1.4 |
| Isosakuranetin | 22.2 ± 7.3 | −8.9 ± 11.2 | −8.0 ± 10.5 | 1.2 |
| Chrysin | 21.5 ± 2.1 | 24.7 ± 2.2 | 3.5 ± 6.1 | 1.1 |

TABLE 8-continued

In vitro Amidase inhibition of the screened compounds of traditional Chinese herbs/drugs

| Screened compound | Amidase inhibition (%) Inhibitory concentration (%) | | | Minimun Effective Dose (mg) |
|---|---|---|---|---|
| | 100 uM | 10 uM | 1 uM | |
| Sciadopitysin | 20.6 ± 19.3 | 20.7 ± 6.0 | 10.3 ± 3.8 | 1.3 |
| Isoquercitrin | 19.6 ± 5.9 | 5.1 ± 3.6 | −3.7 ± 1.4 | 0.4 |
| Hesperetin | 19.0 ± 3.6 | 5.4 ± 2.5 | −40.5 ± 24.8 | 1.7 |
| Homoorientin | 18.0 ± 2.6 | 3.5 ± 0.9 | 7.4 ± 3.8 | 0.5 |
| Puerarin | 17.9 ± 7.2 | 33.0 ± 3.3 | 40.9 ± 3.6 | 0.8 |
| Poncirin | 17.3 ± 5.8 | 8.1 ± 11.7 | 10.8 ± 3.8 | 0.9 |
| Daidzein | 16.2 ± 12.6 | 1.0 ± 7.4 | −12.1 ± 6.3 | 1.4 |
| Protocatechuic acid | 15.7 ± 8.1 | 10.9 ± 2.0 | 11.5 ± 4.0 | 0.9 |
| Baicalein | 15.6 ± 1.0 | 5.7 ± 2.6 | 2.8 ± 15.1 | 0.9 |
| Luteolin-7-Glucoside | 12.9 ± 3.1 | 8.7 ± 1.9 | 3.2 ± 0.8 | 0.8 |
| Trans-Cinnamic Acid | 12.6 ± 1.7 | −1.4 ± 0.6 | −11.9 ± 2.3 | 0.9 |
| Liquiritin | 12.5 ± 8.3 | −7.5 ± 13.4 | 2.5 ± 2.9 | 0.8 |
| Eupatorin | 12.0 ± 7.4 | 7.5 ± 0.7 | 0.9 ± 2.8 | 0.8 |
| Vitexin | 11.5 ± 1.0 | 6.3 ± 5.0 | −0.6 ± 16.7 | 1.3 |
| Genkwanin | 11.3 ± 1.3 | 2.1 ± 10.0 | 1.6 ± 3.4 | 0.8 |
| Formononetin | 9.8 ± 5.2 | 5.0 ± 0.4 | −2.1 ± 5.0 | 0.5 |
| Sinensetin | 9.7 ± 0.9 | 6.6 ± 0.5 | −0.8 ± 3.0 | 1.1 |
| Curcumin | 9.7 ± 6.0 | 16.1 ± 0.4 | 16.9 ± 11.0 | 1.1 |
| Hyperoside | 8.4 ± 3.7 | 3.8 ± 4.4 | 4.6 ± 2.7 | 1.3 |
| Daidzin | 7.4 ± 6.3 | 1.1 ± 5.4 | 3.6 ± 3.0 | 0.9 |
| Phloridzin | 7.1 ± 13.9 | −3.1 ± 3.4 | −3.2 ± 11.0 | 1.3 |
| (+)-Limonene | 6.2 ± 3.8 | 3.2 ± 8.6 | 5.1 ± 0.4 | 0.5 |
| Genistein | 5.8 ± 6.8 | 1.8 ± 7.6 | −2.1 ± 46.2 | 0.5 |
| β-Myrcene | 5.8 ± 2.7 | 6.6 ± 4.1 | 1.7 ± 1.3 | 0.9 |
| Rutin | 5.7 ± 8.2 | −4.7 ± 4.7 | −5.2 ± 1.2 | 0.9 |
| Terpineol | 4.4 ± 5.2 | 7.0 ± 4.6 | −0.7 ± 5.0 | 1.7 |
| Lauryl Alcohol | 4.1 ± 4.3 | −0.7 ± 1.5 | 2.2 ± 3.1 | 1.8 |
| (−)-Epicatechin | 3.6 ± 4.3 | −4.8 ± 10.5 | −25.8 ± 6.2 | 1.4 |
| (−)-Epigallocatechin | 2.2 ± 4.1 | −7.3 ± 7.6 | −1.2 ± 2.1 | 0.9 |
| Diosmin | 1.6 ± 5.1 | −0.7 ± 7.7 | 0.3 ± 8.1 | 1.2 |
| Quercitrin | 1.6 ± 4.4 | −14.4 ± 5.3 | −14.1 ± 12.1 | 1.3 |
| (+)-Catechin | 1.3 ± 6.3 | −11.8 ± 20.2 | −2.1 ± 1.1 | 0.8 |
| Isovitexin | 1.1 ± 7.1 | 5.8 ± 2.7 | 13.9 ± 2.3 | 2.5 |
| Ergosterol | 0.4 ± 3.6 | −0.4 ± 10.7 | 4.3 ± 10.7 | 1.9 |
| Gallic Acid | −20.2 ± 26.5 | 20.0 ± 5.1 | 12.0 ± 5.5 | 1.3 |
| Apigenin | | 13.2 ± 3.4 | −10.2 ± 20.3 | 1.2 |

* The minimum effective dose: the lowest screening concentration (mg/L) × huamn enterohepatic volume (3 L)

Example 5

Animal Study Results Obtained from Rats Treated with Propylthiouracil Isonicotinic Amide (PZA) and Amidase Inhibitor Nitro-Phenol Phosphate Diester (BNPP)

1. Materials and methods

All organic solvents are HPLC grade and purchased from Tedia (Fairfield, Ohio, USA) and corn oils were purchased from Sigma (St. Louis, Mo., USA). Galactose injection solution was prepared by South Photochemical Pharmaceutical Co., Ltd by dissolving 400 g of galactose in 1 L isotonic buffering distilled water.

2. Animals

Male SD (Sprague-Dawley) rats weighing 320 to 350 g were purchased from National Laboratory Animal Center (Taiwan) and study was performed according to the animal study guidance published by Nation Health Research Institute (NHRI). Throughout the experiment, the rats were housed in air-conditioned and temperature-adjusted cages with a 12-h light/dark cycle and free access to water and food. The body weight of the rats was monitored throughout the experiment. Rats were anesthetized with sodium pentobarbital intraperitoneally (i.p.) at the dose of 50 mg/kg and galactose was injected intravenously through a polyethylene catheter positioned in internal jugular vein. The catheter was positioned by cut-down technique and its end was embedded under the skin behind the neck. After the surgery, the rats were fasted overnight during the recovery period (about 16 hours) with unrestricted water access.

3. Experimental Procedures

Animals were randomized into one of five groups, each involving three treatments. The first treatment involved either a BNPP injection of 50 mg/kg or a BNPP vehicle (VEH1) injection (saline). BNPP was dissolved in saline (0.9% NaCl) after heating to approximately to 60° C., and after cooling, intraperitoneally (i.p.) injected at a volume of 1 mg/kg. The second treatment involved injections of either 500 mg/kg PZA or PZA vehicle (VEH2, saline). PZA was dissolved in

TABLE 9

In vitro Amidase inhibition of screened excipients

| Screened compound | Amidase inhibition (%) Inhibitory concentration (%) | | | Minimun Effective Dose (mg) |
|---|---|---|---|---|
| | 0.05% | 0.005% | 0.0005% | |
| Positive Control (BNPP) | 92.1 ± 8.7 | | | |
| Sodium Lauryl Sulfate | 66.1 ± 2.1 | 19.3 ± 2.7 | 9.6 ± 5.0 | 17 |
| Tween 20 | 64.4 ± 1.2 | 14.9 ± 3.6 | −47.4 ± 14.1 | 17 |
| Cremophor EL | 56.4 ± 2.5 | 7.6 ± 9.6 | 8.3 ± 5.1 | 17 |
| Brij58 | 55.8 ± 9.7 | 16.9 ± 5.5 | 14.3 ± 0.3 | 17 |
| Acesulfame Potassium | 24.3 ± 4.9 | −167.2 ± 167.3 | −12.4 ± 27.4 | 17 |
| Brij76 | 21.0 ± 6.2 | 1.2 ± 6.6 | −10.8 ± 5.7 | 17 |
| Tween 80 | 16.7 ± 6.7 | −3.3 ± 9.9 | 11.9 ± 2.1 | 17 |
| Tween 40 | 15.4 ± 8.1 | 7.2 ± 7.4 | 3.1 ± 4.2 | 17 |
| Mryi52 | 4.0 ± 6.5 | 1.5 ± 3.9 | −3.4 ± 1.3 | 17 |
| Mannitol | 1.9 ± 6.0 | 52.8 ± 7.6 | 58.3 ± 4.3 | 17 |
| Pluronic F68 | 1.2 ± 9.1 | 1.7 ± 6.8 | −1.0 ± 4.7 | 17 |
| PEG400 | 0.3 ± 5.9 | −2.7 ± 7.9 | 1.0 ± 4.2 | 17 |
| PEG2000 | −7.0 ± 7.1 | 9.2 ± 2.8 | 2.5 ± 12.8 | 17 |
| Tween 60 | −10.2 ± 17.4 | −19.0 ± 23.3 | 4.1 ± 8.1 | 17 |
| Pluronic F127 | −13.7 ± 3.1 | −8.0 ± 5.1 | −4.5 ± 2.2 | 17 |
| PEG300 | −19.8 ± 3.2 | −24.7 ± 6.1 | 2.7 ± 9.7 | 17 |

* The minimum effective dose: the lowest screening concentration (mg/L) × huamn enterohepatic volume (3 L)

saline and i.p. injected at a volume of 1 mg/kg. The first treatment (BNPP or VEH1) was administered 15 minutes before the third treatment (PZA or VEH2).

The three treatment groups are:
1. Normal control group (NC, n=10): continuously injections of VEH1, VEH2 and VEH3 intraperitoneally once every day for 49 days;
2. PZA group (PZA, n=10): continuously injections of PZA, VEH1 and VEH2 intraperitoneally once every day for 49 days;
3. BNPP-PZA group (BNPP-PZA, n=10): continuously injections of BNPP, PZA and VEH2 intraperitoneally once every day for 49 days;

Galactose single point (GSP) test was performed 16 hours after the rats were sacrificed at the end of SP days-treatment to measure the liver function.

4. Blood Sampling

After 49 days treatment, the rats were sacrificed with ether and blood samples collected in test tubes containing EDTA by dorsal aorta extract. The blood samples were centrifuged at 13,000 g for 15 min at 4° C. and plasma was aliquot into eppendorf tubes and stored at −80° C.

5. Biochemical Analysis

Hepatocellular damage was quantified by measuring both peak plasma aspartate aminotransferase (AST) and alanine aminotransferase (ALT) activities. AST and ALT activities are the most common biomarkers for hepatotoxicity and were measured by Synchron LXi 725 system (Beckman Instruments, USA).

6. Light Microscopy and Electron Microscopy

After the rats were sacrificed, the livers were subjected to histology analysis. Liver samples were fixed with 10% phosphate-buffered formalin and then, dehydrated and embedded in paraffin. Tissue was sectioned at 5 mm thick and stained with hematoxylin and eosin and Periodic acid Schiff stain (PAS) simultaneously, and results were observed under a light microscope. In addition, liver sections were washed with 0.1M cacodylate buffer (pH 7.4) and then fixed with 20% aqueous osmium tetroxide for 1 hour. Dehydrated and embedded in Spurr resin, and ultra-thin sections were obtained by using a diamond blade and double-stained with uranyl acetate and lead citrate, and sections were further examined under a Transmission Electron Microscope, Hitachi 600 (Hitachi Co., Japan).

7. Quantitative Tests of Liver Function

All rats were subjected to GSP tests. Galactose was injected intravenously within 30 seconds (0.4 g/ml, 0.5 g/kg BW) and blood samples were collected once at 60 minutes post injection by tail vein puncture. The amount of galactose was measured by the concentration of colorimetric galactose dehydrogenase and the tested concentrations ranged from 50 to 1,000 µg/ml. The within-day variation of each concentration was calculated by percentage of standard deviation and coefficient of variation (CV). Day to day variation was determined by examining the slopes and the intercepts of the calibration curves and GSP value was the blood concentration of galactose 60 min after the 30-second injection.

8. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is $P<0.05$.

Results

1. Biochemical Analysis

At the end of the study, no significant differences was found between experimental and control animal groups in their body weight and relative liver weight. Biochemical analysis as shown in FIG. 11, peak plasma AST and ALT activities were significantly increased above control levels only in the PZA group (the plasma AST activities were 109±27 IU/L and 179±10 IU/L in the control and the PZA groups, respectively, ($p<0.05$); and the plasma ALT activities were 43±9 IU/L and 91±11 IU/L in the control and the PZA groups, respectively, ($p<0.05$)) which demonstrated that biochemical hepatocellular injury was induced in the PZA group whereas the concentrations of plasma aminotransferases in the control and BNPP-PZA groups remained normal.

2. Histopathology

After daily i.p. injections of 500 mg/kg for seven weeks, rats in the PZA group showed hepatocellular damage. In contrary, liver structure remained normal in the control group. As shown in FIG. 12A, hepatocytes in liver parenchyma from the control group were arranged inside of mesh plate in the radiation from the centrilobular portal vein, and hepatic sinusoids were found between two anastomosing plates. Liver sections from the PZA group were shown in FIG. 12B, and hepatocytes surrounding the portal vein were fragmented and shown vacuolization. Therefore, liver injury in BNPP-PZA group showed no significant differences in compared with the control group.

3. Residual Liver Function Test

As shown in FIG. 13, the GSP test values between the control group and the PZA group are significantly different (GSP values of the control and PZA groups are 260±50 µg/ml and 776±65 µg/ml, $p<0.005$, respectively). In addition, GSP values of the BNPP-PZA group was 293±61 µg/ml. The BNPP-PZA group was significantly different from the PZA group ($p<0.005$). Furthermore, GSP value was elevated considerably in the PZA group, whereas groups treated with combination drugs of BNPP-PZA can resist such increase. On the other hand, PZA combined with BNPP can significantly reduce PZA-induced hepatotoxicity. Also, no statistical differences were found among the GSP values of the control and the BNPP-PZA groups.

Example 6

Animal Study Results Obtained from Mice Treated with Isoniazid (INH) and/or Rifampin (RIF) and/or Propylthiouracil Isonicotinic Amide (PZA) Alone or Combined with the CYP2E1 Inhibitor Kaempferol or Amidase Inhibitor Quercetin 1. Materials and methods All organic solvents are HPLC grade and purchased from Tedia (Fairfield, Ohio, USA) and INH, RIF, PZA, Kaempferol, Quercetin were purchased from Sigma (St. Louis, Mo., USA). Galactose injection solution was prepared by South Photochemical Pharmaceutical Co., Ltd by dissolving 400 g of galactose in 1 L isotonic buffering distilled water.

2. Animals

129/sv mice weighing 18 to 25 g were purchased from National Laboratory Animal Center (Taiwan) and study was performed according to the animal study guidance published by Nation Health Research Institute (NHRI). Throughout the experiment, the mice were housed in air-conditioned and temperature-adjusted cages with a 12-h light/dark cycle and free access to water and food. The body weight of the mice was monitored throughout the experiment. Mice were anesthetized with ether and galactose was injected intraorbitally.

3. Experimental Procedures

Animals were randomized into one of seven groups, each involving five treatments. The first treatment involved either a Kaempferol injection of 3.78 mg/kg or a vehicle (VEH1) injection (saline). Kaempferol was dissolved in saline (0.9% NaCl) after heating to approximately to 60° C., and after cooling, intraperitoneally (i.p.) injected at a volume of 1 ml/kg. The second treatment involved injections of either 3.02 mg/kg Quercetin or a vehicle (VEH2, saline). Quercetin was dissolved in saline (0.9% NaCl) after heating to approximately to 60° C., and after cooling, intraperitoneally (i.p.) injected at a volume of 1 ml/kg. The third treatment involved injections of either 50 mg/kg INH or a vehicle (VEH3, saline). INH was dissolved in saline (0.9% NaCl) after heating to approximately to 60° C., and after cooling, intraperitoneally (i.p.) injected at a volume of 1 ml/kg. The fourth treatment involved injections of either 100 mg/kg RIF or a vehicle (VEH4, saline). RIF was dissolved in saline (0.9% NaCl) after heating to approximately to 60° C., and after cooling, intraperitoneally (i.p.) injected at a volume of 1 ml/kg. The fifth treatment involved injections of either 100 mg/kg PZA or a vehicle (VEH5, saline). PZA was dissolved in saline (0.9% NaCl) after heating to approximately to 60° C., and after cooling, intraperitoneally (i.p.) injected at a volume of 1 ml/kg.

The seven treatment groups are:

1. Normal control group (NC, n=10): continuously injections of VEH1, VEH2 and VEH3 intraperitoneally once every day for 21 days;

2. INH-RIF group (n=10): continuously injections of INH, RIF, VEH1, VEH2 and VEH5 intraperitoneally once every day for 21 days;

3. Kaempferol-INH-RIF group (n=10): continuously injections of Kaempferol, INH, RIF, VEH2 and VEH5 intraperitoneally once every day for 21 days;

4. Quercetin-INH-RIF group (n=10): continuously injections of Quercetin, INH, RIF, VEH1 and VEH5 intraperitoneally once every day for 21 days;

5. INH-RIF-PZA group (n=10): continuously injections of INH, RIF, PZA, VEH1, and VEH2 intraperitoneally once every day for 21 days;

6. Kaempferol-INH-RIF-PZA group (n=10): continuously injections of Kaempferol, INH, RIF, PZA and VEH2 intraperitoneally once every day for 21 days;

7. Quercetin-INH-RIF-PZA group (n=10): continuously injections of Quercetin, INH, RIF, PZA and VEH1 intraperitoneally once every day for 21 days;

Galactose single point (GSP) test was performed 16 hours after the mice were sacrificed at the end of SP days-treatment to measure the liver function.

4. Blood Sampling

After 21 days treatment, the rats were sacrificed with ether and blood samples collected in test tubes containing EDTA by dorsal aorta extract. The blood samples were centrifuged at 13,000 g for 15 min at 4° C. and plasma was aliquot into eppendorf tubes and stored at −80° C.

5. Biochemical Analysis

Hepatocellular damage was quantified by measuring both peak plasma aspartate aminotransferase (AST) and alanine aminotransferase (ALT) activities. AST and ALT activities are the most common biomarkers for hepatotoxicity and were measured by Synchron LXi 725 system (Beckman Instruments, USA).

6. Light Microscopy and Electron Microscopy

After the mice were sacrificed, the livers were subjected to histology analysis. Liver samples were fixed with 10% phosphate-buffered formalin and then, dehydrated and embedded in paraffin. Tissue was sectioned at 5 mm thick and stained with hematoxylin and eosin and Periodic acid Schiff stain (PAS) simultaneously, and results were observed under a light microscope. In addition, liver sections were washed with 0.1M cacodylate buffer (pH 7.4) and then fixed with 20% aqueous osmium tetroxide for 1 hour. Dehydrated and embedded in Spurr resin, and ultra-thin sections were obtained by using a diamond blade and double-stained with uranyl acetate and lead citrate, and sections were further examined under a Transmission Electron Microscope, Hitachi 600 (Hitachi Co., Japan).

7. Quantitative Tests of Liver Function

All mice were subjected to GSP tests. Galactose was injected intravenously within 30 seconds (0.4 g/ml, 0.5 g/kg BW) and blood samples were collected once at 60 minutes post injection by tail vein puncture. The amount of galactose was measured by the concentration of colorimetric galactose dehydrogenase and the tested concentrations ranged from 50 to 1,000 µg/ml. The within-day variation of each concentration was calculated by percentage of standard deviation and coefficient of variation (CV). Day to day variation was determined by examining the slopes and the intercepts of the calibration curves and GSP value was the blood concentration of galactose 60 min after the 30-second injection.

8. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is $P<0.05$.

Results

1. Biochemical Analysis

The weight of the tested mice and their relative liver weights were measured at the end of the study, and no significant difference was observed when compared with the control group. Biochemical analysis results (as shown in FIG. 14 and Table 10) indicated that the activities of plasma aspartate aminotransferase (AST) and alanine aminotransferase (ALT) were significantly higher than the control group when treated with 50/100 mg/kg/day INH/RIF for 3 weeks (blank AST plasma activity was 90±15 IU/L; AST plasma activity in the INH/RIF control group, the AST plasma activity in test group was 571±295 IU/L, $p<0.001$; blank plasma ALT activity was 40±5 IU/L; the plasma ALT activity in INH/RIF control group was 364±192 IU/L, $p<0.001$), which implied that INH/RIF indeed induced biochemical liver damage in these mice. Moreover, in mice treated with 50/100/250 mg INH/RIF/PZA/kg/day continuously for 3 weeks, the plasma AST and ALT activities of the INH/RIF/PZA control group were 702±172 IU/L and 464±72 IU/L, respectively, which were significantly higher than blank control group and the INH/RIF control group, and further demonstrated that INH/RIF/PZA certainly induced biochemical liver damage in the treated mice, and the resulted damage was more severe than that in INH/RIF treated mice. On the contrary, for the mice treated with the CYP2E1 inhibitor, Kaempferol, or the amidase inhibitor, Quercetin, the serum concentrations of AST and ALT in Quercetin-INH-RIF, Kaempferol-INH-RIF, Quercetin-INH-RIF-PZA, and Kaempferol-INH-RIF-PZA experimental groups were all close to normal range.

TABLE 10

Analysis of Aspartate aminotransferase (AST) activity, Alanine aminotransferase (ALT) activity, and total HAI score among the control, INH-RIF, KH-INH-RIF, KM-INH-RIF, KL-INH-RIF, MH-INH-RIF, and tML-INH-RIF groups (mean ± SD).

| Liver function parameters | AST (IU/L) | ALT (IU/L) | Total HAI score |
|---|---|---|---|
| Normal control (n = 9) | 80 ± 13 | 46 ± 10 | 0.0 ± 0.0 |
| INH-RIF (n = 8) | 420 ± 66 | 358 ± 67 | 5.3 ± 2.2 |
| KH-INH-RIF (n = 8) | 93 ± 12*** | 60 ± 12*** | 1.8 ± 0.7* |
| KM-INH-RIF (n = 6) | 96 ± 15*** | 77 ± 30*** | 1.7 ± 0.8* |
| KL-INH-RIF (n = 6) | 111 ± 27*** | 128 ± 36*** | 2.8 ± 1.3* |
| MH-INH-RIF (n = 8) | 93 ± 12*** | 54 ± 18*** | 0.8 ± 0.5*** |
| MM-INH-RIF (n = 6) | 85 ± 16*** | 52 ± 12*** | 0.7 ± 0.8*** |
| ML-INH-RIF (n = 6) | 154 ± 62* | 119 ± 55** | 2.0 ± 0.6* |

Data are shown as mean ± SD.
*$p < 0.05$,
**$p < 0.01$,
***$p < 0.005$: Study compare to control group.

2. Histopathology

After daily i.p. injections of 50/100 mg/kg/day INH/RIF and 50/100/250 mg/kg/day INH/RIF/PZA for three weeks, the treated mice showed hepatotoxicity. In contrary, the liver tissue remained relatively normal in the blank control group. On the other hand, mice in the Kaempferol-INH-RIF, Quercetin-INH-RIF, Kaempferol-INH-RIF-PZA and Quercetin-INH-RIF-PZA groups showed no apparent fragmentation around the centrlobular portal vein, and less vacuolization and inflammation were observed in compared with the mice received INH/RIF/PZA treatment.

As for HAI score that was used to asses the level of damage shown in liver histopathological sections, after continuous treatments of INH-RIF or INH-RIF-PZA for 3 weeks, Intralobular Degeneration and Focal Necrosisall were significantly improved. Moreover, Piecemeal necrosis was found in the INH-RIF and INH-RIF-PZA control groups, whereas considerable improvements were noted in Kaempferol-INH-RIF, Quercetin-INH-RIF, Kaempferol-INH-RIF-PZA and Quercetin-INH-RIF-PZAgroups (as shown in FIGS. 16 and 17).

Residual Liver Function Test

As shown in FIG. 15, the GSP test values between the INH-RIF group or INH-RIF-PZA group and the control group are significantly different (GSP values of the control, INH-RIF, INH-RIF-PZA groups are 177±22 µg/ml, 866±339 µg/ml and 858±172 µg/ml, $p<0.001$, respectively). In addition, GSP values of the Kaempferol-INH-RIF, Quercetin-INH-RIF, Kaempferol-INH-RIF-PZA and Quercetin-INH-RIF-PZA group were 401±178 mg/L, 203±76 mg/L, 273±61 mg/L and 216±67 mg/L which were significantly different from the PZA group ($p<0.005$). Furthermore, GSP value was elevated considerably in the INH-RIF group or INH-RIF-PZA group, whereas groups treated with combination of Quercetin and Kaempferol can resist such increase. Also, no statistical differences were found among the GSP values of the control and the Kaempferol-INH-RIF, Quercetin-INH-RIF, Kaempferol-INH-RIF-PZA and Quercetin-INH-RIF-PZA groups.

Example 7

Animal Study Results Obtained from Mice Treated with Isoniazid (INH) and Rifampin (RIF) Combined with the CYP2E1 Inhibitor (Kaempferol), Mannitol, Saccharin, Sucralose, Dicalcium phosphate, or Crospovidone 1. Materials and methods All organic solvents are HPLC grade and purchased from Tedia (Fairfield, Ohio, USA) and INH, RIF, Kaempferol, Mannitol, Saccharin, Sucralose, Dicalcium phosphate and Crospovidone were purchased from Sigma (St. Louis, Mo., USA). Galactose injection solution was prepared by South Photochemical Pharmaceutical Co., Ltd by dissolving 400 g of galactose in 1 L isotonic buffering distilled water.

2. Animals

129/sv mice weighing 18 to 25 g were purchased from National Laboratory Animal Center (Taiwan) and study was performed according to the animal study guidance published by Nation Health Research Institute (NHRI). Throughout the experiment, the mice were housed in air-conditioned and temperature-adjusted cages with a 12-h light/dark cycle and free access to water and food. The body weight of the mice was monitored throughout the experiment. Mice were anesthetized with ether and galactose was injected intraorbitally.

3. Experimental Procedures

Animals were randomized into one of thirteen groups, each involving three treatments. The first treatment involved a Kaempferol oral solution of 1.67, 4.27 or 8.33 mg/kg or a mannitol oral solution of 0.17, 0.83 or 1.67 mg/kg or a Saccharin oral solution of 0.83 mg/kg or a Sucralose oral solution of 1.67 mg/Kg or a Saccharin 0.83 mg/kg+Mannitol 0.83 mg/kg oral solution or a Dicalcium phosphate oral solution of 0.83 mg/Kg or a Crospovidone oral solution of 2.83 mg/Kg. The second treatment involved injections of either 50 mg/kg INH or a vehicle (VEH1, saline). INH was dissolved in saline (0.9% NaCl) after heating to approximately to 60° C., and after cooling, intraperitoneally (i.p.) injected at a volume of 1 ml/kg. The third treatment involved injections of either 100 mg/kg RIF or a vehicle (VEH2, saline). RIF was dissolved in saline (0.9% NaCl) after heating to approximately to 60° C., and after cooling, intraperitoneally (i.p.) injected at a volume of 1 ml/kg.

The five treatment groups include:
(1) Normal control group (NC, n=10): continuously injections of VEH1 and VEH2 intraperitoneally once every day for 21 days;
(2) INH-RIF group (INH-RIF, n=10): continuously injections of INH and RIF intraperitoneally once every day for 21 days;
(3) KL-INH-RIF group (KL-INH-RIF, n=8): continuously injections of INH and RIF intraperitoneally and oral administrations of Kaempferol 1.67 mg/kg once every day for 21 days;
(4) KM-INH-RIF group (KM-INH-RIF, n=6): continuously injections of INH and RIF intraperitoneally and oral administrations of Kaempferol 4.17 mg/kg once every day for 21 days;
(5) KH-INH-RIF group (KH-INH-RIF, n=6): continuously injections of INH and RIF intraperitoneally and oral administrations of Kaempferol 8.33 mg/kg once every day for 21 days;
(6) ML-INH-RIF group (ML-INH-RIF, n=8): continuously injections of INH and RIF intraperitoneally and oral administrations of Mannitol 0.17 mg/kg once every day for 21 days;

(7) MM-INH-RIF group (MM-INH-RIF, n=6): continuously injections of INH and RIF intraperitoneally and oral administrations of Mannitol 0.83 mg/kg once every day for 21 days;
(8) MH-INH-RIF group (MM-INH-RIF, n=6): continuously injections of INH and RIF intraperitoneally and oral administrations of Mannitol 1.67 mg/kg once every day for 21 days;
(9) SA-INH-RIF group (SA-INH-RIF, n=4): continuously injections of INH and RIF intraperitoneally and oral administrations of Saccharin 0.83 mg/kg once every day for 21 days;
(10) SU-INH-RIF group (SU-INH-RIF, n=4): continuously injections of INH and RIF intraperitoneally and oral administrations of Saccharin 1.67 mg/kg once every day for 21 days;
(11) SAM-INH-RIF group (SAM-INH-RIF, n=4): continuously injections of INH and RIF intraperitoneally and oral administrations of Saccharin 0.83 mg/kg+Mannitol 0.83 mg/kg once every day for 21 days;
(12) D-INH-RIF group (D-INH-RIF, n=4): continuously injections of INH and RIF intraperitoneally and oral administrations of Dicalcium phosphate 0.83 mg/kg once every day for 21 days;
(13) C-INH-RIF group (C-INH-RIF, n=4): continuously injections of INH and RIF intraperitoneally and oral administrations of Crospovidone 2.83 mg/kg once every day for 21 days;

4. Blood Sampling

Upon completion of the treatment, the mice were sacrificed with ether and blood samples collected by dorsal aorta extract and transferred to test tubes containing Heparin. The blood were centrifuged at 13,000 g for 10 min at 4° C. and plasma was aliquot into eppendorf tubes and stored at −80° C.

5. Biochemical Analysis

Hepatocellular damage was quantified by measuring both peak plasma aspartate aminotransferase (AST) and alanine aminotransferase (ALT) activities. AST and ALT activities are the most common biomarkers for hepatotoxicity and were measured by Synchron LXi 725 system (Beckman Instruments, USA).

6. Light Microscopy and Electron Microscopy

After the mice were sacrificed, the livers were subjected to histology analysis. Liver samples were fixed with 10% phosphate-buffered formalin and then, dehydrated and embedded in paraffin. Tissue was sectioned at 5 mm thick and stained with hematoxylin and eosin and Periodic acid Schiff stain (PAS) simultaneously, and results were observed under a light microscope. In addition, liver sections were washed with 0.1M cacodylate buffer (pH 7.4) and then fixed with 20% aqueous osmium tetroxide for 1 hour. Dehydrated and embedded in Spurr resin, and ultra-thin sections were obtained by using a diamond blade and double-stained with uranyl acetate and lead citrate, and sections were further examined under a Transmission Electron Microscope, Hitachi 600 (Hitachi Co., Japan).

6. Quantitative Tests of Liver Function

All mice were subjected to GSP test. Galactose was retroorbitally injected within 30 seconds (0.4 g/ml, 0.5 g/kg BW) and blood samples were collected once at 60 minutes post injection by tail vein puncture. The amount of galactose was measured by the concentration of colorimetric galactose dehydrogenase and the tested concentrations ranged from 50 to 1,000 μg/ml. The within-day variation of each concentration was calculated by percentage of standard deviation and coefficient of variation (CV). In addition, the maximal acceptable coefficient of variation (CV) was 10% and the day to day variation was determined by examining the slopes and the intercepts of the calibration curves. GSP value was the blood concentration of galactose 60 min after the 30-second injection.

7. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is $P<0.05$.

(1) Results

1. Biochemical Analysis

At the end of the study, no significant differences was found between experimental and control animal groups in their body weight and relative liver weight. Biochemical analysis as shown in FIG. 18, plasma AST and ALT activities in INH/RIF control group which mice were continuously treated with 50/100 mg/kg/day INH/RIF for 3 weeks were significantly higher than blank control group (the plasma AST activities were 80±13 IU/L and 420±66 IU/L in blank control and the INH/RIF groups, respectively, ($p<0.01$); and the plasma ALT activities were 46±10 IU/L and 358±67 IU/L in the control and the INH/RIF groups, respectively, ($p<0.01$)) which demonstrated that biochemical hepatocellular injury was induced in the INH/RIF group while the concentrations of plasma aminotransferases in the groups that received CYP2E1 inhibitors including Kaempferol and Mannitol were all notably less than the INH/RIF control group.

1. Histopathology

After daily i.p. injections of 50/100 mg/kg/day INH/RIF for three weeks, mice in the INH/RIF group showed hepatocellular damage. In contrary, liver structure remained relatively normal in the blank control group. On the other hand, comparison of the mice received different Mannitol treatments and INH-RIF group indicated that no apparent fragmentation was observed around the centrlobular portal vein with less vacuolization and inflammation in various Mannitol groups (FIG. 18).

As for HAI score that was used to asses the level of damage shown in liver histopathological sections, after continuous treatments of INH-RIF for 3 weeks, significant improvement was found in all Kaempferol- and Mannitol-treated groups when compared to the INH/RIF control group.

2 Residual Liver Function Test

GSP test values of the INH/RIF group increased along with the INH/RIF treatment time, and significant differences were observed between GSP values of the blank and INH-RIF control groups (GSP values of the blank and INH-RIF control groups after 3-week treatment were 192±18 mg/L and 666±126 mg/L, respectively. ($p<0.001$)). Nonetheless, GSP values measured from the mice in the groups that were treated with Kaempferol, Mannitol, Saccharin, Sucralose or Dicalcium phosphate remained constant, and no significant differences were noted between the blank control group and experimental groups including KH-INH-RIF, KM-INH-RIF, MH-INH-RIF, MM-INH-RIF, and SU-INH-RIF groups (as shown in Table 11).

TABLE 11

Galactose single point (GSP) test results of the INH-RIF control, KH-INH-RIF, KM-INH-RIF, KL-INH-RIF, MH-INH-RIF, MM-INH-RIF, ML-INH-RIF, SA-INH-RIF, SU-INH-RIF, SAM-INH-RIF, INH-RIF and C-INH-RIF groups. All representative values are mean ± standard deviation (SD).

| GSP (mg/L) | 0 weeks | 2 weeks | 3 weeks | Anova and LSD 0-2 | 0-3 | 2-3 |
|---|---|---|---|---|---|---|
| Normal control (n = 4) | 197 ± 16 | 186 ± 19 | 192 ± 18 | ND | ND | ND |
| INH-RIF (n = 8) | 201 ± 23 | 472 ± 128 | 666 ± 126 | <0.005 | <0.005 | <0.01 |
| KH-INH-RIF (n = 8) | 199 ± 19 | 195 ± 41 | 254 ± 34 | ND | ND | ND |
| KM-INH-RIF (n = 6) | 195 ± 26 | 221 ± 17 | 262 ± 33 | ND | ND | ND |
| KL-INH-RIF (n = 6) | 212 ± 34 | 290 ± 43 | 327 ± 50 | <0.005 | <0.005 | ND |
| MH-INH-RIF (n = 8) | 196 ± 22 | 208 ± 26 | 252 ± 24 | ND | ND | ND |
| MM-INH-RIF (n = 6) | 201 ± 17 | 240 ± 29 | 237 ± 30 | ND | ND | ND |
| ML-INH-RIF (n = 6) | 188 ± 26 | 287 ± 28 | 300 ± 40 | <0.01 | <0.01 | ND |
| SA-INH-RIF (n = 4) | 199 ± 21 | 269 ± 40 | 258 ± 28 | ND | ND | ND |
| SU-INH-RIF (n = 4) | 203 ± 19 | 300 ± 31 | 399 ± 22 | <0.005 | <0.005 | <0.05 |
| SAM-INH-RIF (n = 4) | 196 ± 22 | 240 ± 38 | 223 ± 29 | ND | ND | ND |
| D-INH-RIF (n = 4) | 208 ± 25 | 249 ± 35 | 366 ± 77 | ND | <0.005 | <0.01 |
| C-INH-RIF (n = 4) | 193 ± 7 | 330 ± 56 | 459 ± 76 | <0.005 | <0.005 | ND |

Data are shown as mean ± SD.
*$p < 0.05$, $p < 0.01$, *$p < 0.005$: Study compare to control group.

Example 8

Animal Study of INH, RIF and PZA Treatments Combined with the CYP2E1 Inhibitor, Mannitol 1. Materials and Methods All organic solvents are HPLC grade and purchased from Tedia (Fairfield, Ohio, USA) and INH, RIF, PZA and Mannitol were purchased from Sigma (St. Louis, Mo., USA). Galactose injection solution was prepared by South Photochemical Pharmaceutical Co., Ltd by dissolving 400 g of galactose in 1 L isotonic buffering distilled water.

2. Animals

Three male and 4 female 129/sv mice weighing 18 to 25 g were purchased from Dr. Gonzalez at National Institute of Health (USA), After breeding, study was performed according to the animal study guidance published by Nation Health Research Institute (NHRI). Throughout the experiment, the mice were housed in air-conditioned and temperature-adjusted cages with a 12-h light/dark cycle and free access to water and food. The body weight of the mice was monitored throughout the experiment. Mice were anesthetized with ether at the dose of 50 mg/kg and galactose was retro-orbitally injected and blood samples were collected 60 min after injection through tail vein.

3. Experimental Procedures

Animals were randomized into one of three groups, each involving four treatments. The first treatment involved Mannitol oral administration of 1.67 mg/kg in the volume of 0.1 ml/kg. The second treatment involved injections of 50 mg/kg INH or INH vehicle (VEH1, normal saline). INH was dissolved in normal saline (0.9% NaCl) and i.p. injected at a volume of 1 mg/kg. The third treatment involved injections of RIF (100 mg/kg) or RIF vehicle (VEH2, saline). RIF was dissolved in saline (0.9% NaCl), and i.p. injected at a volume of 1 mg/kg. The fourth treatment involved injections of PZA (250 mg/kg) or PZA vehicle (VEH3, saline). PZA was dissolved in saline (0.9% NaCl), and i.p. injected at a volume of 1 mg/kg.

The three treatment groups are:

Normal control group (NC, n=10): continuously injections of VEH1, VEH2 and VEH3 intraperitoneally once every day for 21 days;

INH-RIF-PZA group (n=6): continuously injections of INH, RIF and PZA intraperitoneally once every day for 21 days;

M-INH-RIF-PZA group (n=6): continuously injections of INH, RIF and PZA intraperitoneally and oral administration of Mannitol 1.67 mg/kg once every day for 21 days;

4. Blood Sampling

After 21 days treatment, the rats were sacrificed with ether and blood samples collected in test tubes containing EDTA by dorsal aorta extract. The blood samples were centrifuged at 13,000 g for 10 min at 4° C. and plasma was aliquot into eppendorf tubes and stored at −80° C.

5. Quantitative Tests of Liver Function

All mice were subjected to GSP test. Galactose was retro-orbitally injected within 30 seconds (0.4 g/ml, 0.5 g/kg BW) and blood samples were collected once at 60 minutes post injection by tail vein puncture. The amount of galactose was measured by the concentration of colorimetric galactose dehydrogenase and the tested concentrations ranged from 50 to 1,000 μg/ml. The within-day variation of each concentration was calculated by percentage of standard deviation and coefficient of variation (CV). In addition, the maximal acceptable coefficient of variation (CV) was 10% and the day to day variation was determined by examining the slopes and the intercepts of the calibration curves. GSP value was the blood concentration of galactose 60 min after the 30-second injection.

6. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is P<0.05.

(1) Result

1. Residual Liver Function Test

GSP test values of the INH/RIF/PZA group increased along with the INH/RIF treatment time, and significant differences were observed between GSP values of the blank and INH-RIF-PZA control groups (GSP values of the blank and INH-RIF control groups after 3-week treatment were 570±293 mg/L and 948±236 mg/L, respectively. (p<0.001)). However, GSP values measured from the Mannitol group reamined constant (as shown in Table 12).

TABLE 12

Galactose single point (GSP) test results of the control, INH-RIF-PZA and M-INH-RIF-PZA groups. All representative values are mean ± standard deviation (SD).

| GSP(mg/L) | NC (n = 6) | INH-RIF-PZA (n = 8) | M-INH-RIF-PZA (n = 6) |
|---|---|---|---|
| 0 weeks | 344 ± 196 | 372 ± 172 | 356 ± 144 |
| 2 weeks | 381 ± 157 | 431 ± 103 | 283 ± 178 |
| 3 weeks | 570 ± 293 | 948 ± 236 | 296 ± 102*** |

Data are shown as mean ± SD.
*p < 0.05,
**p < 0.01,
***p < 0.005: Study compare to control group.

Example 9

The Effects of the No/Low Side Effect INH/RIF Pharmaceutical Composition on Relevant In Vivo INH Metabolism Enzymes in Healthy Volunteers I. Materials and Methods 1. Experimental Procedures Pharmacokinetic studies were conducted in healthy subjects by administration of combined drugs including CYP2E1 phenotyping drugs, Chlorzoxazone 500 mg and Rifamate, (Isoniazid 150 mg/Rifampin 300 mg), and Mannitol 100 mg. During the experiment, plasma Chlorzoxazone (CZX), its metabolites and major biochemical values of ALT, AST and GSP were monitored closely so as to assess the change of CYP2E1 activity in the presence and absence of the CYP2E1 inhibitors in healthy subjects.

2. Experimental Groups

The trial was conducted in the Tri-Service General Hospital Clinical Research Center and included two individual treatments that were one week apart. The first treatment involved an oral administration of brand name Rifamate (Isoniazid 150 mg/Rifampin 300 mg) and Chlorzoxazone (500 mg of). One week after first treatment, the same group of subjects were given brand name Rifamate (Isoniazid 150 mg/Rifampin 300 mg)+Mannitol (100 mg) and Chlorzoxazone (500 mg).

3. Assessment and Statistical Analysis

The collected data was analyzed statistically and presented as an integrated overview. The results obtained from pharmacokinetic studies were represented as means and standard deviations, and will be further analyzed by one-way analysis of variance (ANOVA) or other appropriate statistical methods.

Result

1 Blood Analysis

Eighteen subjects have completed the clinical trial including 9 subjects in the control group (Chlorzoxazone 500 mg+Isoniazid 300 mg) and 9 subjects in the experimental group (Chlorzoxazone 500 mg+Isoniazid 300 mg+HUCHE033 180 mg). The results indicated that no significant differences in the pharmacokinetic parameters were observed in the group treated with both HUCHE033 and Chlorzoxazone; however, the Cmax of CYP2E1 metabolite 6-OH Chlorzoxazone was significantly lower, and metabolism of 6-OH-Chlorzoxazone/Chlorzoxazone was also notably lower than the control group (FIGS. 19, 20, and Table 13).

TABLE 13

Phamarkinetic (PK) parameters of Chlorzoxazone and its metabolite 6-OH Chlorzoxazone in healthy subjected treated with Chlorzoxazone + Rifamatein the presence or absence of Mannitol. Data are shown as mean ± SD.

| | PK parameters | Control (n = 4) | Mannitol (n = 4) | Folds |
|---|---|---|---|---|
| CZX | T½(hr) | 1.42 ± 0.28 | 1.25 ± 0.26 | 0.88 |
| | Tmax(hr) | 2.00 ± 0.00 | 2.00 ± 0.00 | 1.00 |
| | C/max(ug/mL) | 16.15 ± 1.81 | 22.18 ± 2.35 | 1.37 *** |
| | AUCi(hr* ug/mL) | 61.72 ± 3.31 | 86.14 ± 6.17 | 1.40 *** |
| | AUCi(hr* ug/mL) | 62.21 ± 3.20 | 87.65 ± 4.79 | 1.41 *** |
| 60H-CZX | Tmax(hr) | 5.50 ± 1.00 | 4.50 ± 1.00 | 0.82 |
| | C/max(ug/mL) | 1.21 ± 0.15 | 0.75 ± 0.06 | 0.62 * |
| | AUCi(hr* ug/mL) | 6.76 ± 0.50 | 3.99 ± 0.53 | 0.59 ** |
| | AUCi(hr* ug/mL) | 7.15 ± 0.64 | 4.15 ± 0.55 | 0.58 * |
| | Metabolic Ratio | 0.11 ± 0.01 | 0.05 ± 0.01 | 0.42 *** |

Data represent mean ± S.D..
* p < 0.05,
** p < 0.01,
*** p < 0.005
* Mtabolic Ratio: AUC t 6OH-CZX/AUCt czx The compositions, methods and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. For example, the concentrations and ratios of INH, cytochrome P450 2E1 inhibitors, and amidase inhibitors; and the types of cytochrome P450 2E1 inhibitors and amidase inhibitors selected, etc. All such similar substitutes and modifications apparent to those skilled in the art are deemed to be within the scope and concept of the invention.

What is claimed is:

1. A no/low side effect anti-TB pharmaceutical composition comprising:
   (a) anti-TB drugs selected from rifampin (RIF), pyrazinamide (PZA) or ethambutol (EMB), and
   (b) at least one pharmaceutically effective compound that reduces side effects caused by the anti-TB drugs;
   wherein the pharmaceutically effective compound included to reduce the anti-TB drug side effects was selected from the following compounds: Nordihydroguaiaretic acid, and the amount of said Nordihydroguaiaretic acid ranges from 17 mg to 10 g; (−)-Epigallocetechin-3-gallate, and the amount of said (−)-Epigallocetechin-3-gallate ranges from 25 mg to 10 g; Capillarisin, and the amount of said Capillarisin ranges from 17 mg to 10 g; Kaempferol, and the amount of said Kaempferol ranges from 16 mg to 10 g; Phloretin, and the amount of said Phloretin ranges from 15 mg to 10 g; Hesperetin, and the amount of said Hesperetin ranges from 17 mg to 10 g; 6-Gingerol, and the amount of said 6-Gingerol ranges from 16 mg to 10 g; gallic acid, and the amount of said gallic acid ranges from 9 mg to 10 grams; Isoliquiritigenin, and the amount of said Isoliquiritigenin ranges from 18 mg to 10 g; Naringenin, and the amount of said naringenin ranges from 9 mg to 10 g; (+)-Taxifolin, and the amount of said (+)-Taxifolin ranges from 17 mg to 10 g; Wogonin, and the amount of said Wogonin ranges from 16 mg to 10 g; Protocatechuic acid, and the amount of said protocatechuic acid content ranges from 8 mg to 10 g; (+)-Catechin, and the amount of said (+)-Catechin ranges from 16 mg to 10 g; β-naphthoflavone, and the amount of said β-naphthoflavone ranges from 15 mg to 10 g; Embelin, and the amount of said Embelin ranges from 16 mg to 10 g; Trans-Cinnamic acid, and the amount of said Trans-Cinnamic acid ranges from 8 mg to 10 g; (−)-Epicatechin, and the amount of said (−)-Epicatechin ranges from 16 mg to 10 g; Phloridzin, Brij 58, and the amount of said Phloridzin, Brij 58 ranges from 24 mg to 10 g; Trans-Cinnamaldehyde, and the amount of said Trans-Cinnamaldehyde ranges from 7 mg to 10 g; Daidzein, and the amount of said Daidzein ranges from 14 mg to 10 g; Isovitexin, and the amount of said Isovitexin ranges from 24 mg to 10 g; β-Myrcene, and the amount of said β-Myrcene ranges from 8 mg to 10 g; Quercetin, and the amount of said Quercetin ranges from 0.9 mg to 10 g; (+)-Limonene, and the amount of said (+)-Limonene ranges from 7 mg to 10 g; Myricetin, and the amount of said Myricetin ranges from 17 mg to 10 g; Quercetin, and the amount of said Quercetin ranges from 24 mg to 10 g; Luteolin-7-Glucoside, and the amount of said Luteolin-7-Glucoside ranges from 24 mg to 10 g; Morin, and the amount of said Morin ranges from 16 mg to 10 g; Neohesperidin, and the amount of said Neohesperidin ranges from 33 mg to 10 g; Hesperidin, and the amount of said Hesperidin ranges from 33 mg to 10 g; (−)-Epigallocatechin, and the amount of said (−)-Epigallocatechin ranges from 17 mg to 10 g; Luteolin; and the amount of said (−)-Epigallocatechin ranges from 16 mg to 10 g; Hyperoside, and the amount of said Hyperoside ranges from 25 mg to 10 g; Tamarixetin, and the amount of said Tamarixetin ranges from 17 mg to 10 g; Baicalein, and the amount of said Baicalein ranges from 15 mg to 10 g; Rutin, and the amount of said Rutin ranges from 15 mg to 10 g; Baicalin, and the amount of said Baicalin ranges from 24 mg to 10 g; Apigenin, and the amount of said Apigenin ranges from 15 mg to 10 g; (+)-Epicatechin, and the amount of said (+)-Epicatechin ranges from 16 mg to 10 g; (−)-Epicatechin-3-gallate, and the amount of said (−)-Epicatechin-3-gallate ranges from 24 mg to 10 g; Silybin, and the amount of said Silybin ranges from 26 mg to 10 g; Vitexin, and the amount of said Vitexin ranges from 24 mg to 10 g; Genistein, and the amount of said Genistein ranges from 15 mg to 10 g; Isorhamnetin, and the amount of said Isorhamnetin ranges from 14 mg to 10 g; Diosmin, and the amount of said Diosmin ranges from 33 mg to 10 g; Puerarin, and the amount of said Puerarin ranges from 23 mg to 10 g; Umbelliferone, and the amount of said Umbelliferone ranges from 9 mg to 10 g; Galangin, and the amount of said Galangin ranges from 0.8 mg to 10 g; Fisetin, and the amount of said Fisetin ranges from 0.8 mg to 10 g; Brij 58, and the amount of said Brij 58 ranges from 1.4 to 10 g; Brij 76, and the amount of said Brij 76 ranges from 1.4 to 10 g; Brij 35, and the amount of said Brij 35 ranges from 18 mg to 10 g; Tween 20, and the amount of said Tween 20 ranges from 1.4 to 10 g; Tween 80, and the amount of said Tween 80 ranges from 170 mg to 10 g; Tween 40, and the amount of said Tween 40 ranges from 1.4 to 10 g; PEG 2000, and the amount of said PEG 2000 ranges from 1.4 g to 10 g; PEG 400, and the amount of said PEG 400 ranges from 1.4 to 10 g; Pluornic F68, and the amount of said Pluornic F68 ranges from 1.4 to 10 g; PEG 4000, and the amount of said PEG 4000 ranges from 1.4 to 10 g; tetradecanoic acid ethyl ester, and the amount of said ranges from 14 mg to 10 g; Cremophor EL, and the amount of said Cremophor EL ranges from 17 mg to 10 g; Sodium Lauryl Sulfate, and the amount of said Sodium Lauryl Sulfate ranges from 17 mg to 10 g; Microcrystalline cellulose, and the amount of said Microcrystalline cellulose ranges from 190 mg to 10 g; Dicalcium phosphate, and the amount of said Dicalcium phosphate dihydrate ranges from 9 mg to 10 g; Cremophor RH40, and the amount of said Cremophor RH40 ranges from 1.26 to 10 g; Crospovidone, and the amount of said Crospovidone ranges from 158 mg to 10 g; Sodium starch glycolate, and the amount of said Sodium starch glycolate ranges from 158 mg to 10 g; Eudragit S100, and the amount of said Eudragit S100 ranges from 158 mg to 10 g; Croscarmellose sodium, and the amount of said Croscarmellose sodium ranges from 158 mg to 10 g; Menthol, and the amount of said Menthol ranges from 8 mg to 10 g; Hydroxypropylcellulose, and the amount of said Hydroxypropylcellulose ranges from 158 mg to 10 g; Pregelatinized starch, and the amount of said Pregelatinized starch ranges from 158 mg to 10 g; Mannitol, and the amount of said Mannitol ranges from 0.1 mg to 10 g; Dextrates NF hydrated, and the amount of said Dextrates NF hydrated ranges from 158 mg to 10 g; Citric acid, and the amount of said Citric acid ranges from 10 mg to 10 g; Aerosil 200, and the amount of said Aerosil 200 ranges from 158 mg to 10 g; PEG 8000, and the amount of said PEG 8000 ranges from 1.26 to 10 g; Sorbic acid, and the amount of said Sorbic acid ranges from 6 mg to 10 g; Lemon oil, and the amount of said Lemon oil ranges from 158 mg to 10 g; Sodium benzoate, and the amount of said Sodium benzoate ranges from 9 mg to 10 g; Acesulfame K, and the amount of said of Acesulfame K ranges from 10 mg to 10 g; Hydroxypropyl methylcellulose, and the amount of said Hydroxypropyl methylcellulose ranges from 158 mg to 10 g; Hydroxy ethyl methylcellulose, and the amount of said Hydroxy ethyl methylcellulose ranges from 158 mg to 10 g; Saccharin, and the amount of said Saccharin ranges from 0.1 mg to 10 g; Methyl cellulose, and the amount of said Methyl cellulose ranges from 158 mg to 10 g; Sodium cyclamate, and the amount of said Sodium cyclamate ranges from 10 mg to 10 g; Lactose monohydrate, and the amount of said Lactose monohydrate ranges from 18 mg to 10 g; Maltodextrin, and the amount of said Maltodextrin ranges from 158 mg to 10 g; Glyceryl behenate, and the amount of said Glyceryl behenate ranges from 52 mg to 10 g; Oxide red, and the amount of said Oxide red ranges from 34 mg to 10 g; Glycerrin monostearate, and the amount of said Glycerrin monostearate ranges from 158 mg to 10 g; Copovidone K28, and the amount of Copovidone K28 ranges from 158 mg to 10 g; Starch acetate, and the amount of said Starch acetate ranges from 158 mg to 10 g; Magnesium stearate, and the amount of said Magnesium stearate ranges from 29 mg to 10 g; Sodium lauryl sulfate, and the amount of said Sodium lauryl sulfate ranges from 14 mg to 10 g; Povidone K-30, and the amount of said Povidone K-30 ranges from 6 mg to 10 g; Sucralose, and the amount of said Sucralose ranges from 0.22 mg to 10 g; Benzyl alcohol, and the amount of said Benzyl alcohol ranges from 158 mg to 10 g; Methylparaben, and the amount of said Methylparabenranges from 8 mg to 10 g; Propylparaben, and the amount of said Propylparaben ranges from 9 mg to 10 g; Solutol H15, and the amount of said Solutol H15 ranges from 158 mg to 10 g; and Butylated hydroxyl anisol, and the amount of said Butylated hydroxyl anisol ranges from 9 mg to 10 g.

2. The pharmaceutical composition according to claim 1, further comprising suitable pharmaceutical acceptable excipients.

3. The pharmaceutical composition according to claim 2, wherein the excipients are diluents, fillers, binders, disintegrants or lubricants.

4. The no/low side effect anti-TB pharmaceutical composition of claim 1, wherein the formulations of anti-TB drug compound comprising oral tablets, capsules, powders, solutions, suspensions, emulsions, aromatic agent, syrup, spiritus agent, elixir, tincture, fluidextract, ointment, cream agent, paste, injection or suppository thereof.

5. A no/low side effect anti-TB pharmaceutical composition comprising:
(a) anti-TB drugs selected from at least any two of the following drugs of isoniazid (INH), rifampin (RIF), pyrazinamide (PZA), and ethambutol (EMB); and
(b) at least one pharmaceutically effective compound that reduces side effects caused by the anti-TB drugs;
wherein the anti-TB compound used to reduce the side effects caused by anti-TB drugs was selected from the following compounds: the pharmaceutically effective compound included to reduce the anti-TB drug side effects was selected from the following compounds:
Nordihydroguaiaretic acid, and the amount of said Nordihydroguaiaretic acid ranges from 17 mg to 10 g; (−)-Epigallocetechin-3-gallate, and the amount of said (−)-Epigallocetechin-3-gallate ranges from 25 mg to 10 g; Capillarisin, and the amount of said Capillarisin ranges from 17 mg to 10 g; Kaempferol, and the amount of said Kaempferol ranges from 16 mg to 10 g; Phloretin, and the amount of said Phloretin ranges from 15 mg to 10 g; Hesperetin, and the amount of said Hesperetin ranges from 17 mg to 10 g; 6-Gingerol, and the amount of said 6-Gingerol ranges from 16 mg to 10 g; gallic acid, and the amount of said gallic acid ranges from 9 mg to 10 grams; Isoliquiritigenin, and the amount of said Isoliquiritigenin ranges from 18 mg to 10 g; Naringenin, and the amount of said naringenin ranges from 9 mg to 10 g; (+)-Taxifolin, and the amount of said (+)-Taxifolin ranges from 17 mg to 10 g; Wogonin, and the amount of said Wogonin ranges from 16 mg to 10 g; Protocatechuic acid, and the amount of said protocatechuic acid content ranges from 8 mg to 10 g; (+)-Catechin, and the amount of said (+)-Catechin ranges from 16 mg to 10 g; β-naphthoflavone, and the amount of said β-naphthoflavone ranges from 15 mg to 10 g; Embelin, and the amount of said Embelin ranges from 16 mg to 10 g; Trans-Cinnamic acid, and the amount of said Trans-Cinnamic acid ranges from 8 mg to 10 g; (−)-Epicatechin, and the amount of said (−)-Epicatechin ranges from 16 mg to 10 g; Phloridzin, Brij 58, and the amount of said Phloridzin, Brij 58 ranges from 24 mg to 10 g; Trans-Cinnamaldehyde, and the amount of said Trans-Cinnamaldehyde ranges from 7 mg to 10 g; Daidzein, and the amount of said Daidzein ranges from 14 mg to 10 g; Isovitexin, and the amount of said Isovitexin ranges from 24 mg to 10 g; β-Myrcene, and the amount of said β-Myrcene ranges from 8 mg to 10 g; Quercetin, and the amount of said Quercetin ranges from 0.9 mg to 10 g; (+)-Limonene, and the amount of said (+)-Limonene ranges from 7 mg to 10 g; Myricetin, and the amount of said Myricetin ranges from 17 mg to 10 g; Quercetin, and the amount of said Quercetin ranges from 24 mg to 10 g; Luteolin-7-Glucoside, and the amount of said Luteolin-7-Glucoside ranges from 24 mg to 10 g; Morin, and the amount of said Morin ranges from 16 mg to 10 g; Neohesperidin, and the amount of said Neohesperidin ranges from 33 mg to 10 g; Hesperidin, and the amount of said Hesperidin ranges from 33 mg to 10 g; (−)-Epigallocatechin, and the amount of said (−)-Epigallocatechin ranges from 17 mg to 10 g; Luteolin; and the amount of said (−)-Epigallocatechin ranges from 16 mg to 10 g; Hyperoside, and the amount of said Hyperoside ranges from 25 mg to 10 g; Tamarixetin, and the amount of said Tamarixetin ranges from 17 mg to 10 g; Baicalein, and the amount of said Baicalein ranges from 15 mg to 10 g; Rutin, and the amount of said Rutin ranges from 15 mg to 10 g; Baicalin, and the amount of said Baicalin ranges from 24 mg to 10 g; Apigenin, and the amount of said Apigenin ranges from 15 mg to 10 g; (+)-Epicatechin, and the amount of said (+)-Epicatechin ranges from 16 mg to 10 g; (−)-Epicatechin-3-gallate, and the amount of said (−)-Epicatechin-3-gallateranges from 24 mg to 10 g; Silybin, and the amount of said Silybin ranges from 26 mg to 10 g; Vitexin, and the amount of said Vitexin ranges from 24 mg to 10 g; Genistein, and the amount of said Genistein ranges from 15 mg to 10 g; Isorhamnetin, and the amount of said Isorhamnetin ranges from 14 mg to 10 g; Diosmin, and the amount of said Diosmin ranges from 33 mg to 10 g; Puerarin, and the amount of said Puerarin ranges from 23 mg to 10 g; Umbelliferone, and the amount of said Umbelliferone ranges from 9 mg to 10 g; Galangin, and the amount of said Galangin ranges from 0.8 mg to 10 g; Fisetin, and the amount of said Fisetin ranges from 0.8 mg to 10 g; Brij 58, and the amount of said Brij 58 ranges from 1.4 to 10 g; Brij 76, and the amount of said Brij 76 ranges from 1.4 to 10 g; Brij 35, and the amount of said Brij 35 ranges from 18 mg to 10 g; Tween 20, and the amount of said Tween 20 ranges from 1.4 to 10 g; Tween 80, and the amount of said Tween 80 ranges from 170 mg to 10 g; Tween 40, and the amount of said Tween 40 ranges from 1.4 to 10 g; PEG 2000, and the amount of said PEG 2000 ranges from 1.4 g to 10 g; PEG 400, and the amount of said PEG 400 ranges from 1.4 to 10 g; Pluornic F68, and the amount of said Pluornic F68 ranges from 1.4 to 10 g; PEG 4000, and the amount of said PEG 4000 ranges from 1.4 to 10 g; tetradecanoic acid ethyl ester, and the amount of said ranges from 14 mg to 10 g; Cremophor EL, and the amount of said Cremophor EL ranges from 17 mg to 10 g; Sodium Lauryl Sulfate, and the amount of said Sodium Lauryl Sulfate ranges from 17 mg to 10 g; Microcrystalline cellulose, and the amount of said Microcrystalline cellulose ranges from 190 mg to 10 g; Dicalcium phosphate, and the amount of said Dicalcium phosphate dihydrateranges from 9 mg to 10 g; Cremophor RH40, and the amount of said Cremophor RH40 ranges from 1.26 to 10 g; Crospovidone, and the amount of said Crospovidone ranges from 158 mg to 10 g; Sodium starch glycolate, and the amount of said Sodium starch glycolate ranges from 158 mg to 10 g; Eudragit S100, and the amount of said Eudragit S100 ranges from 158 mg to 10 g; Croscarmellose sodium, and the amount of said Croscarmellose sodium ranges from 158 mg to 10 g; Menthol, and the amount of said Menthol ranges from 8 mg to 10 g;

Hydroxypropylcellulose, and the amount of said Hydroxypropylcellulose ranges from 158 mg to 10 g; Pregelatinized starch, and the amount of said Pregelatinized starch ranges from 158 mg to 10 g; Mannitol, and the amount of said Mannitol ranges from 0.1 mg to 10 g; Dextrates NF hydrated, and the amount of said Dextrates NF hydrated ranges from 158 mg to 10 g; Citric acid, and the amount of said Citric acid ranges from 10 mg to 10 g; Aerosil 200, and the amount of said Aerosil 200 ranges from 158 mg to 10 g; PEG 8000, and the amount of said PEG 8000 ranges from 1.26 to 10 g; Sorbic acid, and the amount of said Sorbic acid ranges from 6 mg to 10 g; Lemon oil, and the amount of said Lemon oil ranges from 158 mg to 10 g; Sodium benzoate, and the amount of said Sodium benzoateranges from 9 mg to 10 g; Acesulfame K, and the amount of said of Acesulfame K ranges from 10 mg to 10 g; Hydroxypropyl methylcellulose, and the amount of said Hydroxypropyl methylcellulose ranges from 158 mg to 10 g; Hydroxy ethyl methylcellulose, and the amount of said Hydroxy ethyl methylcellulose ranges from 158 mg to 10 g; Saccharin, and the amount of said Saccharin ranges from 0.1 mg to 10 g; Methyl cellulose, and the amount of said Methyl cellulose ranges from 158 mg to 10 g; Sodium cyclamate, and the amount of said Sodium cyclamate ranges from 10 mg to 10 g; Lactose monohydrate, and the amount of said Lactose monohydrate ranges from 18 mg to 10 g; Maltodextrin, and the amount of said Maltodextrin ranges from 158 mg to 10 g; Glyceryl behenate, and the amount of said Glyceryl behenate ranges from 52 mg to 10 g; Oxide red, and the amount of said Oxide red ranges from 34 mg to 10 g; Glycerrin monostearate, and the amount of said Glycerrin monostearate ranges from 158 mg to 10 g; Copovidone K28, and the amount of Copovidone K28 ranges from 158 mg to 10 g; Starch acetate, and the amount of said Starch acetate ranges from 158 mg to 10 g; Magnesium stearate, and the amount of said Magnesium stearate ranges from 29 mg to 10 g; Sodium lauryl sulfate, and the amount of said Sodium lauryl sulfate ranges from 14 mg to 10 g; Povidone K-30, and the amount of said Povidone K-30 ranges from 6 mg to 10 g; Sucralose, and the amount of said Sucralose ranges from 0.22 mg to 10 g; Benzyl alcohol, and the amount of said Benzyl alcohol ranges from 158 mg to 10 g; Methylparaben, and the amount of said Methylparabenranges from 8 mg to 10 g; Propylparaben, and the amount of said Propylparaben ranges from 9 mg to 10 g; Solutol H15, and the amount of said Solutol H15 ranges from 158 mg to 10 g; and Butylated hydroxyl anisol, and the amount of said Butylated hydroxyl anisol ranges from 9 mg to 10 g.

6. The pharmaceutical composition according to claim 5, further comprising suitable pharmaceutical acceptable excipients.

7. The pharmaceutical composition according to claim 6, wherein the excipients are diluents, fillers, binders, disintegrants or lubricants.

8. The no/low side effect anti-TB pharmaceutical composition of claim 5, wherein the dosage forms of said anti-TB pharmaceutical composition include oral tablet, capsule, powder, solution, suspension, emulsion, aromatic water, syrup, spirit, elixir, tincture, fluid extract, ointment, cream, paste, injection or suppository thereof.

9. A no/low side effect anti-TB pharmaceutical composition comprising:
(a) anti-TB drug isoniazid (INH); and
(b) at least one pharmaceutically effective compound that reduces side effects caused by the anti-TB drugs; wherein the pharmaceutically effective compound included to reduce the anti-TB drug side effects was selected from the following compounds: tetradecanoic acid ethyl ester, and the amount of said ranges from 14 mg to 10 g; Microcrystalline cellulose, and the amount of said Microcrystalline cellulose ranges from 190 mg to 10 g; Dicalcium phosphate, and the amount of said Dicalcium phosphate dihydrateranges from 9 mg to 10 g; Cremophor RH40, and the amount of said Cremophor RH40 ranges from 1.26 to 10 g; Crospovidone, and the amount of said Crospovidone ranges from 158 mg to 10 g; Sodium starch glycolate, and the amount of said Sodium starch glycolate ranges from 158 mg to 10 g; Eudragit S100, and the amount of said Eudragit S100 ranges from 158 mg to 10 g; Croscarmellose sodium, and the amount of said Croscarmellose sodium ranges from 158 mg to 10 g; Menthol, and the amount of said Menthol ranges from 8 mg to 10 g; Hydroxypropylcellulose, and the amount of said Hydroxypropylcellulose ranges from 158 mg to 10 g; Pregelatinized starch, and the amount of said Pregelatinized starch ranges from 158 mg to 10 g; Dextrates NF hydrated, and the amount of said Dextrates NF hydrated ranges from 158 mg to 10 g; Citric acid, and the amount of said Citric acid ranges from 10 mg to 10 g; Aerosil 200, and the amount of said Aerosil 200 ranges from 158 mg to 10 g; PEG 8000, and the amount of said PEG 8000 ranges from 1.26 to 10 g; Sorbic acid, and the amount of said Sorbic acid ranges from 6 mg to 10 g; Lemon oil, and the amount of said Lemon oil ranges from 158 mg to 10 g; Sodium benzoate, and the amount of said Sodium benzoateranges from 9 mg to 10 g; Acesulfame K, and the amount of said of Acesulfame K ranges from 10 mg to 10 g; Hydroxypropyl methylcellulose, and the amount of said Hydroxypropyl methylcellulose ranges from 158 mg to 10 g; Hydroxy ethyl methylcellulose, and the amount of said Hydroxy ethyl methylcellulose ranges from 158 mg to 10 g; Saccharin, and the amount of said Saccharin ranges from 0.1 mg to 10 g; Methyl cellulose, and the amount of said Methyl cellulose ranges from 158 mg to 10 g; Sodium cyclamate, and the amount of said Sodium cyclamate ranges from 10 mg to 10 g; Lactose monohydrate, and the amount of said Lactose monohydrate ranges from 18 mg to 10 g; Maltodextrin, and the amount of said Maltodextrin ranges from 158 mg to 10 g; Glyceryl behenate, and the amount of said Glyceryl behenate ranges from 52 mg to 10 g; Oxide red, and the amount of said Oxide red ranges from 34 mg to 10 g; Glycerrin monostearate, and the amount of said Glycerrin monostearate ranges from 158 mg to 10 g; Copovidone K28, and the amount of Copovidone K28 ranges from 158 mg to 10 g; Starch acetate, and the amount of said Starch acetate ranges from 158 mg to 10 g; Magnesium stearate, and the amount of said Magnesium stearate ranges from 29 mg to 10 g; Povidone K-30, and the amount of said Povidone K-30 ranges from 6 mg to 10 g; Sucralose, and the amount of said Sucralose ranges from 0.22 mg to 10 g; Benzyl alcohol, and the amount of said Benzyl alcohol ranges from 158 mg to 10 g; Methylparaben, and the amount of said Methylparabenranges from 8 mg to 10 g; Propylparaben, and the amount of said Propylparaben ranges from 9 mg to 10 g; Solutol H15, and the amount of said Solutol H15 ranges from 158 mg to 10 g; and Butylated hydroxyl anisol, and the amount of said Butylated hydroxyl anisol ranges from 9 mg to 10 g.

10. The pharmaceutical composition according to claim 9, further comprising suitable pharmaceutical acceptable excipients.

11. The pharmaceutical composition according to claim 9, wherein the excipients are diluents, fillers, binders, disintegrants or lubricants.

12. The pharmaceutical composition according to claim 9, wherein the formulations of anti-TB drug compound comprising oral tablets, capsules, powders, solutions, suspensions, emulsions, aromatic agent, syrup, spiritus agent, elixir, tincture, fluidextract, ointment, cream agent, paste, injection or suppository thereof.

* * * * *